United States Patent
Rudolf et al.

(10) Patent No.: US 7,230,001 B1
(45) Date of Patent: Jun. 12, 2007

(54) ARYLALKANE, ARYLALKENE AND ARYL AZAALKANE, MEDICAMENTS CONTAINING SAID COMPOUNDS AND METHOD FOR THE PRODUCTION THEREOF

(75) Inventors: Klaus Rudolf, Warthausen (DE); Wolfgang Eberlein, Biberach (DE); Wolfhard Engel, Biberach (DE); Henri Doods, Warthausen (DE); Gerhard Hallermayer, Maselheim-Sulmingen (DE); Eckhart Bauer, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 145 days.

(21) Appl. No.: 10/110,347

(22) PCT Filed: Oct. 24, 2000

(86) PCT No.: PCT/EP00/10463

§ 371 (c)(1),
(2), (4) Date: Jan. 7, 2003

(87) PCT Pub. No.: WO01/32649

PCT Pub. Date: May 10, 2001

(30) Foreign Application Priority Data

Oct. 29, 1999 (DE) ................................ 199 52 146

(51) Int. Cl.
*C07D 401/04* (2006.01)
*A61K 31/4523* (2006.01)
*C07D 333/00* (2006.01)

(52) U.S. Cl. ................. 514/266.22; 514/322; 514/326; 544/286; 546/199; 546/210

(58) Field of Classification Search ................ 544/286; 546/199, 210; 514/266.22, 322, 326
See application file for complete search history.

(56) References Cited

U.S. PATENT DOCUMENTS 4,018,823 A 4/1977 Schwan
4,073,790 A 2/1978 Archibald et al.
4,199,590 A 4/1980 Ward
5,190,741 A 3/1993 Moreau et al.
5,432,172 A 7/1995 Spector et al.
5,508,306 A 4/1996 Chiu et al.
5,747,485 A 5/1998 Doherty et al.

FOREIGN PATENT DOCUMENTS

| EP | 0 005 658 | 11/1979 |
|---|---|---|
| EP | 0 441 333 A1 | 8/1991 |
| EP | 0 444 924 A1 | 9/1991 |
| EP | 1 024 130 A1 | 8/2000 |
| GB | 1 393 979 | 12/1972 |
| GB | 1 500 973 | 5/1975 |
| GB | 1 503 551 | 5/1975 |
| GB | 1 530 931 | 5/1976 |
| JP | 11071350 | 3/1999 |
| WO | WO 97/03951 | 2/1997 |
| WO | WO 98/11128 | 3/1998 |

OTHER PUBLICATIONS

Nakao et al., CAPLUS Abstract 83:193319, 1975.*
CAPLUS Abstract 79:92021, 1973.*
Brain et al., Vascular Actions of Calcitonin Gene-Related Peptide and Adrenomedullin, Physiol. Rev. vol. 84, pp. 903-934, Jul. 2004.*

* cited by examiner

*Primary Examiner*—Deepak Rao
(74) *Attorney, Agent, or Firm*—Michael P. Morris; Mary-Ellen M. Devlin; Alan R. Stempel

(57) ABSTRACT

The present invention relates to compounds of general formula $$R-Z^1-Z^2-Z^3-R^1, \qquad (I)$$

wherein
R, $R^1$ and $Z^1$ to $Z^3$ are defined as in claim 1, the tautomers, the diastereomers, the enantiomers, the mixtures thereof and the salts thereof, particularly the physiologically acceptable salts thereof with inorganic or organic acids or bases, which have valuable pharmacological properties, particularly CGRP-antagonistic properties, pharmaceutical compositions containing these compounds, their use and processes for preparing them.

9 Claims, No Drawings

ARYLALKANE, ARYLALKENE AND ARYL AZAALKANE, MEDICAMENTS CONTAINING SAID COMPOUNDS AND METHOD FOR THE PRODUCTION THEREOF

APPLICATION DATA

This application is a 35 USC 371 case of PCT application PCT/EP 00/10463.

The present invention relates to compounds of general formula

the tautomers, the diastereomers, the enantiomers, the mixtures thereof and the salts thereof, particularly the physiologically acceptable salts thereof with inorganic or organic acids or bases, pharmaceutical compositions containing these compounds, their use and processes for preparing them.

In the above general formula I

R denotes the $H_2N$ group or the group of formula

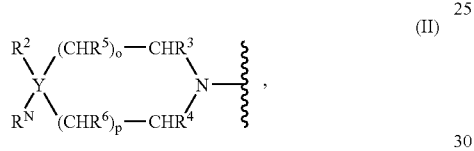

wherein o denotes the number 1 or, if Y does not denote a nitrogen atom, also denotes the number 0, p denotes the number 1 or, if Y does not denote a nitrogen atom, also denotes the number 0, Y denotes the carbon atom or, if Y is not linked to a heteroatom, may also denote the nitrogen atom, $R^2$ denotes a pair of free electrons, if Y denotes the nitrogen atom, or, if Y denotes the carbon atom, denotes the hydrogen atom or an alkyl group with 1 to 3 carbon atoms, $R^3$ and $R^4$ denote hydrogen atoms or together denote an alkylene bridge with 1 to 3 carbon atoms, $R^5$ and $R^6$ denote hydrogen atoms or together denote a one- to three-membered unbranched alkylene bridge wherein a methylene group may be replaced by a methylimino group, $R^N$ denotes a saturated, mono- or diunsaturated 5- to 7-membered aza, diaza, triaza, oxaza, thiaza, thiadiaza or S,S-dioxido-thiadiaza heterocycle, wherein the abovementioned heterocycles may be linked via a carbon or nitrogen atom and adjacent to a nitrogen atom may contain a carbonyl, thioxo or iminocarbonyl group or two carbonyl groups or a carbonyl group and a thioxo or iminocarbonyl group, wherein the abovementioned iminocarbonyl groups may be substituted by a cyano group or by an alkoxycarbonyl group with 1 to 4 carbon atoms in the alkyl moiety, may be substituted at one of the nitrogen atoms by an alkanoyl, hydroxycarbonylalkyl or alkoxycarbonylalkyl group, may be substituted at one or two carbon atoms by a branched or unbranched alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, wherein the substituents may be identical or different, wherein additionally an unbranched alkylene group with 3 to 6 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or an olefinic double bond of one of the abovementioned unsaturated heterocycles may be fused to a benzene, pyridine, diazine, 1,3-oxazole, thiophene, furan, thiazole, pyrrole, N-methyl-pyrrole, quinoline, imidazole or N-methyl-imidazole ring, or, if Y denotes the carbon atom, $R^N$ denotes the hydroxy group, a benzoylaminocarbonylamino group, a phenylamino group optionally substituted at the aniline nitrogen by an aminocarbonyl group or a phenylmethylamino group optionally substituted at the benzylamine nitrogen by an alkoxycarbonyl group, wherein the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in the groups mentioned under $R^N$ as well as benzo-, thieno-, pyrido-, diazino- and quinolino-fused heterocycles in the carbon skeleton may additionally be mono-, di- or trisubstituted by fluorine, chlorine or bromine atoms, by alkyl groups, by cycloalkyl groups with 3 to 8 carbon atoms, nitro, alkoxy, alkylthio, alkylsulphinyl, alkylsulphonyl, alkylsulphonylamino, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, cycloalkanecarbonylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, [4-(1-piperidinyl)-piperidinyl]carbonyl, [4-(1-piperidinyl)-piperidinyl]carbonylamino, methylenedioxy, aminocarbonylamino, aminocarbonylaminoalkyl, alkylaminocarbonylamino, dialkylaminocarbonylamino, aminomethyl, alkanoyl, cyano, trifluoromethoxy, trifluoromethylthio, trifluoromethylsulphinyl or trifluoromethylsulphonyl groups, wherein the substituents may be identical or different and the abovementioned benzoyl, benzoylamino, benzoylaminocarbonylamino and benzoylmethylamino groups may in turn additionally be substituted in the phenyl moiety by a fluorine, chlorine or bromine atom, an alkyl, trifluoromethyl, amino or acetylamino group, and the alkyl groups contained in the abovementioned groups, unless otherwise stated, may contain 1 to 5 carbon atoms, or, if $Z^1$—$Z^2$—$Z^3$ denotes the divalent group CO—$CH_2$—$CH_2$—CO, R may also denote the 4-[3,4-dihydro-2(1H)-oxoquinazolin-3-yl]-[1.4']bipiperidinyl-1'-yl group, $Z^1$ denotes a methylene or carbonyl group or, if $Z^2$ denotes a divalent group of general formula III, may also denote a bond, $Z^2$ denotes one of the groups $-(CH_2)_2-$ or $-(CH_2)_3-$,
wherein a hydrogen atom may be replaced by a $C_{1-3}$-alkyl or a hydroxy group, one of the groups $-NH-CH_2$, $-CH_2-NH$, $-NH-(CH_2)_2-$ or $-(CH_2)_2-NH-$,
wherein a hydrogen atom bound to a carbon atom and/or the hydrogen atom of the imino group may each be replaced by a $C_{1-3}$-alkyl group and the nitrogen atoms are each linked to a carbonyl group of the groups $Z^1$ or $Z^3$, the group $-CH=CH-$ or a divalent group of general formula

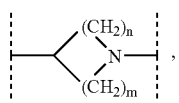

(III)

wherein
m and n independently of one another denote one of the numbers 1, 2, 3 or 4 and
the nitrogen atom is linked to a carbonyl group of the group $Z^3$, $Z^3$ denotes the methylene or carbonyl group,
wherein at least one of the groups $Z^1$ and $Z^3$ denotes a carbonyl group, and $R^1$ denotes a phenyl, 1-naphthyl, 2-naphthyl, benzimidazolyl, 1,3-dihydro-2-oxobenzimidazolyl, octahydro-9-phenanthryl or benzodioxolanyl group,
wherein the abovementioned aromatic and heteroaromatic groups in the carbon skeleton may additionally be mono-, di- or trisubstituted by fluorine, chlorine, bromine or iodine atoms, by alkyl groups, by cycloalkyl groups with 3 to 8 carbon atoms, phenylalkyl groups, hydroxy, alkoxy, phenyl, phenylalkoxy, trifluoromethyl, alkoxycarbonylalkyl, carboxyalkyl, alkoxycarbonyl, carboxy, dialkylaminoalkyl, amino, aminoalkyl, alkylamino, dialkylamino, acetylamino, propionylamino, benzoyl, benzoylamino, benzoylmethylamino, 4-(dialkylaminoalkyl)-1-piperazinyl, piperidinyl, 4-(1-piperidinyl)-1-piperidinyl, 4-(4-methyl-1-piperazinyl)-1-piperidinyl, 4-(4-dialkylaminoalkyl-1-piperazinyl)-1-piperidinyl, nitro, methanesulphonyloxy, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups and the substituents may be identical or different and the abovementioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, wherein the hydroxy, amino and imidazolyl groups contained in the abovementioned groups may be substituted with protecting groups well known from peptide chemistry, preferably with the acetyl, benzyloxycarbonyl or tert.butyloxycarbonyl group, all the abovementioned alkyl and alkoxy groups and the alkyl or alkylene moieties present inside the other groups specified may contain 1 to 7 carbon atoms, unless otherwise stated, and all the abovementioned cycloalkyl groups and the cycloalkyl groups present inside the other groups specified may contain 5 to 10 carbon atoms, unless otherwise stated.

By the protecting groups mentioned in the preceding definitions are meant the protecting groups familiar from peptide chemistry, especially a phenylalkoxycarbonyl group with 1 to 3 carbon atoms in the alkoxy moiety optionally substituted in the phenyl nucleus by a halogen atom, by a nitro or phenyl group, by one or two methoxy groups,
for example the benzyloxycarbonyl, 2-nitro-benzyloxycarbonyl, 4-nitro-benzyloxycarbonyl, 4-methoxy-benzyloxy-carbonyl, 2-chloro-benzyloxycarbonyl, 3-chloro-benzyloxy-carbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group having a total of 1 to 5 carbon atoms in the alkyl moiety,
for example the methoxycarbonyl, ethoxycarbonyl, n-propoxycarbonyl, isopropoxycarbonyl, n-butoxycarbonyl, 1-methylpropoxycarbonyl, 2-methylpropoxy-carbonyl or tert.butyloxycarbonyl group, the allyloxycarbonyl, 2,2,2-trichloro-(1,1-dimethylethoxy)-carbonyl or 9-fluorenylmethoxycarbonyl group or the formyl, acetyl or trifluoroacetyl group.

The present invention relates to racemates if the compounds of general formula I have only one chiral element. However, the application also includes the individual diastereomeric pairs of antipodes or mixtures thereof which are obtained if there is more than one chiral element in the compounds of general formula (I). Of the compounds that come under general formula I wherein $Z^2$ denotes the group $-CH=CH-$, the (E)-configured diastereomers are preferred.

The compounds of general formula (I) have valuable pharmacological properties, based on their selective CGRP-antagonistic properties. The invention further relates to pharmaceutical compositions containing these compounds, their use and the preparation thereof.

Preferred compounds of the above general formula I are those wherein

R denotes the $H_2N$ group, if $Z^1$ and $Z^3$ each denote the CO group and $R^1$ is at least disubstituted by the $H_2N$ group and an additional substituent or if $Z^2$ does not contain an imino group, or the group of formula

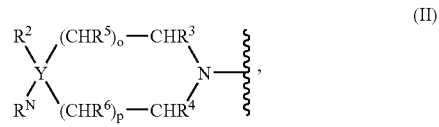

(II)

wherein
o, p, $R^5$, $R^6$ and Y are as hereinbefore defined,
$R^2$ denotes a pair of free electrons, if Y denotes the nitrogen atom, or, if Y denotes the carbon atom, R denotes the hydrogen atom or a methyl group,
$R^3$ and $R^4$ denote hydrogen atoms or together denote an alkylene bridge with 2 to 3 carbon atoms, $R^N$ denotes a monocyclic saturated, mono- or diunsaturated 5- to 7-membered aza, diaza, triaza, oxaza, thiaza, thiadiaza or S,S-dioxido-thiadiaza heterocycle containing one to two imino groups,
  wherein the abovementioned heterocycles are linked via a carbon or nitrogen atom and
  adjacent to a nitrogen atom contain a carbonyl, thioxo or iminocarbonyl group or two carbonyl groups or a carbonyl group and a thioxo or iminocarbonyl group, wherein the abovementioned iminocarbonyl groups may be substituted by a cyano group or by an alkoxycarbonyl group with 1 to 4 carbon atoms in the alkyl moiety,
  the abovementioned heterocycles containing two imino groups may be substituted at one of the imino-nitrogen atoms by an alkanoyl, hydroxycarbonylalkyl or alkoxycarbonylalkyl group with 1 to 3 carbon atoms in the alkyl moieties,
  may be substituted at one or two carbon atoms by an unbranched alkyl group, by a phenyl, phenylmethyl, naphthyl, biphenylyl or thienyl group, wherein the substituents may be identical or different,
  and wherein additionally an unbranched alkylene group with 3 to 4 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or
  an olefinic double bond of one of the abovementioned unsaturated heterocycles may be fused to a benzene, pyridine, diazine, thiophene or quinoline ring,
  with the provisos that
  (i) $R^N$ does not take on the meaning of the 2,6-dioxo-3-phenyl-3,4,5,6-tetrahydro-1H-pyrimidin-3-yl group, the 2-oxo-1,3,4,5-tetrahydro-1-imidazolyl group optionally monosubstituted by an acyl group in the 3 position and the 2(1H)-oxo-3,4,5,6-tetrahydro-1-pyrimidinyl group and
  (ii) $R^1$ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group if $R^N$ takes on the meaning of the 1,3-dihydro-2(2H)-oxobenzimidazol-1-yl, 1,3-dihydro-2(2H)-thioxobenzimidazol-1-yl, 2(1H)-oxoquinoxalin-1-yl, 3-oxo-2,3-dihydrobenzoxazin-4-yl, 3-oxo-2,3,4,5-tetrahydrobenz[f][1,4]oxazepin-4-yl or 2(1H)-oxoquinolin-3-yl group,
or, if Y denotes the carbon atom, with the proviso that
  (i) $R^1$ does not denote a 2-alkoxy-4-amino-5-bromophenyl, 2-alkoxy-4-amino-5-chlorophenyl or naphthyl group or
  (ii) $Z^2$ does not denote a group containing N or
  (iii) $Z^1$ and $Z^3$ each denote the CO group,
$R^N$ may also represent the hydroxy group
or, if Y denotes the carbon atom and $Z^1$ and $Z^3$ each denote the CO group, a benzoylaminocarbonylamino group, a phenylamino group optionally at least monosubstituted at the aniline nitrogen by an aminocarbonyl group and in the phenyl moiety,
or, if Y denotes the carbon atom, $Z^1$ and $Z^3$ each denote the CO group and in the group of general formula (II) o and p each assume the value 1, a phenylmethylamino group optionally at least monosubstituted at the benzylamine nitrogen by a $C_{1-4}$-alkoxy-carbonyl group and in the phenyl moiety, wherein the phenyl and thienyl groups contained in the groups mentioned under $R^N$ as well as benzo-, thieno-, pyrido-, diazino- and quinolino-fused heterocycles may additionally be mono-, di- or trisubstituted in the carbon skeleton by fluorine, chlorine or bromine atoms, by methyl groups, by cycloalkyl groups with 5 to 6 carbon atoms, nitro, methoxy, methylthio, methylsulphinyl, methylsulphonyl, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, [4-(1-piperidinyl)-piperidinyl]carbonyl, [4-(1-piperidinyl)piperidinyl]-carbonylamino, aminocarbonylamino, alkylaminocarbonylamino, dialkylaminocarbonylamino, aminomethyl, acetyl, cyano or trifluoromethoxy groups, wherein the substituents may be identical or different,
or, if $Z^1$—$Z^2$—$Z^3$ denotes the divalent group CO—$CH_2$—$CH_2$—CO, R may also denote the 4-[3,4-dihydro-2(1H)-oxoquinazolin-3-yl]-[1.4']bipiperidinyl-1'-yl group,
$Z^1$ denotes the methylene or carbonyl group or, if $Z^2$ denotes a divalent group of general formula III, may also denote a bond,
$Z^2$ denotes one of the groups —$(CH_2)_2$— or —$(CH_2)_3$—,
  wherein a hydrogen atom may be replaced by a $C_{1-3}$-alkyl or a hydroxy group,
one of the groups
—NH—$CH_2$,   —$CH_2$—NH,   —NH—$(CH_2)_2$—   or
—$(CH_2)_2$—NH—,
  wherein the nitrogen atoms are each linked to a carbonyl group of the groups $Z^1$ or $Z^3$ and
  the hydrogen atom of the imino group may in each case be replaced by a $C_{1-3}$-alkyl group,
the group —CH=CH— or, if $R^1$ does not denote an aromatic or heteroaromatic group substituted by cycloalkyl or phenyl groups or $R^N$ is not linked via an imino group bound in the adjacent position to a fused-on benzene ring, it also denotes a divalent group of general formula

(III)

wherein
  m and n independently of one another denote one of the numbers 1, 2 or 3 and
  the nitrogen atom is linked to the group $Z^3$ with the meaning of a carbonyl group,
$Z^3$ denotes the carbonyl group or, if $R^N$ is not linked via an imino group bound in the adjacent position to a fused-on aromatic or heteroaromatic ring, it also denotes the methylene group,
  wherein at least one of the groups $Z^1$ and $Z^3$ denotes a carbonyl group and the sequence $Z^1$—$Z^2$—$Z^3$ is at least four-membered, and $R^1$ denotes a mono-, di- or trisubstituted phenyl group, a benzimidazolyl, 1,3-dihydro-2-oxobenzimidazolyl, octahydro-9-phenanthryl or benzodioxolanyl group or, if $Z^1$ and $Z^3$ each denote the CO group, $R^1$ may also denote a 1-naphthyl or 2-naphthyl group, wherein the abovementioned aromatic and heteroaromatic groups may be mono-, di- or trisubstituted in the carbon skeleton by fluorine, chlorine, bromine or iodine atoms, by alkyl groups with 1 to 4 carbon atoms, by cycloalkyl groups with 5 to 6 carbon atoms, hydroxy, alkoxy, phenyl, trifluoromethyl, methoxycarbonyl, ethoxycarbonyl, carboxy, amino, aminomethyl, methylamino, dimethylamino, acetylamino, 4-[3-(dimethylaminopropyl)]-1-piperazinyl, piperidinyl, 4-(1-piperidinyl)-1-piperidinyl, 4-(4-methyl-1-piperazinyl)-1-piperidinyl, 4-[4-(3-dimethylaminopropyl)-1-piperazinyl]-1-piperidinyl, nitro, methanesulphonyloxy, aminocarbonyl, acetyl, cyano or trifluoromethoxy groups and the substituents may be identical or different, wherein all the abovementioned alkyl and alkoxy groups and the alkyl or alkylene moieties present inside the other groups specified may contain 1 to 5 carbon atoms unless otherwise stated, the tautomers, diastereomers, enantiomers and salts thereof.

Particularly preferred compounds of the above general formula I are those wherein R denotes the $H_2N$ group, if $Z^1$ and $Z^3$ each denote the CO group and $R^1$ is at least disubstituted by the $H_2N$ group and an additional substituent or if $Z^2$ does not contain an imino group, or the group of formula

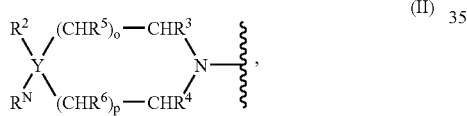

(II)

wherein
o, p and Y are as hereinbefore defined,
$R^2$ denotes a pair of free electrons, if Y denotes the nitrogen atom, or, if Y denotes the carbon atom, $R^2$ denotes the hydrogen atom or a methyl group,
$R^3$ and $R^4$ denote hydrogen atoms or together denote an alkylene bridge with 2 carbon atoms,
$R^5$ and $R^6$ denote hydrogen atoms or together denote an n-propylene bridge wherein the central methylene group may be replaced by a methylimino group,
$R^N$ denotes a monocyclic saturated, mono- or diunsaturated 5- to 7-membered aza, diaza, triaza, thiadiaza or S,S-dioxido-thiadiaza heterocycle containing one to two imino groups,
wherein the abovementioned heterocycles are linked via a carbon or nitrogen atom and
adjacent to a nitrogen atom contain a carbonyl, thioxo or iminocarbonyl group or two carbonyl groups or a carbonyl group and a thioxo or iminocarbonyl group, wherein the abovementioned iminocarbonyl groups may be substituted by a cyano group or by a tert-.butoxycarbonyl group,
the abovementioned heterocycles containing two imino groups may be substituted at one of the imino-nitrogen atoms by an acetyl, carboxymethyl or methoxycarbonyl-methyl group,
may be substituted at one or two carbon atoms by a methyl group, by a phenyl, phenylmethyl, naphthyl, biphenylyl or thienyl group, wherein the substituents may be identical or different,
and wherein additionally an unbranched alkylene group with 4 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or
an olefinic double bond of one of the abovementioned unsaturated heterocycles may be fused to a benzene, pyridine, diazine, thiophene or quinoline ring,
with the provisos that
(i) $R^N$ does not take on the meaning of the 2,6-dioxo-3-phenyl-3,4,5,6-tetrahydro-1H-pyrimidin-3-yl group, the 2-oxo-1,3,4,5-tetrahydro-1-imidazolyl group optionally monosubstituted in the 3 position by an acyl group and the 2(1H)-oxo-3,4,5,6-tetrahydro-1-pyrimidinyl group, and
(ii) $R^1$ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group, if $R^N$ takes on the meaning of the 1,3-dihydro-2(2H)-oxobenzimidazol-1-yl, 1,3-dihydro-2(2H)-thioxobenzimidazol-1-yl, 2(1H)oxoquinoxalin-1-yl, 3-oxo-2,3-dihydrobenzoxazin-4-yl, 3-oxo-2,3,4,5-tetrahydrobenz[f][1,4]oxazepin-4-yl or 2(1H)-oxoquinolin-3-yl group,
or, if Y denotes the carbon atom, with the proviso that
(i) $R^1$ does not denote a 2-alkoxy-4-amino-5-bromophenyl, 2-alkoxy-4-amino-5-chlorophenyl or naphthyl group or
(ii) $Z^2$ does not denote a group containing N, or
(iii) $Z^1$ and $Z^3$ each denote the CO group,
$R^N$ may also denote the hydroxy group,
or, if Y denotes the carbon atom and $Z^1$ and $Z^3$ each denote the CO group, a benzoylaminocarbonylamino group, a phenylamino group optionally at least monosubstituted by an aminocarbonyl group at the aniline nitrogen and in the phenyl moiety,
or, if Y denotes the carbon atom, $Z^1$ and $Z^3$ each denote the CO group and in the group of general formula (II) o and p each assume the value 1, a phenylmethylamino group optionally at least monosubstituted by a tert. butoxycarbonyl group at the benzylamine nitrogen and in the phenyl moiety,
wherein the phenyl and thienyl groups contained in the groups mentioned under $R^N$ as well as benzo-, thieno-, pyrido-, diazino- and quinolino-fused heterocycles may additionally be mono-, di- or trisubstituted in the carbon skeleton by fluorine, chlorine or bromine atoms, by methyl, nitro, methoxy, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (4-methyl-1-piperazinyl)-carbonyl, [4-(1-piperidinyl)-1-piperidinyl]carbonyl, [4-(1-piperidinyl)piperidinyl]carbonylamino, aminomethyl or aminocarbonylamino groups, wherein the substituents may be identical or different, or, if Z¹—Z²—Z³ denotes the divalent group CO—CH₂—CH₂—CO, R may also denote the 4-[3,4-dihydro-2(1H)-oxoquinazolin-3-yl]-[1.4']bipiperidinyl-1'-yl group, Z¹ denotes a methylene or carbonyl group or, if Z² denotes a divalent group of general formula III, may also denote a bond, Z² denotes one of the groups —(CH₂)₂— or —(CH₂)₃—,
wherein a hydrogen atom may be replaced by a $C_{1-3}$-alkyl or hydroxy group, one of the groups
—NH—CH₂—, —CH₂—NH— or —(CH₂)₂—NH—,
wherein the nitrogen atoms are each linked to a carbonyl group of the groups Z¹ or Z³ and
the hydrogen atom of the imino group may be replaced by a $C_{1-3}$-alkyl group in each case, the group —CH=CH— or, if R¹ does not denote an aromatic or heteroaromatic group substituted by cycloalkyl or phenyl groups or $R^N$ is not linked via an imino group bound in the adjacent position to a fused-on benzene ring, it may also denote a divalent group of general formula

(III)

wherein
m denotes one of the numbers 1 or 2 and n denotes one of the numbers 1, 2 or 3 and the nitrogen atom is linked to the group Z³ with the meaning of a carbonyl group, Z³ denotes the carbonyl group or, if $R^N$ is not linked via an imino group bound in the adjacent position to a fused-on aromatic or heteroaromatic ring, it may also denote the methylene group,
wherein at least one of the groups Z¹ and Z³ denotes a carbonyl group and the sequence Z¹—Z²—Z³ is at least four-membered, and R¹ denotes a monosubstituted phenyl group, a 5-benzimidazolyl, 1,3-dihydro-2-oxobenzimidazol-5-yl, octahydro-9-phenanthryl or 5-benzodioxolanyl group or, if Z¹ and Z³ each denote the CO group, it may also denote a 1-naphthyl or 2-naphthyl group,
wherein the abovementioned aromatic and heteroaromatic groups may additionally be mono-, di- or trisubstituted in the carbon skeleton by fluorine, chlorine, bromine or iodine atoms, by alkyl groups with 1 to 4 carbon atoms, by cyclohexyl, hydroxy, alkoxy groups with up to 3 carbon atoms in the alkyl moiety, phenyl, trifluoromethyl, methoxycarbonyl, ethoxycarbonyl, carboxy, amino, aminomethyl, methylamino, dimethylamino, acetylamino, 4-[3-(dimethylaminopropyl)-1-piperazinyl, piperidinyl, 4-(1-piperidinyl)-1-piperidinyl, 4-(4-methyl-1-piperazinyl)-1-piperidinyl, 4-[4-(3-dimethylaminopropyl)-1-piperazinyl]-1-piperidinyl, nitro, cyano or trifluoromethoxy groups and the substituents may be identical or different, the tautomers, diastereomers, enantiomers and salts thereof.
Most particularly preferred compounds of the above general formula I are those wherein R denotes the H₂N group, if Z¹ and Z³ each denote the CO group and R¹ is at least disubstituted by the H₂N group and an additional substituent or if Z² does not contain an imino group, or R denotes the group of formula

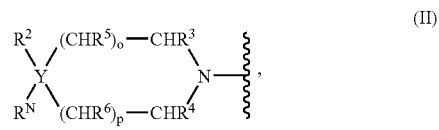

(II)

wherein
Y denotes the carbon atom and o and p independently of one another denote the numbers 1 or 0 or
Y denotes the nitrogen atom and o and p each represent the number 1,
R² denotes a pair of free electrons, if Y denotes the nitrogen atom, or, if Y denotes the carbon atom, R² denotes the hydrogen atom or the methyl group,
R³ and R⁴ denote hydrogen atoms or together denote an ethylene bridge,
R⁵ and R⁶ denote hydrogen atoms or together denote a —CH₂—N(CH₃)—CH₂— bridge,
$R^N$ denotes a 3,4-dihydro-2(1H)-oxoquinazolin-3-yl, 3,4-dihydro-2(1H)-oxoquinazolin-1-yl, 1,3-dihydro-4-phenyl-2H-2-oxoimidazol-1-yl, 3,4-dihydro-2(1H)-oxopyrido-[2,3-d]pyrimidin-3-yl, 4-phenyl-1,3,4,5-tetrahydro-2H-2-oxoimidazol-1-yl, 1,3-dihydro-5-methyl-4-phenyl-2H-2-oxoimidazol-1-yl, 3,4-dihydro-2(1H)-oxothieno[3,4-d]pyrimidin-3-yl, 1,3-dihydro-4-(3-thienyl)-2H-2-oxoimidazol-1-yl, 2,4-dihydro-5-phenyl-3(3H)-oxo-1,2,4-triazol-2-yl, 3,4-dihydro-2(1H)-oxothieno[3,2-d]pyrimidin-3-yl, 3,4-dihydro-2(1H)-oxopyrido[3,4-d]pyrimidin-3-yl, 3,4-dihydro-2(1H)-oxopyrido[4,3-d]pyrimidin-3-yl, 3,4-dihydro-2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2(2H)-oxoimidazo[4,5-d]pyrimidin-3-yl, 3,4,4a,5,6,7,8,8a-octahydro-2(1H)-oxoquinazolin-3-yl, 2,5-dioxo-4-(phenylmethyl)-imidazolidin-1-yl, 2,5-dioxo-4-phenyl-imidazolidin-1-yl, 3,4-dihydro-2,2-dioxido-2,1,3-benzothiadiazin-3-yl, 1,3-dihydro-4-(2-naphthyl)-2H-2-oxoimidazol-1-yl, 4-(4-biphenylyl)-1,3-dihydro-2H-2-oxoimidazol-1-yl, 1,3-dihydro-2(2H)-oxoimidazo[4,5-c]quinolin-3-yl, 2-(dimethylethoxycarbonylamino)-3,4-dihydroquinazolin-3-yl, 2-amino-3,4-dihydroquinazolin-3-yl, 3,4-dihydro-2(1H)-thioxoquinazolin-3-yl, 3,4-dihydro-2(1H)-cyanoiminoquinazolin-3-yl, 2,3,4,5-tetrahydro-2(1H)-oxo-1,3-benzodiazepin-3-yl or 2,4(1H,3H)-dioxoquinazolin-3-yl group or,
if R¹ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group, may also denote a 1,3-dihydro-2 (2H)-oxobenzimidazol-1-yl or 2(1H)-oxoquinolin-3-yl group,
wherein the abovementioned mono- and bicyclic heterocycles containing two imino groups may be substituted at one of the imino-nitrogen atoms by an acetyl, carboxymethyl or methoxycarbonylmethyl group and/or
may additionally be mono-, di- or trisubstituted in the carbon skeleton and/or at the phenyl groups contained in these groups by fluorine, chlorine or bromine atoms, by methyl groups, nitro, methoxy, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (4-methyl-1-piperazinyl)carbonyl, [4-(1-piperidinyl)-1-piperidinyl]carbonyl, [4-(1-piperidinyl) piperidinyl]-carbonylamino or aminocarbonylamino groups, wherein the substituents may be identical or different and multiple substitution with the last six substituents is excluded, or, if Y denotes the carbon atom, with the proviso that
(i) $R^1$ does not denote a 2-alkoxy-4-amino-5-bromophenyl, 2-alkoxy-4-amino-5-chlorophenyl or naphthyl group or
(ii) $Z^2$ does not denote a group containing N,
$R^N$ may also denote the hydroxy group, or, if Y denotes the carbon atom and $Z^1$ and $Z^3$ each denote the CO group, a benzoylaminocarbonylamino group, a phenylamino group optionally at least monosubstituted by an aminocarbonyl group at the aniline nitrogen and in the phenyl moiety or, if Y denotes the carbon atom, $Z^1$ and $Z^3$ each denote the CO group and in the group of general formula (II) o and p each assume the value 1, a phenylmethylamino group optionally at least monosubstituted by a tert. butoxycarbonyl group at the benzylamine nitrogen and in the phenyl moiety, or, if $Z^1$—$Z^2$—$Z^3$ denotes the divalent group CO—$CH_2$—$CH_2$—CO, R may also denote the 4-[3,4-dihydro-2(1H)-oxoquinazolin-3-yl]-[1.4']bipiperidinyl-1'-yl group, $Z^1$ denotes the methylene or carbonyl group or, if $Z^2$ denotes a divalent group of general formula III, may also denote a bond, $Z^2$ denotes one of the groups —$(CH_2)_2$— or —$(CH_2)_3$—,
wherein a hydrogen atom may be replaced by a methyl or hydroxy group, one of the groups —NH—$CH_2$, —$CH_2$—NH— or —$(CH_2)_2$—NH—,
wherein the nitrogen atoms are each linked to a carbonyl group of the groups $Z^1$ or $Z^3$ and
the hydrogen atom of the imino group may be replaced in each case by the methyl group, the group —CH=CH— or, if $R^1$ does not represent an aromatic or heteroaromatic group substituted by cycloalkyl or phenyl groups or $R^N$ is not linked via an imino group bound in the adjacent position to a fused-on benzene ring, it also denotes a divalent group of general formula

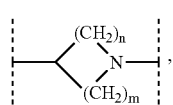

(III)

wherein
m denotes one of the numbers 1 or 2 and n denotes one of the numbers 1, 2 or 3 and the nitrogen atom is linked to the group $Z^3$ with the meaning of a carbonyl group, $Z^3$ denotes the carbonyl group or, if $R^N$ is not linked via an imino group bound in the adjacent position to a fused-on aromatic or heteroaromatic ring, it also denotes the methylene group, wherein at least one of the groups $Z^1$ and $Z^3$ denotes the carbonyl group and the sequence $Z^1$—$Z^2$—$Z^3$ is at least four-membered, and $R^1$ is as hereinbefore defined under the particularly preferred compounds, the tautomers, diastereomers, enantiomers and salts thereof.
The following are listed as examples of most particularly preferred compounds:
(1)  1-{1-[4-(4-amino-3,5-dibromophenyl)-4-oxobutyl]-4-piperidinyl}-1,3-dihydro-2(2H)-benzimidazolone
(2)  1-{1-[4-(4-amino-3,5-dibromophenyl)-4-oxobutyl]-4-piperidinyl}-1,3-dihydro-6-methyl-2(2H)-benzimidazolone
(3)  1-{1-[4-(4-amino-3,5-dibromophenyl)-4-oxobutyl]-4-piperidinyl}-1,3-dihydro-5-methyl-2(2H)-benzimidazolone
(4)  1-{1-[4-(4-amino-3,5-dibromophenyl)-4-oxobutyl]-4-piperidinyl}-1,3-dihydro-5-nitro-2(2H)-benzimidazolone
(5)  5-amino-1-{1-[4-(4-amino-3,5-dibromophenyl)-4-oxobutyl]-4-piperidinyl}-1,3-dihydro-2(2H)-benzimidazolone
(6) 5-acetylamino-1-{1-[4-(4-amino-3,5-dibromophenyl)-4-oxobutyl]-4-piperidinyl}-1,3-dihydro-2(2H)-benzimidazolone
(7)  3-acetyl-5-acetylamino-1-{1-[4-(4-amino-3,5-dibromophenyl)-4-oxobutyl]-4-piperidinyl}-1,3-dihydro-2 (2H)-benzimidazolone
(8)  1-{1-[4-(4-amino-3,5-dibromophenyl)-4-oxobutyl]-4-piperidinyl}-5-cyclohexanecarbonylamino-1,3-dihydro-2 (2H)-benzimidazolone
(9)  5-aminocarbonylamino-1-{1-[4-(4-amino-3,5-dibromophenyl)-4-oxobutyl]-4-piperidinyl}-1,3-dihydro-2 (2H)-benzimidazolone
(10) 3-{1-[4-(4-amino-3,5-dibromophenyl)-4-oxobutyl]-4-piperidinyl}-3,4-dihydro-2(1H)-quinazolinone
(11)  1-{1-[4-(4-amino-3,5-dibromophenyl)-4-oxobutyl]-4-piperidinyl}-3,4-dihydro-2(1H)-quinazolinone
(12)  1-{1-[4-(4-amino-3,5-dibromophenyl)-1,4-dioxobutyl]-4-piperidinyl}-1,3-dihydro-4-phenyl-2(2H)-imidazolone
(13)  3-{1-[4-(4-amino-3,5-dibromophenyl)-1,4-dioxobutyl]-4-piperidinyl}-3,4-dihydro-2(1H)-pyrido[2,3-d]pyrimidinone
(14)  1-{1-[4-(4-amino-3,5-dibromophenyl)-1,4-dioxobutyl]-4-piperidinyl}-4-phenyl-1,3,4,5-tetrahydro-2(2H)-imidazolone
(15)  1-{1-[4-(4-amino-3,5-dibromophenyl)-1,4-dioxobutyl]-4-piperidinyl}-1,3-dihydro-5-methyl-4-phenyl-2 (2H)-imidazolone
(16)  3-{1-[4-(4-amino-3,5-dibromophenyl)-1,4-dioxobutyl]-4-piperidinyl}-3,4-dihydro-8-methyl-2(1H)-quinazolinone
(17) 3-{1-[4-(4-acetylamino-3-bromophenyl)-1,4-dioxobutyl]-4-piperidinyl}-3,4-dihydro-8-methyl-2(1H)-quinazolinone
(18) 3-{1-[4-(4-acetylamino-3-bromophenyl)-1,4-dioxobutyl]-4-piperidinyl}-3,4-dihydro-2(1H)-quinazolinone
(19) 1-{1-[4-(4-acetylamino-3-bromophenyl)-1,4-dioxobutyl]-4-piperidinyl}-1,3-dihydro-2(2H)-benzimidazolone
(20) 1-{1-[4-(4-amino-3-bromophenyl)-1,4-dioxobutyl]-4-piperidinyl}-1,3-dihydro-2(2H)-benzimidazolone
(21) 1-{1-[4-(4-acetylamino-3-bromophenyl)-1,4-dioxobutyl]-4-piperidinyl}-1,3-dihydro-4-phenyl-2(2H)-imidazolone
(22) 3-{1-[4-(4-amino-3-bromophenyl)-1,4-dioxobutyl]-4-piperidinyl}-3,4-dihydro-2(1H)-quinazolinone

(23) 3-{1-[4-(4-amino-3-bromophenyl)-1,4-dioxobutyl]-4-piperidinyl}-3,4-dihydro-8-methyl-2(1H)-quinazolinone
(24) 1-{1-[4-(4-amino-3-bromophenyl)-1,4-dioxobutyl]-4-piperidinyl}-1,3-dihydro-4-phenyl-2(2H)-imidazolone
(25) 3,4-dihydro-3-{1-[1,4-dioxo-4-(4-methoxyphenyl)butyl]-4-piperidinyl}-2(1H)-quinazolinone
(26) 3,4-dihydro-3-{1-[4-(4-chlorophenyl)-1,4-dioxobutyl]-4-piperidinyl}-2(1H)-quinazolinone
(27) 3,4-dihydro-3-{1-[1,4-dioxo-4-(4-methylamino-3-nitrophenyl)butyl]-4-piperidinyl}-2(1H)-quinazolinone
(28) 3,4-dihydro-3-{1-[4-(4-chloro-3-nitrophenyl)-1,4-dioxo-butyl]-4-piperidinyl}-2(1H)-quinazolinone
(29) 3-{1-[4-(4-amino-3,5-dibromophenyl)-1,4-dioxobutyl]-4-piperidinyl}-3,4-dihydro-6,7-dimethoxy-2(1H)-quinazolinone
(30) 3-{1-[4-(1H-benzimidazol-5-yl)-1,4-dioxobutyl]-4-piperidinyl}-3,4-dihydro-2(1H)-quinazolinone
(31) 3-{1-[4-(1,3-dihydro-2(2H)-oxobenzimidazol-5-yl)-1,4-dioxobutyl]-4-piperidinyl}-3,4-dihydro-2(1H)-quinazolinone
(32) (R,S)-3-{1-[4-(4-amino-3,5-dibromophenyl)-1,4-dioxobutyl]-3-pyrrolidinyl}-3,4-dihydro-2(1H)-quinazolinone
(33) 3-{1-[4-(4-amino-3,5-dibromophenyl)-1,4-dioxobutyl]-4-piperidinyl}-3,4-dihydro-8-methoxy-2(1H)-quinazolinone
(34) 3-{1-[4-(4-amino-3,5-dibromophenyl)-1,4-dioxobutyl]-4-piperidinyl}-5-chloro-3,4-dihydro-2(1H)-quinazolinone
(35) 3-{1-[4-(3-amino-4-chlorophenyl)-1,4-dioxobutyl]-4-piperidinyl}-3,4-dihydro-2(1H)-quinazolinone
(36) 3-{1-[4-(4-amino-3,5-dibromophenyl)-1,4-dioxobutyl]-4-piperidinyl}-3,4-dihydro-2(1H)-thieno[3,4-d]pyrimidinone
(37) 1-{1-[4-(4-amino-3,5-dibromophenyl)-1,4-dioxobutyl]-4-piperidinyl}-1,3-dihydro-4-(3-trifluoromethylphenyl)-2(2H)-imidazolone
(38) 1-{1-[4-(4-amino-3,5-dibromophenyl)-1,4-dioxobutyl]-4-piperidinyl}-1,3-dihydro-4-(3-thienyl)-2(2H)-imidazolone
(39) 2-{1-[4-(4-amino-3,5-dibromophenyl)-1,4-dioxobutyl]-4-piperidinyl}-2,4-dihydro-5-phenyl-3(3H)-1,2,4-triazolone
(40) 3-{1-[4-(4-amino-3,5-dibromophenyl)-1,4-dioxobutyl]-4-piperidinyl}-3,4-dihydro-2(1H)-thieno[3,2-d]pyrimidinone
(41) 1-{1-[4-(4-amino-3,5-dibromophenyl)-1,4-dioxobutyl]-4-piperidinyl}-1,3-dihydro-4-(4-trifluoromethylphenyl)-2(2H)-imidazolone
(42) 3-{1-[4-(4-amino-3,5-dibromophenyl)-1,4-dioxobutyl]-4-piperidinyl}-3,4-dihydro-2(1H)-pyrido[3,4-d]pyrimidinone
(43) 3-{1-[4-(4-amino-3,5-dibromophenyl)-1,4-dioxobutyl]-4-piperidinyl}-3,4-dihydro-2(1H)-pyrido[4,3-d]pyrimidinone
(44) 3-{1-[4-(4-amino-3,5-dibromophenyl)-1,4-dioxobutyl]-4-piperidinyl}-3,4-dihydro-6-hydroxy-2(1H)-quinazolinone
(45) (E)-3-{1-[4-(4-bromophenyl)-1,4-dioxo-2-buten-1-yl]-4-piperidinyl}-3,4-dihydro-2(1H)-quinazolinone
(46) (E)-3,4-dihydro-3-{1-[4-(3,4-dimethylphenyl)-1,4-dioxo-2-buten-1-yl]-4-piperidinyl}-2(1H)-quinazolinone
(47) (E)-3,4-dihydro-3-{1-[[1,4-dioxo-4-(4-hydroxyphenyl)-2-buten-1-yl]-4-piperidinyl}-2(1H)-quinazolinone
(48) (E)-3,4-dihydro-3-{1-[1,4-dioxo-4-(1-naphthyl)-2-buten-1-yl]-4-piperidinyl}-2(1H)-quinazolinone
(49) (E)-3,4-dihydro-3-{1-[4-4-(1,1-dimethylethyl)phenyl]-1,4-dioxo-2-buten-1-yl]-4-piperidinyl}-2(1H)-quinazolinone
(50) (E)-3-{1-[4-(3,4-dichlorophenyl)-1,4-dioxo-2-buten-1-yl]-4-piperidinyl}-3,4-dihydro-2(1H)-quinazolinone
(51) (E)-3,4-dihydro-3-{1-[1,4-dioxo-4-(3-nitrophenyl)-2-buten-1-yl]-4-piperidinyl}-2(1H)-quinazolinone
(52) (E)-3,4-dihydro-3-{1-[1,4-dioxo-4-(3-methylphenyl)-2-buten-1-yl]-4-piperidinyl}-2(1H)-quinazolinone
(53) (E)-3,4-dihydro-3-{1-[4-(4-cyclohexylphenyl)-1,4-dioxo-2-buten-1-yl]-4-piperidinyl}-2(1H)-quinazolinone
(54) (E)-3-{1-[4-[3,5-bis-(1,1-dimethylethyl)-4-hydroxyphenyl]-1,4-dioxo-2-buten-1-yl]-4-piperidinyl}-3,4-dihydro-2(1H)-quinazolinone
(55) (E)-3-{1-[4-(4-chloro-3-methylphenyl)-1,4-dioxo-2-buten-1-yl]-4-piperidinyl}-3,4-dihydro-2(1H)-quinazolinone
(56) (E)-3-{1-[4-(3-bromo-4-nitrophenyl)-1,4-dioxo-2-buten-1-yl]-4-piperidinyl}-3,4-dihydro-2(1H)-quinazolinone
(57) (E)-3-{1-[4-(3-bromophenyl)-1,4-dioxo-2-buten-1-yl]-4-piperidinyl}-3,4-dihydro-2(1H)-quinazolinone
(58) 4-amino-3,5-dibromo-N-{2-[4-(1,3-dihydro-2(2H)-oxo-1-benzimidazolyl)-1-piperidinyl]ethyl}-benzamide
(59) 3-{1-[4-(4-amino-3,5-dibromophenyl)-1,4-dioxobutyl]-4-piperazinyl}-2(1H)-quinolinone
(60) 3-{1-[4-(4-amino-3,5-dibromophenyl)-1-oxobutyl]-4-piperidinyl}-3,4-dihydro-2(1H)-quinazolinone
(61) 3-{1-[4-(4-amino-3,5-dibromophenyl)-1,4-dioxobutyl]-4-piperazinyl}-2(1H)-quinoxalinone
(62) 3-{1-[4-(4-biphenylyl)-1,4-dioxobutyl]-4-piperidinyl}-3,4-dihydro-2(1H)-quinazolinone
(63) 1-{1-[4-(4-amino-3,5-dibromophenyl)-1,4-dioxobutyl]-4-piperidinyl}-1-(4-fluorophenyl)-urea
(64) 1-{1-[4-(4-amino-3,5-dibromophenyl)-1-oxobutyl]-4-piperidinyl}-1,3-dihydro-4-phenyl-2(2H)-imidazolone
(65) 3-{1-[4-(3,5-dibromophenyl)-1,4-dioxobutyl]-4-piperidinyl}-3,4-dihydro-2(1H)-quinazolinone
(66) 3-{1-[1,4-dioxo-4-(2-methoxyphenyl)butyl]-4-piperidinyl}-3,4-dihydro-2(1H)-quinazolinone
(67) 3-{1-[1,4-dioxo-4-(4-fluorophenyl)butyl]-4-piperidinyl}-3,4-dihydro-2(1H)-quinazolinone
(68) 1-{1-[4-(4-amino-3,5-dibromophenyl)-1,4-dioxobutyl]-4-methyl-4-piperidinyl}-1,3-dihydro-2(2H)-benzimidazolone
(69) 3-{1-[4-(4-acetylamino-3-bromophenyl)-1-oxobutyl]-4-piperidinyl}-3,4-dihydro-2(1H)-quinazolinone
(70) 3-{1-[4-(4-amino-3-bromophenyl)-1-oxobutyl]-4-piperidinyl}-3,4-dihydro-2(1H)-quinazolinone
(71) (E)-3-{1-[4-(4-cyanophenyl)-1,4-dioxo-2-buten-1-yl]-4-piperidinyl}-3,4-dihydro-2(1H)-quinazolinone
(72) 3-{1-[4-(4-cyanophenyl)-1,4-dioxobutyl]-4-piperidinyl}-3,4-dihydro-2(1H)-quinazolinone
(73) (R,S)-3-{1-[4-(4-amino-3-cyano-5-fluorophenyl)-1,4-dioxo-2-hydroxybutyl]-4-piperidinyl}-3,4-dihydro-2(1H)-quinazolinone
(74) (E)-3-{1-[4-(4-amino-3-cyano-5-fluorophenyl)-1,4-dioxo-2-buten-1-yl]-4-piperidinyl}-3,4-dihydro-2(1H)-quinazolinone
(75) 3-{1-[4-(4-amino-3-cyano-5-fluorophenyl)-1,4-dioxobutyl]-4-piperidinyl}-3,4-dihydro-2(1H)-quinazolinone
(76) 3-{1-[4-(4-aminomethyl)phenyl)-1-oxobutyl]-4-piperidinyl}-3,4-dihydro-2(1H)-quinazolinone
(77) 1-{1-[4-(4-amino-3-cyano-5-fluorophenyl)-1,4-dioxobutyl]-4-piperidinyl}-1,3-dihydro-4-phenyl-2(2H)-imidazolone

(78) 2-{1-[4-(4-amino-3,5-dibromophenyl)-1,4-dioxobutyl]-4-piperidinyl}-1,1-dioxido-1,2,4-benzothiadiazin-3(4H)-one
(79) 3-{1'-[4-(4-amino-3,5-dibromophenyl)-1,4-dioxobutyl]-[1.4']bipiperidinyl-4-yl}-3,4-dihydro-2(1H)-quinazolinone
(80) 1-[4-(4-amino-3,5-dibromophenyl)-1,4-dioxobutyl]-4-hydroxypiperidine
(81) 3-[1'-(4-amino-3,5-dibromobenzoyl)-[1.4']bipiperidinyl-4-yl]-3,4-dihydro-2(1H)-quinazolinone
(82) (E)-3-{1-[4-(4-amino-3,5-dibromophenyl)-1,4-dioxo-2-buten-1-yl]-4-piperidinyl}-3,4-dihydro-2(1H)-quinazolinone
(83) (E)-1-{1-[4-(4-amino-3,5-dibromophenyl)-1,4-dioxo-2-buten-1-yl]-4-piperidinyl}-1,3-dihydro-4-phenyl-2(2H)-imidazolone
(84) (E)-4-amino-3,5-dibromo-γ-oxobenzenebutenoic acid amide
(85) 3-{1-[4-(4-amino-3,5-dibromophenyl)-1,4-dioxobutyl]-4-piperidinyl}-2(1H)-quinolinone
(86) (R,S)-3-{1-[4-(4-amino-3,5-dibromophenyl)-1,4-dioxobutyl]-4-piperidinyl}-3,4-dihydro-2(1H)-quinolinone
(87) 1-(4-amino-3,5-dibromobenzoyl)-3-{[4-(3,4-dihydro-2(1H)-oxoquinazolin-3-yl)-1-piperidinyl]carbonyl}-azetidine
(88) 1-(3,5-dibromo-4-hydroxybenzoyl)-3-{[4-(3,4-dihydro-2(1H)-oxoquinazolin-3-yl)-1-piperidinyl]carbonyl}-azetidine
(89) 3-[1'-(4-amino-3,5-dibromobenzoyl)-[1.4']bipiperidinyl-4-yl]-2,4(1H,3H)-quinazolinedione
(90) 1-[1'-(4-amino-3,5-dibromobenzoyl)-[1.4']bipiperidinyl-4-yl]-1,3-dihydro-4-phenyl-2(2H)-imidazolone
(91) 3-[1'-(3,5-dibromo-4-hydroxybenzoyl)-[1.4']bipiperidinyl-4-yl]-3,4-dihydro-2(1H)-quinazolinone
(92) 3-[1'-(3,5-dibromo-4-hydroxybenzoyl)-[1.4']bipiperidinyl-4-yl]-2,4(1H,3H)-quinazolinedione:
(93) 1-[1'-(3,5-dibromo-4-hydroxybenzoyl)-[1.4']bipiperidinyl-4-yl]-1,3-dihydro-4-phenyl-2(2H)-imidazolone
(94) 1-[1'-(4-amino-3,5-dibromobenzoyl)-[1.4']bipiperidinyl-4-yl]-1,3-dihydro-4-(3-trifluoromethylphenyl)-2(2H)-imidazolone
(95) 1-[1'-(4-amino-3,5-dibromobenzoyl)-[1.41]bipiperidinyl-4-yl]-1,3-dihydro-5-hydroxy-4-(3-trifluoromethylphenyl)-2(2H)-imidazolone
(96) 1'-(4-amino-3,5-dibromobenzoyl)-4-{[[(3-trifluoromethyl-benzoyl)amino]carbonyl]amino}-[1.4']bipiperidinyl
(97) 1-[1'-(3,5-dibromo-4-hydroxybenzoyl)-[1.4']bipiperidinyl-4-yl]-1,3-dihydro-4-(3-trifluoromethylphenyl)-2(2H)-imidazolone
(98) 1-(4-amino-3,5-dibromobenzoyl)-3-[4-(3,4-dihydro-2(1H)-oxoquinazolin-3-yl)-1-piperidinyl]-azetidine
(99) 3-{1-[4-(4-amino-3,5-dibromophenyl)-1,4-dioxobutyl]-3-azetidinyl}-3,4-dihydro-2(1H)-quinolinone
(100) 1-{1-[4-(4-amino-3,5-dibromophenyl)-1,4-dioxobutyl]-4-piperidinyl}-4-(4-amino-3,5-dibromophenyl)-1,3-dihydro-2(2H)-imidazolone
(101) 3,4-dihydro-3-{1-[4-(3-fluoro-4-methoxyphenyl)-1,4-dioxo-butyl]-4-piperidinyl}-2(1H)-quinazolinone
(102) 3-{1-[4-(3,5-dibromo-4-methylphenyl)-1,4-dioxobutyl]-4-piperidinyl}-3,4-dihydro-2(1H)-quinazolinone
(103) (E)-3-{1-[4-[3-chloro-4-(dimethylamino)phenyl]-1,4-dioxo-2-buten-1-yl]-4-piperidinyl}-3,4-dihydro-2(1H)-quinazolinone
(104) 3-{1-[4-[3-chloro-4-(dimethylamino)phenyl]-1,4-dioxo-butyl]-4-piperidinyl}-3,4-dihydro-2(1H)-quinazolinone
(105) 3-{1-[4-[3-chloro-4-[4-(3-dimethylaminopropyl)-1-piperazinyl]phenyl]-1,4-dioxobutyl]-4-piperidinyl}-3,4-dihydro-2(1H)-quinazolinone
(106) 3-{1-[4-[3-bromo-4-[[1.4']bipiperidinyl-1'-yl]phenyl]-1,4-dioxobutyl]-4-piperidinyl}-3,4-dihydro-2(1H)-quinazolinone
(107) 3-{1-[4-[3-bromo-4-[4-(4-methyl-1-piperazinyl)-1-piperidinyl]phenyl]-1,4-dioxobutyl]-4-piperidinyl}-3,4-dihydro-2(1H)-quinazolinone
(108) 3-{1-[4-[3-bromo-4-[4-(3-dimethylaminopropyl)-1-piperazinyl]phenyl]-1,4-dioxobutyl]-4-piperidinyl}-3,4-dihydro-2(1H)-quinazolinone
(19) N-[2-(4-amino-3,5-dibromophenyl)-2-oxoethyl]-N-methyl-4-(3,4-dihydro-2(1H)-oxoquinazolin-3-yl)-piperidine-1-carboxamide
(110) 3-{1-[4-[3,5-dibromo-4-[4-(4-methyl-1-piperazinyl)-1-piperidinyl]phenyl]-1,4-dioxobutyl]-4-piperidinyl}-3,4-dihydro-2(1H)-quinazolinone
(111) 3-{1-[4-[3,5-dibromo-4-[4-[4-(3-dimethylaminopropyl)-1-piperazinyl]-1-piperidinyl]phenyl]-1,4-dioxobutyl]-4-piperidinyl}-3,4-dihydro-2(1H)-quinazolinone
(112) 1-{1-[4-(4-amino-3,5-dibromophenyl)-4-oxobutyl]-4-piperidinyl}-1,3-dihydro-3-methoxycarbonylmethyl-2(2H)-benzimidazolone
(113) 1-{1-[4-(4-amino-3,5-dibromophenyl)-4-oxobutyl]-4-piperidinyl}-1,3-dihydro-3-carboxymethyl-2(2H)-benzimidazolone
(114) 1-{1-[4-(4-amino-3,5-dibromophenyl)-1,4-dioxobutyl]-4-piperidinyl}-1,3-dihydro-2(2H)-benzimidazolone
(115) 3-{1-[4-(4-amino-3,5-dibromophenyl)-1,4-dioxobutyl]-4-piperidinyl}-3,4-dihydro-2(1H)-quinazolinone
(116) 3-{1-[4-(4-amino-3,5-dibromophenyl)-1,4-dioxobutyl]-4-piperidinyl}-1,3-dihydro-7-hydroxy-2(2H)-imidazo[4,5-d]-pyrimidinone
(117) methyl 3-{1-[4-(4-amino-3,5-dibromophenyl)-1,4-dioxobutyl]-4-piperidinyl}-3,4-dihydro-2(1H)-oxoquinazolin-7-carboxylate
(118) 3-{1-[4-(4-amino-3,5-dibromophenyl)-1,4-dioxobutyl]-4-piperidinyl}-3,4-dihydro-2(1H)-oxoquinazolin-7-carboxylic acid
(119) 1-[4-(4-amino-3,5-dibromophenyl)-1,4-dioxobutyl]-4-(2-aminocarbonylaminobenzeneamino)-piperidine
(120) 3-{1-[4-(4-amino-3,5-dibromophenyl)-1,4-dioxobutyl]-4-<piperidinyl}-3,4-dihydro-2(1H)-oxoquinazolin-7-carboxamide
(121) 3-{1-[4-(4-amino-3,5-dibromophenyl)-1,4-dioxobutyl]-4-piperidinyl}-3,4-dihydro-7-[(4-methyl-1-piperazinyl)carbonyl]-2(1H)-quinazolinone
(122) 3-{1-[4-(4-amino-3,5-dibromophenyl)-1,4-dioxobutyl]-4-piperidinyl}-3,4-dihydro-7-[(4-morpholinyl)carbonyl]-2(1H)-quinazolinone
(123) 3-{1-[4-(4-amino-3,5-dibromophenyl)-1,4-dioxobutyl]-4-piperidinyl}-3,4-dihydro-N-(2-hydroxyethyl)-2(1H)-oxoquinazolin-7-carboxamide
(124) 1-[4-(4-amino-3,5-dibromophenyl)-1,4-dioxobutyl]-4-(2-methanesulphonylaminobenzeneamino)-piperidine
(125) N-[2-(4-amino-3,5-dibromophenyl)-2-oxoethyl]-4-(3,4-dihydro-2(1H)-oxoquinazolin-3-yl)-piperidine-1-carboxamide
(126) 4-amino-3,5-dibromo-N-{3-[4-(1,3-dihydro-2(2H)-oxo-1-benzimidazolyl)-1-piperidinyl]-3-oxopropyl}-benzamide
(127) 4-amino-3,5-dibromo-N-{3-[4-(3,4-dihydro-2(1H)-oxoquinazolin-3-yl)-1-piperidinyl]-3-oxopropyl}-benzamide (128) 4-amino-3,5-dibromo-N-{2-[4-(1,3-dihydro-2(2H)-oxo-1-benzimidazolyl)-1-piperidinyl]-2-oxoethyl}-benzamide
(129) 4-amino-3,5-dibromo-N-{2-[4-(3,4-dihydro-2(1H)-oxoquinazolin-3-yl)-1-piperidinyl]-2-oxoethyl}-benzamide
(130) 4-amino-3,5-dibromo-N-{2-[4-(1,3-dihydro-4-phenyl-2(2H)-oxo-imidazol-1-yl)-1-piperidinyl]-2-oxoethyl}-benzamide
(131) 1-[4-(4-amino-3,5-dibromophenyl)-1,4-dioxobutyl]-N-(1,1-dimethylethoxycarbonyl)-N-[(2-aminocarbonylaminophenyl)methyl]-4-piperidineamine
(132) 3-{1-[4-(4-acetylamino-3,5-dibromophenyl)-1,4-dioxobutyl]-4-piperidinyl}-3,4-dihydro-2(1H)-quinazolinone
(133) 1-[4-(4-amino-3,5-dibromophenyl)-1,4-dioxobutyl]-N-[(2-aminocarbonylaminophenyl)methyl]-4-piperidineamine
(134) 1-[4-(4-amino-3,5-dibromophenyl)-1,4-dioxobutyl]-N-[(2-methanesulphonylaminophenyl)methyl]-4-piperidineamine
(135) 4-amino-3,5-dibromo-N-{3-[4-(1,3-dihydro-4-phenyl-2(2H)-oxo-imidazol-1-yl)-1-piperidinyl]-3-oxopropyl}-benzamide
(136) 4-amino-3,5-dibromo-N-{2-[4-(1,3-dihydro-2(2H)-oxo-1-benzimidazolyl)-1-piperidinyl]-2-oxoethyl}-N-methyl-benzamide
(137) 4-amino-3,5-dibromo-N-{2-[4-(3,4-dihydro-2(1H)-oxoquinazolin-3-yl)-1-piperidinyl]-2-oxoethyl}-N-methyl-benzamide
(138) 3-{1-[4-(4-amino-3,5-dibromophenyl)-1,4-dioxobutyl]-4-piperidinyl}-3,4,4a,5,6,7,8,8a-octahydro-2(1H)-quinazolinone
(139) N-{2-[4-(3,4-dihydro-2(1H)-oxoquinazolin-3-yl)-1-piperidinyl]-2-oxoethyl}-2-naphthalenecarboxamide
(140) N-{2-[4-(3,4-dihydro-2(1H)-oxoquinazolin-3-yl)-1-piperidinyl]-2-oxoethyl}-1-naphthalenecarboxamide
(141) 4-amino-3-chloro-N-{2-[4-(1,3-dihydro-2(2H)-oxo-1-benzimidazolyl)-1-piperidinyl]ethyl}-5-trifluoromethylbenzamide
(142) 1,3-dihydro-1-{1-[4-(2-naphthyl)-1,4-dioxobutyl]-4-piperidinyl}-2(2H)-benzimidazolone
(143) 3,4-dihydro-3-{1-[4-(2-naphthyl)-1,4-dioxobutyl]-4-piperidinyl}-2(1H)-quinazolinone
(144) 1,3-dihydro-1-{1-[4-(1-naphthyl)-1,4-dioxobutyl]-4-piperidinyl}-2(2H)-benzimidazolone
(145) 3,4-dihydro-3-{1-[4-(1-naphthyl)-1,4-dioxobutyl]-4-piperidinyl}-2(1H)-quinazolinone
(146) (R,S)-3-{1-[4-(4-amino-3,5-dibromophenyl)-1,4-dioxo-2-methylbutyl]-4-piperidinyl}-3,4-dihydro-2(1H)-quinazolinone
(147) 1-[4-(4-amino-3,5-dibromophenyl)-1,4-dioxobutyl]-N-{2-{[1.41]bipiperidinyl-1'-ylcarbonylamino}phenylmethyl}-4-piperidineamine
(148) 3-{8-[4-(4-amino-3,5-dibromophenyl)-1,4-dioxobutyl]-8-azabicyclo[3.2.1]oct-3-yl}-3,4-dihydro-2(1H)-quinazolinone
(149) 3-{3-[4-(4-amino-3,5-dibromophenyl)-1,4-dioxobutyl]-7-methyl-3,7-diazabicyclo[3.3.1]non-9-yl}-3,4-dihydro-2(1H)-quinazolinone (diastereomer to compound no. 150)
(150) 3-{3-[4-(4-amino-3,5-dibromophenyl)-1,4-dioxobutyl]-7-methyl-3,7-diazabicyclo[3.3.1]non-9-yl}-3,4-dihydro-2(1H)-quinazolinone (diastereomer to compound no. 149)
(151) 3-{1-[4-(4-amino-3,5-dibromophenyl)-1,4-dioxobutyl]-4-piperidinyl}-5-(phenylmethyl)-imidazolidin-2,4-dione
(152) 3-{1-[4-(4-amino-3,5-dibromophenyl)-1,4-dioxobutyl]-4-piperidinyl}-5-phenyl-imidazolidin-2,4-dione
(153) 3-{1-[4-(4-amino-3,5-dibromophenyl)-1,4-dioxobutyl]-4-piperidinyl}-3,4-dihydro-2,1,3-benzothiadiazin-2,2-dioxide
(154) 1-{1-[4-(4-amino-3,5-dibromophenyl)-1,4-dioxobutyl]-4-piperidinyl}-1,3-dihydro-4-(4-fluorophenyl)-2(2H)-imidazolone
(155) 4-amino-N-{2-[4-(3,4-dihydro-2(1H)-oxoquinazolin-3-yl)-1-piperidinyl]-2-oxoethyl}-3-fluoro-5-iodobenzamide
(156) 1-{1-[4-(4-amino-3,5-dibromophenyl)-1,4-dioxobutyl]-4-piperidinyl}-1,3-dihydro-4-(2-naphthyl)-2(2H)-imidazolone
(157) 1-{1-[4-(4-amino-3,5-dibromophenyl)-1,4-dioxobutyl]-4-piperidinyl}-4-(4-biphenylyl)-1,3-dihydro-2(2H)-imidazolone
(158) 1-{1-[4-(4-amino-3,5-dibromophenyl)-1,4-dioxobutyl]-4-piperidinyl}-1,3-dihydro-4-(2-methoxyphenyl)-2(2H)-imidazolone
(159) 1-{1-[4-(4-amino-3,5-dibromophenyl)-1,4-dioxobutyl]-4-piperidinyl}-4-(3,4-dichlorophenyl)-1,3-dihydro-2(2H)-imidazolone
(160) 3-{1-[4-(4-amino-3,5-dibromophenyl)-1,4-dioxobutyl]-4-piperidinyl}-6-chloro-3,4-dihydro-2(1H)-quinazolinone
(161) 3-[1'-(4-amino-3,5-dibromobenzoyl)-[1.4']bipiperidinyl-4-yl]-5-(phenylmethyl)-imidazolidin-2,4-dione
(162) 1-[1'-(4-amino-3,5-dibromobenzoyl)-[1.4']bipiperidinyl-4-yl]-1,3-dihydro-4-(2-naphthyl)-2(2H)-imidazolone
(163) 3-{1-[4-(4-amino-3,5-dibromophenyl)-1,4-dioxobutyl]-4-piperidinyl}-1,3-dihydro-2(2H)-imidazo[4.5-c]quinolinone
(164) 3-{1-[1,4-dioxo-4-(1,2,3,4,5,6,7,8-octahydro-9-phenanthryl)butyl]-4-piperidinyl}-3,4-dihydro-2(1H)-quinazolinone
(165) (R,S)-1-(4-amino-3,5-dibromobenzoyl)-3-[4-(3,4-dihydro-2(1H)-oxoquinazolin-3-yl)-1-piperidinyl]-pyrrolidine
(166) (R,S)-1-(3,4-dichlorobenzoyl)-3-[4-(3,4-dihydro-2(1H)-oxoquinazolin-3-yl)-1-piperidinyl]-pyrrolidine
(167) (E)-3-{1-[4-(4-biphenylyl)-1,4-dioxo-2-buten-1-yl]-4-piperidinyl}-3,4-dihydro-2(1H)-quinazolinone
(168) (E)-3,4-dihydro-3-{1-[1,4-dioxo-4-(4-ethoxycarbonylphenyl)-2-buten-1-yl]-4-piperidinyl}-2(1H)-quinazolinone
(169) (E)-3,4-dihydro-3-{1-[1,4-dioxo-4-(3,4,5-trimethoxyphenyl)-2-buten-1-yl]-4-piperidinyl}-2(1H)-quinazolinone
(170) (E)-3,4-dihydro-3-{1-[1,4-dioxo-4-(3-trifluoromethoxyphenyl)-2-buten-1-yl]-4-piperidinyl}-2(1H)-quinazolinone
(171) (E)-3,4-dihydro-3-{1-[1,4-dioxo-4-(3-ethylphenyl)-2-buten-1-yl]-4-piperidinyl}-2(1H)-quinazolinone
(172) (E)-3,4-dihydro-3-{1-[1,4-dioxo-4-(3-methoxyphenyl)-2-buten-1-yl]-4-piperidinyl}-2(1H)-quinazolinone
(173) (E)-3,4-dihydro-3-{1-[1,4-dioxo-4-(4-methylethoxyphenyl)-2-buten-1-yl]-4-piperidinyl}-2(1H)-quinazolinone
(174) (E)-3,4-dihydro-3-{1-[1,4-dioxo-4-(3-fluoro-4-methoxyphenyl)-2-buten-1-yl]-4-piperidinyl}-2(1H)-quinazolinone (175) (E)-3,4-dihydro-3-{1-[1,4-dioxo-4-[4-(1-piperidinyl)-phenyl]-2-buten-1-yl]-4-piperidinyl}-2(1H)-quinazolinone
(176) (E)-3,4-dihydro-3-{1-[1,4-dioxo-4-(3,4-methylenedioxy-phenyl)-2-buten-1-yl]-4-piperidinyl}-2(1H)-quinazolinone
(177) (E)-3,4-dihydro-3-{1-[1,4-dioxo-4-(4-trifluoromethyl-phenyl)-2-buten-1-yl]-4-piperidinyl}-2(1H)-quinazolinone
(178) (E)-3,4-dihydro-3-{1-[1,4-dioxo-4-(4-carboxyphenyl)-2-buten-1-yl]-4-piperidinyl}-2(1H)-quinazolinone
(179) 3-{1-[5-(4-amino-3,5-dibromophenyl)-1,5-dioxopentyl]-4-piperidinyl}-3,4-dihydro-2(1H)-quinazolinone
(180) 3-{1-[4-(4-amino-3,5-dibromophenyl)-1,4-dioxobutyl]-4-piperidinyl}-2-(1,1-dimethylethoxycarbonylamino)-3,4-dihydroquinazoline
(181) 2-amino-3-{1-[4-(4-amino-3,5-dibromophenyl)-1,4-dioxobutyl]-4-piperidinyl}-3,4-dihydroquinazoline
(182) 3-{1-[4-(4-amino-3,5-dibromophenyl)-1,4-dioxobutyl]-4-piperidinyl}-3,4-dihydro-2(1H)-quinazolinethione
(183) 3-{1-[4-(4-amino-3,5-dibromophenyl)-1,4-dioxobutyl]-4-piperidinyl}-2-cyanimino-1,2,3,4-tetrahydroquinazoline
(184) (R,S)-3-{1-[4-(4-amino-3,5-dibromophenyl)-1,4-dioxo-3-methylbutyl]-4-piperidinyl}-3,4-dihydro-2(1H)-quinazolinone
(185) 3-{1-[4-(4-amino-3,5-dibromophenyl)-1,4-dioxobutyl]-4-piperidinyl}-7-methoxy-2,3,4,5-tetrahydro-1,3-benzodiazepin-2(1H)-one
(186) 3-{1-[4-(4-amino-3,5-dibromophenyl)-1,4-dioxobutyl]-4-piperidinyl}-2,3,4,5-tetrahydro-1,3-benzodiazepin-2(1H)-one
(187) 1-[4-(4-amino-3,5-dibromophenyl)-1,4-dioxobutyl]-N-(1,1-dimethylethoxycarbonyl-N-[(2-methanesulphonylaminophenyl)-methyl]-4-piperidineamine
(188) 1-[4-(4-amino-3,5-dibromophenyl)-1,4-dioxobutyl]-N-(1,1-dimethylethoxycarbonyl-N-{2-{[1.4']bipiperidinyl-1'-ylcarbonylamino}phenylmethyl}-4-piperidineamine, but particularly the abovementioned compounds (12), (37), (38), (81), (82), (83), (115), (117), (120), (123), (163) and (182), and the salts thereof.

The compounds of general formula I are prepared by methods known in principle. The following methods have proved particularly suitable for preparing the compounds of general formula I according to the invention:

a) In order to prepare compounds of general formula I wherein $Z^1$ denotes the methylene group, $Z^2$ denotes one of the groups —$(CH_2)_2$—, —$(CH_2)_3$— or —CH=CH— and $Z^3$ denotes the carbonyl group and R has the meanings given hereinbefore with the exception of a 4-[3,4-dihydro-2(1H)-oxoquinazolin-3-yl]-[1.4']bipiperidinyl-1'-yl group:

alkylating a compound of general formula

R'—H    (IVa), wherein

R' has the meanings given for R hereinbefore with the exception of a 4-[3,4-dihydro-2(1H)-oxoquinazolin-3-yl]-[1.4']bipiperidinyl-1'-yl group, with a compound of general formula

X—$CH_2$—$Z^2$—$Z^3$—$R^1$    (V), wherein $R^1$ is as hereinbefore defined, $Z^2$ denotes one of the groups —$(CH_2)_2$, —$(CH_2)_3$— or —CH=CH—, $Z^3$ denotes the carbonyl group and X denotes a leaving group, e.g. a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, whilst the substituents may be identical or different.

The reaction is carried out with or without auxiliary bases at temperatures between 0° C. and +140° C., preferably between +20° C. and +100° C., and preferably in the presence of solvents. The auxiliary bases used may be alkali metal and alkaline earth metal hydroxides, e.g. sodium hydroxide, potassium hydroxide or barium hydroxide, but preferably alkali metal carbonates, e.g. sodium carbonate, potassium carbonate or caesium carbonate, and also alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, but preferably dipolar aprotic solvents such as acetonitrile, dimethyl formamide, dimethyl acetamide, N-methyl-pyrrolidone, methyl-isobutylketone or mixtures thereof; if alkali metal or alkaline earth metal hydroxides, alkali metal carbonates or acetates are used as the auxiliary bases, water may also be added to the reaction mixture as cosolvent. To increase the reactivity of the group X in the starting materials of general formula V organic or preferably inorganic iodides such as sodium or potassium iodide are also added to the reaction mixture.

b) In order to prepare compounds of general formula I wherein $Z^1$ denotes the carbonyl group, $Z^2$ denotes one of the groups —$(CH_2)_2$— or —$(CH_2)_3$, wherein a hydrogen atom may be replaced by a $C_{1-3}$-alkyl or a hydroxy group, one of the groups —$CH_2$—NH— or —$(CH_2)_2$—NH, wherein a hydrogen atom bound to a carbon atom and/or the hydrogen atom of the imino group may each be replaced by a $C_{1-3}$-alkyl group, or the group —CH=CH— and $Z^3$ denotes the methylene or carbonyl group:

Coupling a carboxylic acid of general formula

HOOC—$Z^2$—$Z^3$—$R^1$    (VI),

wherein $R^1$ is as hereinbefore defined, $Z^2$ denotes one of the groups —$(CH_2)_2$— or —$(CH_2)_3$, wherein a hydrogen atom may be replaced by a $C_{1-3}$-alkyl or a hydroxy group, one of the groups —$CH_2$—NH— or —$(CH_2)_2$—NH, wherein a hydrogen atom bound to a carbon atom and/or the hydrogen atom of the imino group may each be replaced by a $C_{1-3}$-alkyl group, or the group —CH=CH—, and $Z^3$ denotes the methylene or carbonyl group, with a compound of general formula

R—H    (IV),

wherein

R is as hereinbefore defined.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +20° C. If necessary, N-ethyl-diisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the optionally $N^2$-protected α-amino acid which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the abovementioned solvents and at temperatures between −20 and +20° C., preferably 0 and +20° C.

c) In order to prepare compounds of general formula I wherein $Z^1$ denotes the carbonyl group, $Z^2$ denotes one of the groups —(CH$_2$)$_2$— or —(CH$_2$) 3, wherein a hydrogen atom may be replaced by a $C_{1-3}$-alkyl or hydroxy group, one of the groups —CH$_2$—NH— or —(CH$_2$)$_2$—NH, wherein a hydrogen atom bound to a carbon atom and/or the hydrogen atom of the imino group may each be replaced by a $C_{1-3}$-alkyl group, or the group —CH=CH— and $Z^3$ denotes a methylene or carbonyl group:

coupling a compound of general formula

$$\text{Nu—CO—}Z^2\text{—}Z^3\text{—}R^1 \quad\quad (VII),$$

wherein $R^1$ is as hereinbefore defined, $Z^2$ denotes one of the groups —(CH$_2$)$_2$— or —(CH$_2$)$_3$, wherein a hydrogen atom may be replaced by a $C_{1-3}$-alkyl or a hydroxy group, one of the groups —CH$_2$—NH— or —(CH$_2$)$_2$—NH, wherein a hydrogen atom bound to a carbon atom and/or the hydrogen atom of the imino group may each be replaced by a $C_{1-3}$-alkyl group, or the group —CH=CH—, $Z^3$ denotes a methylene or carbonyl group and Nu denotes a leaving group, e.g. a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, whilst the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, with a compound of general formula

$$R\text{—}H \quad\quad (IV),$$

wherein

R is as hereinbefore defined.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali-metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

d) In order to prepare compounds of general formula I wherein $Z^1$ and $Z^3$ each denote the carbonyl group and $Z^2$ denotes the group —(CH$_2$)$_2$—:

catalytically hydrogenating a compound of general formula

$$R\text{—CO—CH=CH—CO—}R^1 \quad\quad (I'),$$

wherein

R and $R^1$ are as hereinbefore defined.

The catalytic hydrogenation may be carried out both with heterogeneous and with homogeneous catalysts. Of the heterogeneous catalysts those consisting of metals of the 8th sub-group of the Periodic Table are preferred, e.g. Raney nickel (R-Ni), palladium on charcoal, nickel reduced with sodium borohydride, or nickel boride (Paul, Buisson and Joseph, Ind. Eng. Chem. 44, 1006 (1952); Brown, J. C. S. Chem. Commun. 1969, 952, J. Org. Chem. 35, 1900. (1973); Brown and Ahuja, J. Org. Chem. 38, 2226 (1973), J. C. S. Chem. Commun. 1973, 553; Schreifels, Maybury and Swartz, J. Org. Chem. 46, 1263 (1981); Nakao and Fujishige, Chem. Lett. 1981, 925; Nakao, Chem. Lett. 1982, 997), platinum metal, platinum on charcoal, platinum(IV)-oxide, rhodium, ruthenium, sodium hydride-sodium methoxide-nickel(II)-acetate (Brunet, Gallois and Caubère, J. Org. Chem. 45, 1937, 1946 (1980)), of the homogeneous catalysts chlorotris(triphenylphosphine) and RhCl(Ph$_3$P)$_3$ (Wilkinson's catalyst; Abstract: Jardine, Prog. Inorg. Chem.

28, 63–202 (1981)) are preferred. When using the abovementioned heterogeneous catalysts, any nitro groups present in the groups R or $R^1$ are simultaneously reduced to amino groups, while if excessively high temperatures are used nitrile groups are also reduced to aminomethyl groups. The abovementioned homogeneous catalyst chlorotris(triphenylphosphine) on the other hand leaves intact any nitro or cyano groups present during the hydrogenation of the C=C-double bonds in compounds of general formula VII. The hydrogenations are carried out at temperatures between −5° C. and +50° C., preferably between +15 and +25° C. and most preferably at room temperature. Both the catalyst and the hydrogen required can be produced in situ, for example by treating hexachloroplatinic(IV)-acid or rhodium(III)-chloride with sodium borohydride (Brown and Sivasankaran, J. Am. Chem. Soc. 84, 2828 (1962); Brown and Brown, J. Am. Chem. Soc. 84, 1494, 1495, 2829 (1962), J. Org. Chem. 31, 3989 (1966); Brown, Sivasankaran and Brown, J. Org. Chem. 28, 214 (1963)). Examples of solvents which are particularly suitable for the catalytic hydrogenations in question are ethanol, methanol, ethyl acetate, 1,4-dioxane and acetic acid, if miscible therewith, optionally with the addition of water, and mixtures of these solvents.

e) In order to prepare compounds of general formula I wherein $Z^1$ denotes a methylene or carbonyl group or, if $Z^2$ denotes a divalent group of general formula III, may also denote a bond, $Z^2$ denotes one of the groups —$CH_2$—NH— or —$(CH_2)_2$—NH, wherein a hydrogen atom bound to a carbon atom and/or the hydrogen atom of the imino group may each be replaced by a $C_{1-3}$-alkyl group, or a divalent group of general formula

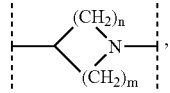

(III)

wherein m and n independently of one another denote one of the numbers 1, 2, 3 or 4 and $Z^3$ denotes the carbonyl group:

coupling a carboxylic acid of general formula

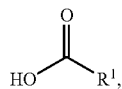

(VIII)

wherein $R^1$ is as hereinbefore defined, with a compound of general formula

R—$Z^1$—$Z^2$—H        (IX), wherein

R is as hereinbefore defined, $Z^1$ denotes a methylene or carbonyl group or, if $Z^2$ denotes a divalent group of general formula III, may also denote a bond, $Z^2$ denotes one of the groups —$CH_2$—NH— or —$(CH_2)_2$—NH, wherein a hydrogen atom bound to a carbon atom and/or the hydrogen atom of the imino group may each be replaced by a $C_{1-3}$-alkyl group, or a divalent group of general formula

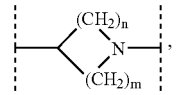

(III)

wherein m and n independently of one another denote one of the numbers 1, 2, 3 or 4 and $Z^3$ denotes the carbonyl group.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N',N'-tetramethyluronium hexafluorophosphate (HBTU) or -tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +20° C. If necessary, N-ethyldiisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the optionally $N^2$-protected α-amino acid which is to be coupled and monoisobutyl carbonate, is obtained using isobutyl chlorocarbonate in the presence of bases such as 4-methyl-morpholine or 4-ethyl-morpholine. The preparation of this mixed anhydride and the coupling with amines are carried out in a one-pot process, using the abovementioned solvents and at temperatures between −20 and +20° C., preferably 0 and +20° C.

f) In order to prepare compounds of general formula I wherein $Z^1$ denotes a methylene or carbonyl group or, if $Z^2$ denotes a divalent group of general formula III, $Z^1$ may also denote a bond, $Z^2$ denotes one of the groups —$CH_2$—NH— or —$(CH_2)_2$—NH, wherein a hydrogen atom bound to a carbon atom and/or the hydrogen atom of the imino group may each be replaced by a $C_{1-3}$-alkyl group, or $Z^1$ denotes a divalent group of general formula

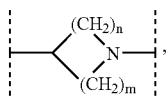
(III)

wherein m and n independently of one another denote one of the numbers 1, 2, 3 or 4 and $Z^3$ denotes the carbonyl group:

coupling a compound of general formula

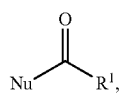
(X)

wherein $R^1$ is as hereinbefore defined and

Nu denotes a leaving group, e.g. a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, whilst the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, with a compound of general formula

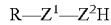 (IX), wherein

R is as hereinbefore defined, $Z^1$ denotes a methylene or carbonyl group or, if $Z^2$ denotes a divalent group of general formula III, may also denote a bond, $Z^2$ denotes one of the groups —CH₂—NH— or —(CH₂)₂—NH wherein a hydrogen atom bound to a carbon atom and/or the hydrogen atom of the imino group may each be replaced by a $C_{1-3}$-alkyl group, or a divalent group of general formula

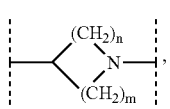
(III)

wherein m and n independently of one another denote one of the numbers 1, 2, 3 or 4 and $Z^3$ denotes the carbonyl group.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyldiisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

g) In order to prepare compounds of general formula I wherein R and $R^1$ are as hereinbefore defined, with the proviso that they must not carry any free amino groups, $Z^1$ denotes the carbonyl group, $Z^2$ denotes one of the groups —NH—CH₂— or —NH—(CH₂)₂, wherein a hydrogen atom bound to a carbon atom and/or the hydrogen atom of the imino group may each be replaced by a $C_{1-3}$-alkyl group and $Z^3$ denotes the methylene or carbonyl group:

reacting an amine of general formula,

 (XI), wherein

R" has the meanings given for R hereinbefore, with the proviso that the group does not contain a free amino group, with a carbonic acid derivative of general formula

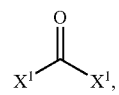
(XII)

wherein $X^1$ denotes a nucleofugic group, preferably the 1H-imidazol-1-yl, 1H-1,2,4-triazol-1-yl, trichloromethoxy or 2,5-dioxopyrrolidin-1-yloxy group, and with a compound of general formula

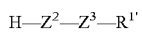 (XIII), wherein the group $R^{1'}$ has the meanings given for $R^1$ hereinbefore, with the proviso that the group does not contain a free amino group, $Z^2$ denotes one of the groups —NH—CH₂— or —NH—(CH₂)₂, wherein a hydrogen atom bound to a carbon atom and/or the hydrogen atom of the imino group may each be replaced by a $C_{1-3}$-alkyl group and $Z^3$ denotes the methylene or carbonyl group.

The reactions which are theoretically two-step reactions are usually carried out as one-pot processes, preferably by reacting one of the two components XI or XIII with equimolar quantities of the carbonic acid derivative of general formula XII in a suitable solvent at lower temperature in the first stage, then adding at least equimolar amounts of the other component XIII or XI and finishing the reaction at elevated temperature. The reactions with bis-(trichloromethyl)-carbonate are preferably carried out in the presence of at least 2 equivalents (based on bis-(trichloromethyl)-carbonate) of a tertiary base, e.g. triethylamine, N-ethyl-diisopropylamine, pyridine, 1,5-diazabicyclo[4,3,0]non-5-ene, 1,4-diazabicyclo[2,2,2]octane or 1,8-diazabicyclo[5,4,0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis-(trichloromethyl)-carbonate is used as the carbonyl component anhydrous chlorohydrocarbons such as dichloromethane, 1,2-dichloroethane or trichloroethylene are preferred. The reaction temperatures for the first reaction step are between −30 and +25° C., preferably −5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Vol. V, p. 53–93, Verlag Chemie, Weinheim/Bergstr., 1967; P. Majer and R. S. Randad, J. Org. Chem. 59, 1937–1938 (1994); K. Takeda, Y. Akagi, A. Saiki, T. Sukahara and H. Ogura, Tetrahedron Letters 24 (42), 4569–4572 (1983)).

h) In order to prepare compounds of general formula I wherein at least one of the groups. R and $R^1$ contains one or more carboxy groups:

alkaline saponification of a carboxylic acid ester of general formula

(Ia), wherein $Z^1$, $Z^2$ and $Z^3$ are as hereinbefore defined and $R^a$ and $R^{1a}$ have the meanings given for R and $R^1$, respectively, hereinbefore, with the proviso that at least one of these groups contains one or more alkoxycarbonyl groups, optionally followed by treatment with dilute organic or inorganic acids in order to liberate the basic carboxylic acids from the salts initially formed.

For the alkaline saponification of the esters of general formula (Ia), lithium hydroxide, sodium hydroxide and potassium hydroxide are preferred; however, other alkali metal hydroxides such as caesium hydroxide, or alkaline earth metal hydroxides, for example barium hydroxide, or tetralkylammonium hydroxides are also suitable. The procedure is carried out in aqueous solution and advantageously with the addition of water-miscible co-solvents, preferably alcohols such as methanol, ethanol or 2-ethoxyethanol, or ethers such as tetrahydrofuran or 1,4-dioxane. Suitable temperatures for alkaline saponification are between −10° C. and the boiling temperature of the water/solvent mixture used, but ambient temperature is preferred. Dilute aqueous organic or inorganic acids, e.g. acetic acid, oxalic acid, methanesulphonic acid, hydrochloric acid, sulphuric acid and phosphoric acid are suitable for liberating the basic carboxylic acids from the salts thereof formed initially.

i) In order to prepare compounds of general formula I wherein at least one of the groups R and $R^1$ contains one or more amino groups:

acid hydrolysis of an acylamine of general formula

(Ib), wherein $Z^1$, $Z^2$ and $Z^3$ are as hereinbefore defined, $R^b$ and $R^{1b}$ have the meanings given hereinbefore for R and $R^1$, respectively, with the proviso that $R^b$ is substituted by an acetylamino, propionylamino, cycloalkanecarbonylamino or benzoylamino group and/or $R^{1b}$ is substituted by an acetylamino, propionylamino or benzoylamino group.

The acid hydrolysis is carried out using: dilute to semi-concentrated aqueous, organic or inorganic acids such as hydrochloric acid, hydrobromic acid, trichloroacetic acid or sulphuric acid, and in the presence or absence of cosolvents such as methanol, ethanol, acetic acid or dioxane. Suitable temperatures are between ambient temperature and 100° C.; the boiling temperature of the solvent mixture used is preferred.

j) In order to prepare compounds of general formula I wherein the group R contains one or two primary or secondary amino groups:

acidolysis of a compound of general formula

(Ic), wherein $R^1$, $Z^1$, $Z^2$ and $Z^3$ are as hereinbefore defined and $R^c$ has the meanings given for R hereinbefore, with the proviso that this group contains one or two primary or secondary amino groups which are substituted by a ter.t.alkoxycarbonyl group.

Acidolysis with trifluoroacetic acid is preferred, working with or without inert solvents, e.g. dichloromethane, and preferably in the absence of water. Suitable temperatures are between −50 and +90° C., preferably between 0° C. and room temperature. It has also proved satisfactory to carry out the acidolysis of compounds of general formula (1c) with methanolic hydrochloric acid solution under reflux conditions, although experience has shown that an attack on carboxamide and ester functions cannot be entirely ruled out, which is why the trifluoroacetic acid variant is generally the method of choice.

k) In order to prepare compounds of general formula I wherein $Z^1$ and $Z^3$ each denote the carbonyl group, $Z^2$ denotes the group —$(CH_2)_2$— and the group $R^1$ denotes a phenyl group which carries a tertiary amino group in the 4 position relative to the point of attachment but may otherwise be substituted as described hereinbefore:

nucleophilic aromatic substitution (cf. also: Jerry March, Advanced Organic Chemistry, Third Edition, page 576–578, published by John Wiley & Sons, New York-Chichester-Brisbane-Toronto-Singapore, 1985) of a compound of general formula

(Id), wherein

R is as hereinbefore defined, $Z^1$ and $Z^3$ each denote the carbonyl group, $Z^2$ denotes the group —(CH$_2$)2- and the group $R^{1d}$ denotes a phenyl group which carries a nucleophilically exchangeable function, preferably a fluorine, chlorine, bromine or iodine atom, in the 4 position relative to the point of attachment, but may otherwise be substituted as described hereinbefore, with a corresponding amine, for example with dimethylamine, piperidine, 1-(3-dimethylaminopropyl)piperazine, [4,1] bi-piperidinyl, 4-(4-methyl-1-piperazinyl)piperidine or 4-[4-(3-dimethylaminopropyl)-1-piperazinyl]piperidine.

The reactions are carried out in excess secondary dialkylamine as solvent or using dipolar, aprotic solvents such as dimethylsulphoxide, dimethylformamide or sulpholane, and at temperatures of between 50 and 160° C., preferably 70 and 140° C. It may also be advantageous to add potassium carbonate to the reaction mixture.

l) In order to prepare compounds of general formula I wherein the group R is uniformly mono-, di- or trisubstituted in the carbon skeleton by an aminocarbonyl, alkylaminocarbonyl or dialkylaminocarbonyl group:

coupling a compound of general formula

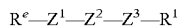
$$R^e\!-\!Z^1\!-\!Z^2\!-\!Z^3\!-\!R^1 \qquad (Ie),$$

wherein the group $R^e$ has the meanings given for R hereinbefore with the proviso that it is mono-, di- or trisubstituted in the carbon skeleton by the carboxy group, and $R^1$, $Z^1$, $Z^2$ and $Z^3$ are as hereinbefore defined, with ammonia or a corresponding alkylamine, for example ethanolamine, or a dialkylamine, for example 1-methylpiperazine or morpholine.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +20° C. If necessary, N-ethyl-diisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the optionally $N^2$-protected α-amino acid which is to be coupled and monoisobutyl carbonate is obtained, using isobutyl chlorocarbonate in the presence of bases such as 4-methyl-morpholine or 4-ethyl-morpholine. The preparation of this mixed anhydride and the coupling with amines are carried out in a one-pot process, using the abovementioned solvents and at temperatures between −20 and +20° C., preferably 0 and +20° C.

m) In order to prepare compounds of general formula I wherein the group R is substituted in the carbon skeleton by an acetylamino group or in the carbon skeleton by an acetylamino group and at the same time is substituted at one of the aza-nitrogen atoms by an acetyl group:

aminolysis of acetic anhydride by a compound of general formula

$$R^f\!-\!Z^1\!-\!Z^2\!-\!Z^3\!-\!R^1 \qquad (If),$$

wherein $R^1$, $Z^1$, $Z^2$ and $Z^3$ are as hereinbefore defined and the group $R^f$ has the meanings given for R hereinbefore with the proviso that it is substituted in the carbon skeleton by an amino group.

The aminolysis reaction is carried out in water or inert, usually polar and water-miscible solvents, such as tetrahydrofuran, 1,4-dioxane, pyridine, acetic acid or dimethylformamide, or in mixtures thereof and at temperatures between 0° C. and 100° C. In order to obtain selective acetylation of the amino group in the carbon skeleton, it is preferable to use alcohols such as methanol or ethanol as the solvents and to carry out the procedure at ambient temperature.

n) In order to prepare compounds of general formula I wherein the group R is as hereinbefore defined, with the proviso that it is substituted in the carbon skeleton by an acetylamino, propionylamino, cycloalkanecarbonylamino or benzoylamino group:

coupling a compound of general formula

(XIV)

wherein $R^G$ denotes a methyl, ethyl, cycloalkyl or phenyl group and Nu denotes a leaving group such as a halogen atom, e.g. the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, wherein the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, with a compound of general formula $$R^f-Z^1-Z^2-Z^3-R^1 \quad (If),$$

wherein $R^1$, $Z^1$, $Z^2$ and $Z^3$ are as hereinbefore defined and the group $R^f$ has the meanings given for R hereinbefore with the proviso that it is substituted in the carbon skeleton by an amino group.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabi-cyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

o) In order to prepare compounds of general formula I wherein the group R is as hereinbefore defined with the proviso that it is substituted in the carbon skeleton by an aminocarbonylamino group:

reacting a compound of general formula $$R^f-Z^1-Z^2-Z^3-R^1 \quad (If),$$

wherein $R^1$, $Z^1$, $Z^2$ and $Z^3$ are as hereinbefore defined and the group $R^f$ has the meanings given for R hereinbefore, with the proviso that it is substituted in the carbon skeleton by an amino group, with cyanic acid which is produced in situ from alkali metal cyanates, for example sodium cyanate or potassium cyanate, and dilute inorganic acids such as hydrochloric acid or sulphuric acid. The reaction is carried out in suitable, water-miscible solvents, preferably tetrahydrofuran or 1,4-dioxane, and using water as cosolvent. Suitable reaction temperatures are between −5 and +50° C., preferably 0 and +25° C.

p) In order to prepare compounds of general formula I wherein the group R is as hereinbefore defined, with the proviso that it is substituted by an aminomethyl group in the carbon skeleton, and $Z^2$ has the meanings given hereinbefore with the exception of the group —CH=CH—:

catalytic hydrogenation of a compound of general formula $$R^g-Z^1-Z^2-Z^3-R \quad (Ig),$$

wherein $R^1$, $Z^1-Z^2$ and $Z^3$ are as hereinbefore defined and the group $R^g$ has the meanings given for R hereinbefore, with the proviso that it is substituted in the carbon skeleton by a nitrile group.

Nickel and palladium catalysts have proved suitable for the catalysis, e.g. Raney nickel (R-Ni), palladium on charcoal and nickel reduced with sodium borohydride or nickel boride (Paul, Buisson and Joseph, Ind. Eng. Chem. 44, 1006 (1952); Brown, J. C. S. Chem. Commun. 1969, 952, J. Org. Chem. 35, 1900 (1973); Brown and Ahuja, J. Org. Chem. 38, 2226 (1973), J. C. S. Chem. Commun. 1973, 553; Schreifels, Maybury and Swartz, J. Org. Chem. 46, 1263 (1981); Nakao and Fujishige, Chem. Lett. 1981, 925; Nakao, Chem. Lett. 1982, 997). Generally, it has proved suitable to work in a neutral or slightly alkaline medium, particularly when using Raney nickel as catalyst, while it is usually beneficial to add ammonia to the reaction mixture. Palladium catalysts are also suitable for hydrogenating compounds of general formula Ig under acid conditions, i.e. in the presence of hydrochloric acid, sulphuric acid or phosphoric acid. Whereas nickel catalysts generally require slightly elevated temperatures between 40 and 100° C., the hydrogenations in question can be successfully carried out at ambient temperature using the palladium catalyst mentioned above.

Suitable hydrogen pressures are between normal pressure and 250 bar, while if palladium on charcoal is used as catalyst pressures of up to 10 bar are preferred. Suitable solvents are alcohols such as methanol or ethanol, ethers such as tetrahydrofuran or 1,4-dioxane, or esters, e.g. methyl acetate or ethyl acetate. Any C=C double bonds which may have been present in the chain $Z^1-Z^2-Z^3-Z^4-Z^5$ of the starting material Ig are also saturated during the hydrogenation.

q) In order to prepare compounds of general formula I wherein

R is the 4-[3,4-dihydro-2(1H)-thioxoquinazolin-3-yl]-1-piperidinyl or 4-[3,4-dihydro-2(1H)-cyanoiminoquinazolin-3-yl]-1-piperidinyl group:

reacting a diamine of general formula

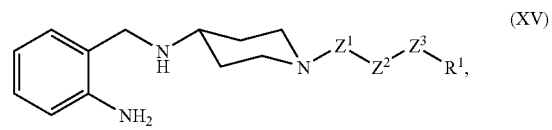

wherein $R^1$, $Z^1$, $Z^2$ and $Z^3$ are as hereinbefore defined, with one of the carbonic acid derivatives N,N'-thiocarbonyldiimidazole or cyanoimino-diphenylcarbonate. The reactions are carried out at temperatures between 20° C. and +100° C., preferably between +40° C. and +120° C., and using inert solvents, for example dichloromethane, tetrahydrofuran, 1,4-dioxane, acetonitrile, dimethylformamide, dimethylacetamide, N-methyl-pyrrolidone or mixtures thereof.

The arylalkanes, arylalkenes and aryl-azaalkanes of general formula I according to the invention contain a chiral centre in some cases. As a result of a C=C double bond which may in certain circumstances be present in the chain $-Z^1-Z^2-Z^3-$, some of the compounds may also occur in the form of two geometric isomers; the methods of synthesis described hereinbefore predominantly produce the (E) isomers. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, neutralised with a base such as sodium carbonate or potassium carbonate, sodium hydroxide solution or potassium hydroxide solution and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting materials of general formulae V, VIII, X, XII, XIII and XIV required for the synthesis of the compounds of general formula I are commercially obtainable or may be prepared by methods known from the literature. Compounds of general formulae IV, IVa and XI are described in WO 98/11128 or are prepared analogously to the processes described therein. Compounds of general formula IX may easily be obtained from compounds of general formula IV analogously to methods known from the literature. Compounds of general formulae Ia, Ib, Ic, Id, Ie, If, Ig, I' and XV may easily be obtained using the methods described in the present application. 4-Aryl-4-oxobutanoic acids of general formula VI may either easily be prepared analogously to methods known from the literature or may be obtained by catalytic hydrogenation of 4-aryl-4-oxo-2-butenoic acids, which may in turn be synthesised from suitable alkanophenones by a process described in published German patent applications 2 047 806 and 2 103 749, by condensation with glyoxylic acid hydrate under acid conditions. Compounds of general formula VII may be obtained from VI by conventional methods known from the literature.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain an acid function, for example a carboxy group, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of compounds of general formula I for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds of general formula I show IC$_{50}$ values ≦10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds of general formula I exhibit CGRP-antagonistic properties in the in vitro test model described, in a dosage range of between $10^{-11}$ to $10^{-5}$ M.

In view of their pharmacological properties the compounds of general formula I and the salts thereof with physiologically acceptable acids or bases are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), cardiovascular diseases, morphine tolerance, skin diseases, particularly thermal and radiation-induced skin damage including sunburn, inflammatory diseases, e.g. inflammatory diseases of the joints (arthritis), inflammatory lung diseases, allergic rhinitis, asthma, diseases accompanied by excessive vasodilatation and consequent reduced circulation of blood through the tissues, e.g. shock and sepsis. The symptoms of menopausal hot flushes in oestrogen-deficient women caused by vasodilatation and increased blood flow are favourably affected by the CGRP-antagonists of the present application in a preventive and acute-therapeutic capacity, this therapeutic approach being distinguished from hormone replacement by the absence of side effects. Furthermore, the compounds of general formula I have a general pain-relieving effect.

The dosage required to achieve a corresponding effect is conveniently 0.001 to 30 mg/kg of body weight, preferably 0.01 to 5 mg/kg of body weight, when administered intravenously or subcutaneously and 0.01 to 50 mg/kg of body weight, preferably 0.1 to 30 mg/kg of body weight when administered orally, nasally or by inhalation, 1 to 3× a day in each case.

For this, the compounds of general formula I prepared according to the invention, optionally combined with other active substances such as e.g. antiemetics, prokinetics, neuroleptics, antidepressants, neurokinine antagonists, anti-convulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, 5-$HT_{1D}$ agonists or other anti-migraine agents, together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, may be formulated into conventional galenic preparations such as plain or coated tablets, capsules, powders, suspensions, solutions, metered dose aerosols or suppositories.

The active substances which may be used for the above-mentioned combinations thus include, for example, meloxicam, ergotamine, dihydroergotamine, metoclopramide, domperidone, diphenhydramine, cyclizine, promethazine, chlorpromazine, dexamethasone, flunarizine, dextropropoxyphene, meperidine, propranolol, nadolol, atenolol, clonidine, indoramine, carbamazepine, phenyloin, valproate, amitryptilin, lidocaine, diltiazem or sumatriptan and other 5-$HT_{1D}$-agonists such as, for example, naratriptan, zolmitriptan, avitriptan, rizatriptan and eletriptan. The dosage of these active substances is expediently 1/5 of the lowest recommended dose to 1/1 of the normally recommended dose, i.e. for example 20 to 100 mg of sumatriptan.

The invention further relates to the use of, the compounds of general formula I as valuable adjuvants for the production and purification (by affinity chromatography) of antibodies as well as in RIA and ELISA assays, after suitable radioactive labelling, for example by direct labelling with $^{125}I$ or $^{131}I$ or by tritiation of suitable precursors, for example by replacing halogen atoms with tritium, and as a diagnostic or analytical adjuvant in neurotransmitter research.

The Examples which follow are intended to illustrate the invention:

Preliminary remarks:

Satisfactory elementary analyses, IR, UV, $^1$H-NMR and generally also mass spectra have been obtained for all the compounds. Unless otherwise stated, $R^f$ values were obtained using ready-made silica gel TLC plates 60 $F_{254}$ (E. Merck, Darmstadt, Item no. 5729) without chamber saturation. If no detailed information is given as to the configuration, it is not clear whether it is a pure enantiomer or whether partial or even complete racemisation has occurred. The following eluants or mixtures of eluants were used for the chromatography:

El A=ethyl acetate/methanol 100/5 v/v

El B=ethyl acetate/methanol 80/20 v/v

El C=ethyl acetate/methanol/conc. ammonia 80/20/1 v/v/v

El D=dichloromethane/cyclohexane/methanol/conc. ammonia 350/75/75/10 v/v/v/v

El E=ethyl acetate/glacial acetic acid 99/1 v/v

El F=ethyl acetate/methanol/glacial acetic acid 90/10/1 v/v/v

El G=dichloromethane/methanol/conc. ammonia 90/10/1 v/v/v

El H=petroleum ether/ethyl acetate 1/1 v/v

El I=dichloromethane/methanol/glacial acetic acid 90/10/1.5 v/v/v

El K=dichloromethane/isopropanol 9/1 v/v

El L=ethyl acetate/methanol 9/1 v/v

El M=dichloromethane/methanol/conc. ammonia 75/25/5 v/v/v

El N=dichloromethane/ethyl acetate 1/1 v/v

El O=dichloromethane/methanol 95/5 v/v

The following abbreviations are used in the description of the experiments:

| | |
|---|---|
| Mp.: | melting point |
| (D): | (decomposition) |
| DIEA: | N,N-diisopropyl-ethylamine |
| Boc: | (1,1-dimethylethoxy)carbonyl |
| TBTU: | 2-(1H-benzotriazol-1-yl)-1,1,3,3-tetramethyluronium-tetrafluoroborate |
| HOBt: | 1-hydroxybenzotriazole-hydrate |
| CDT: | 1,1'-carbonyldi-(1,2,4-triazole) |
| THF: | tetrahydrofuran |
| DMF: | dimethyl formamide |
| EE: | ethyl acetate |
| PE: | petroleum ether |
| LM: | solvents |
| I. No. | Item number |

The meanings of the symbols consisting of letters and numbers used in the Examples are shown in the following summary:

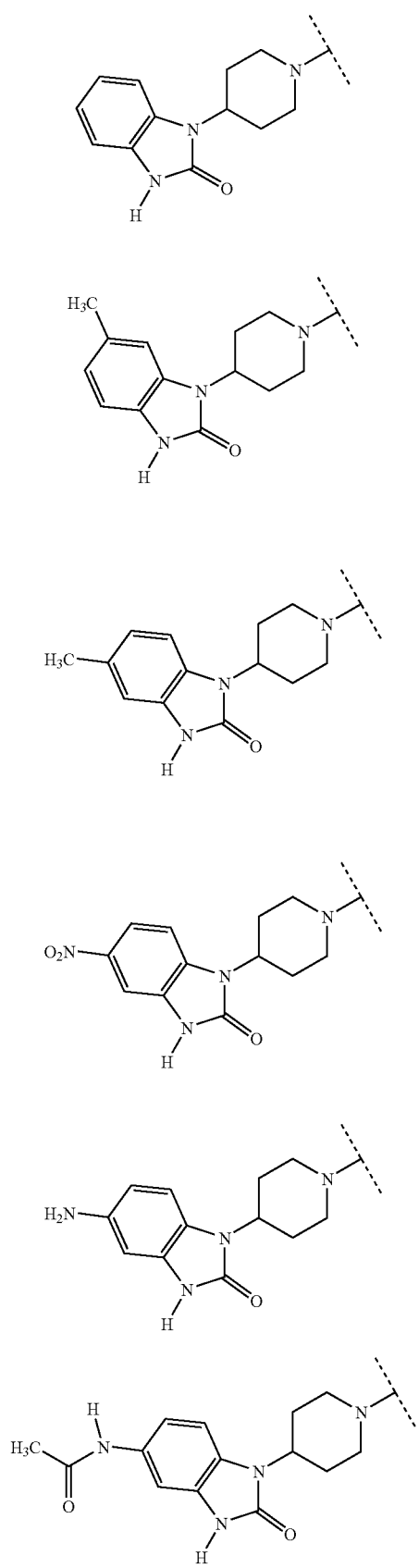
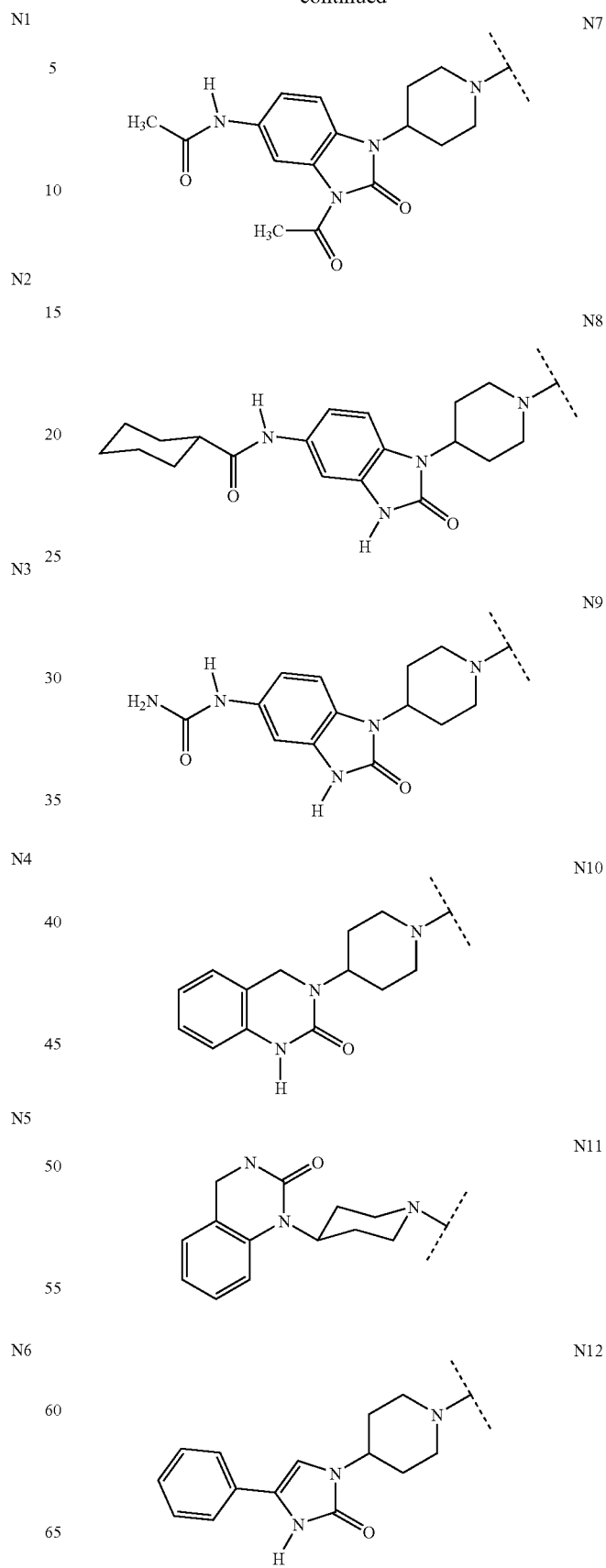

N13
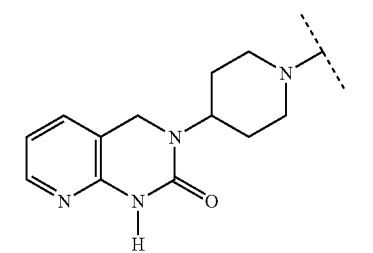
N14
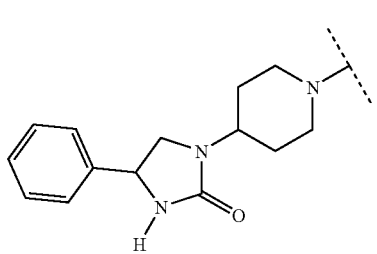
N15
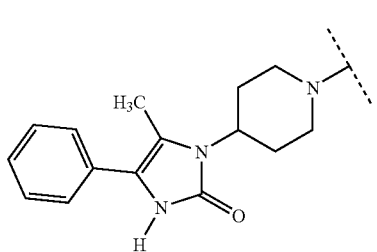
N16
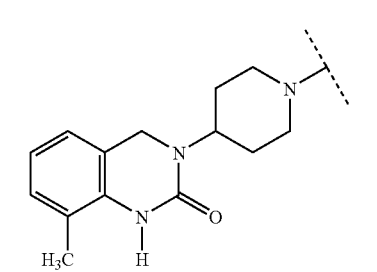
N17
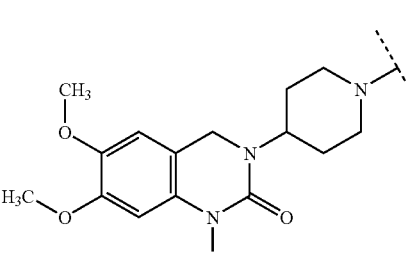
N18
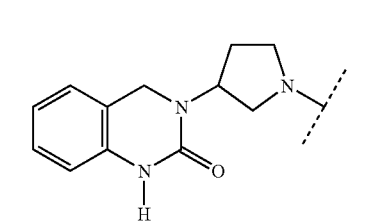
N19
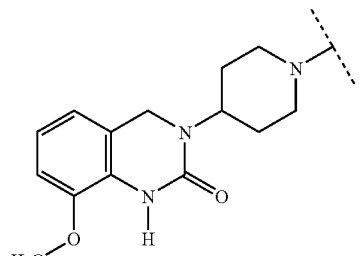
N20
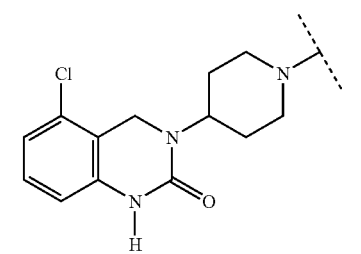
N21
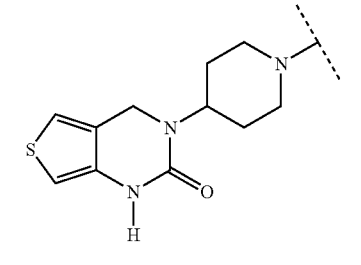
N22
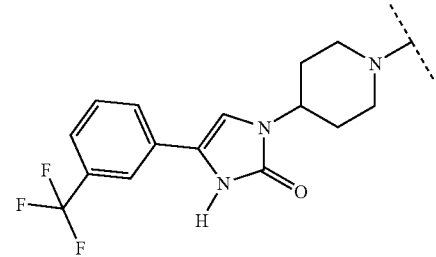
N23
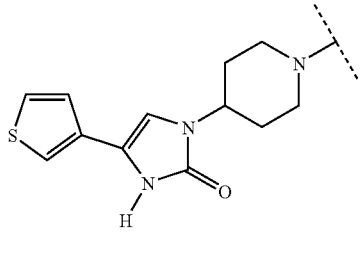
N24
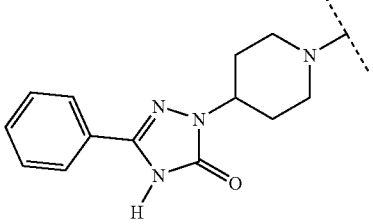

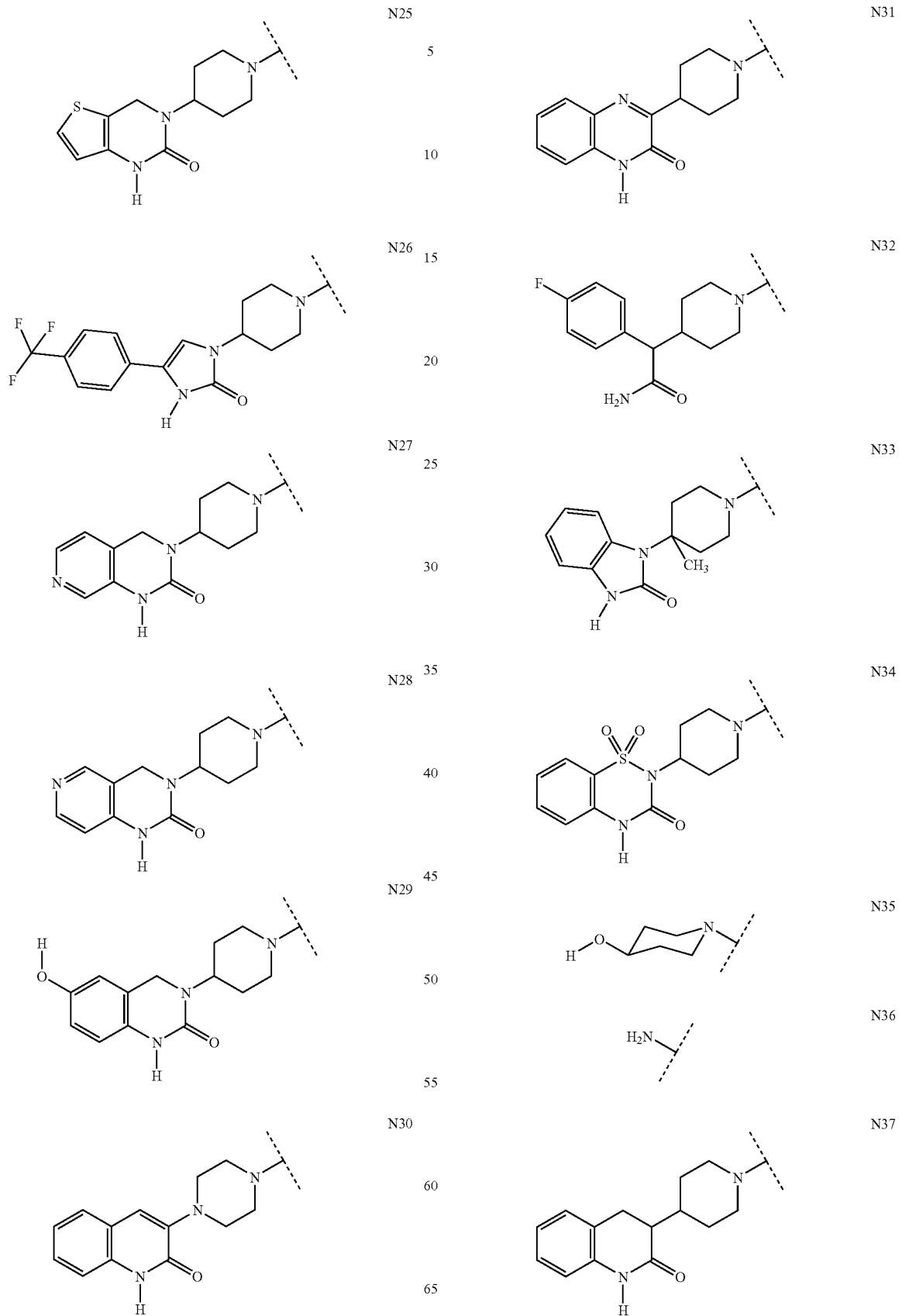

-continued
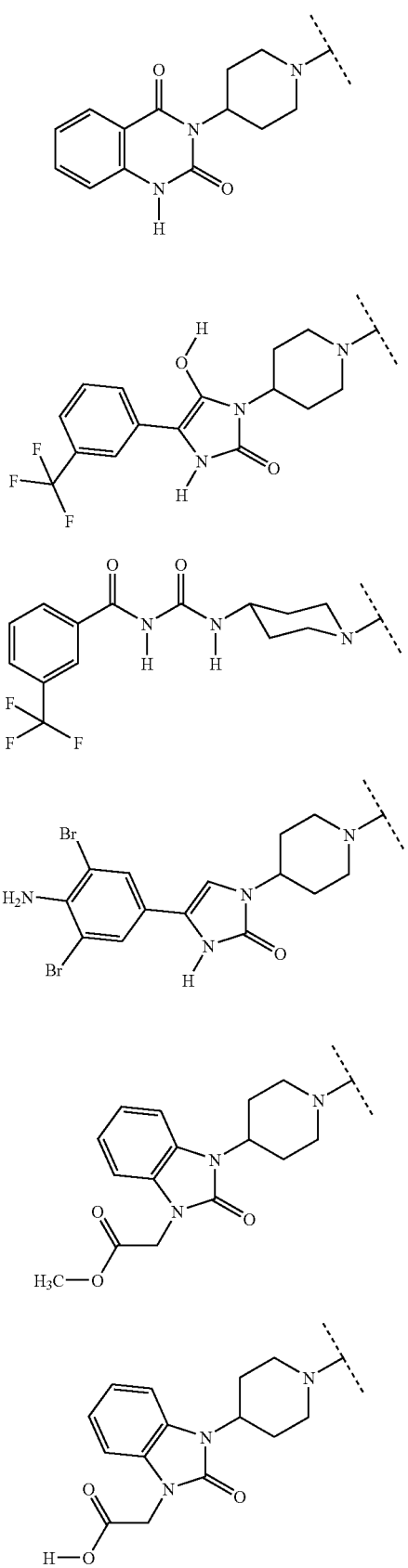
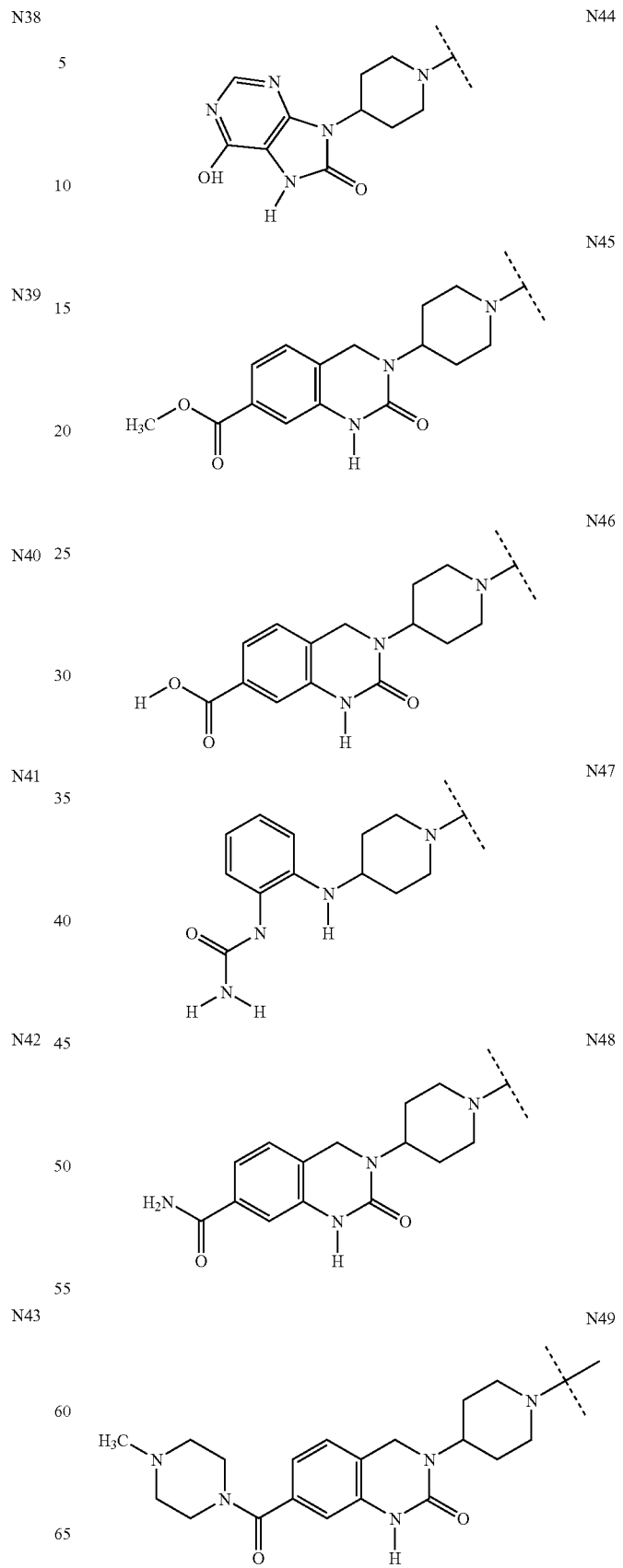

-continued
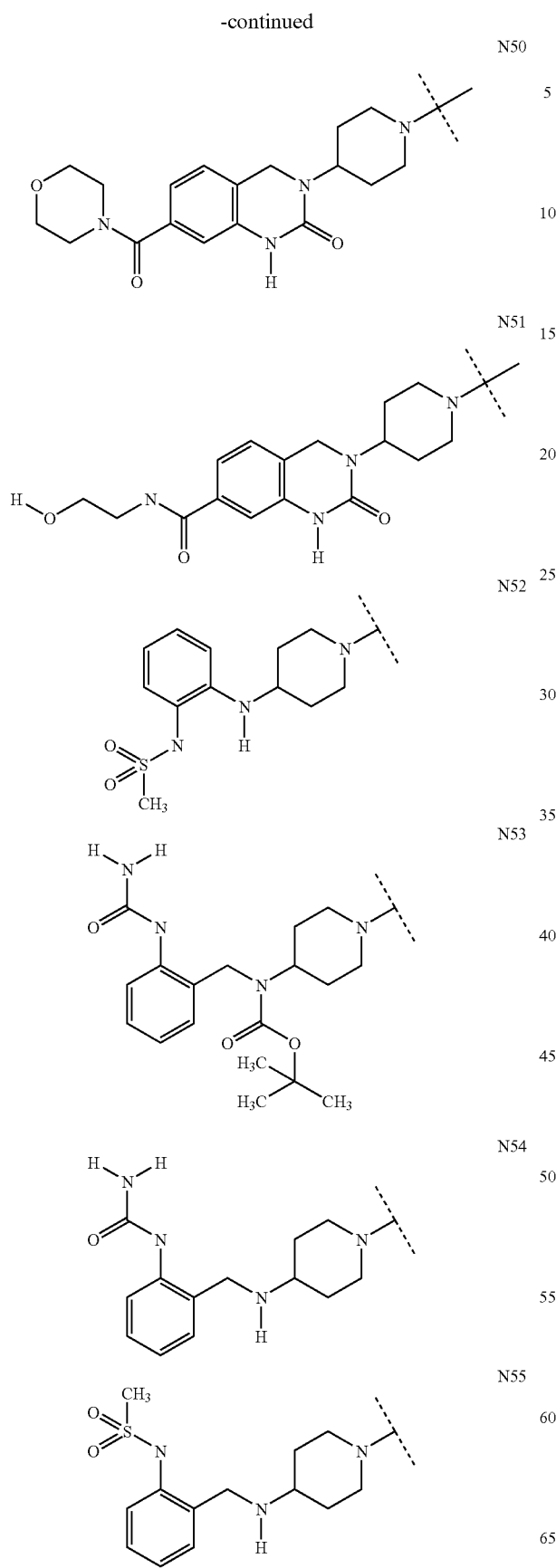
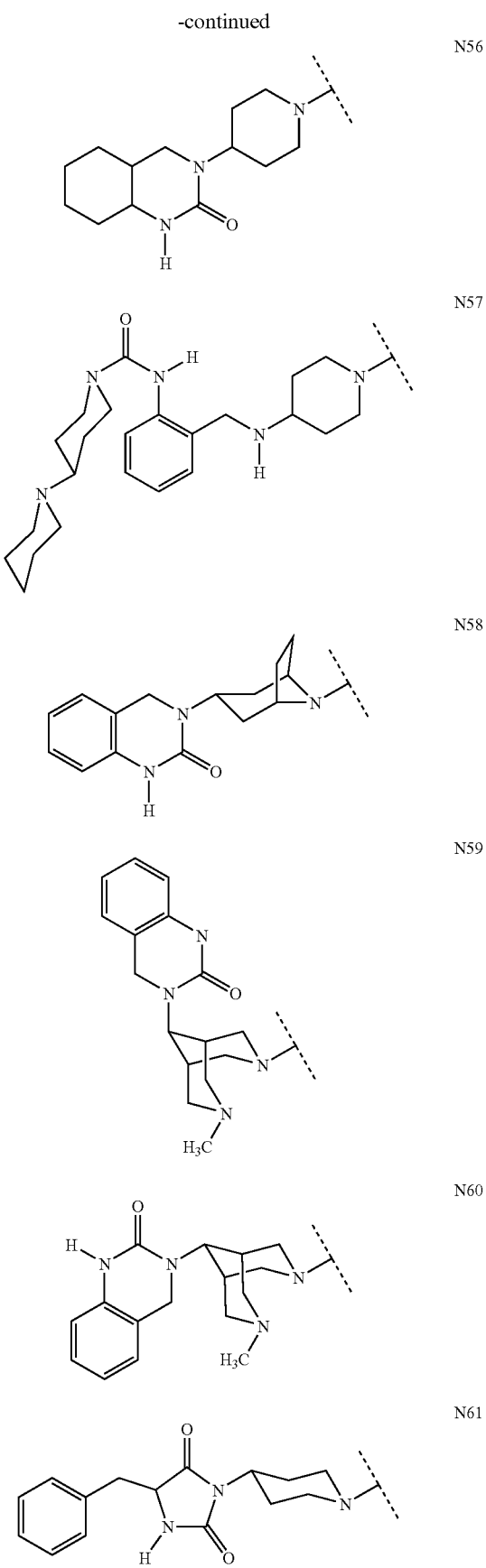

-continued
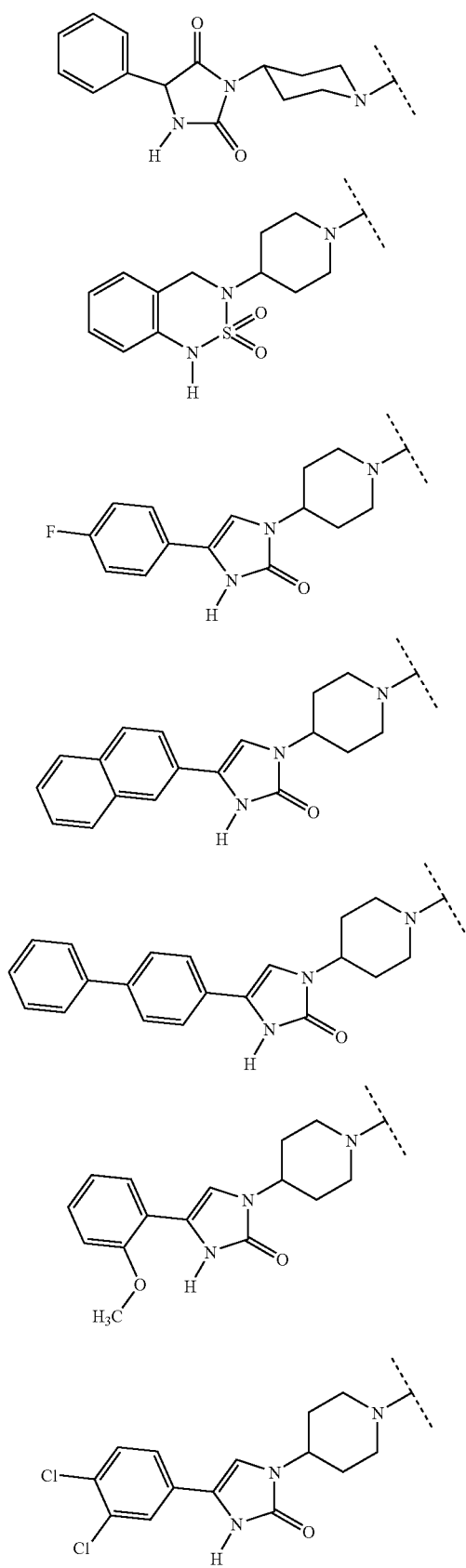
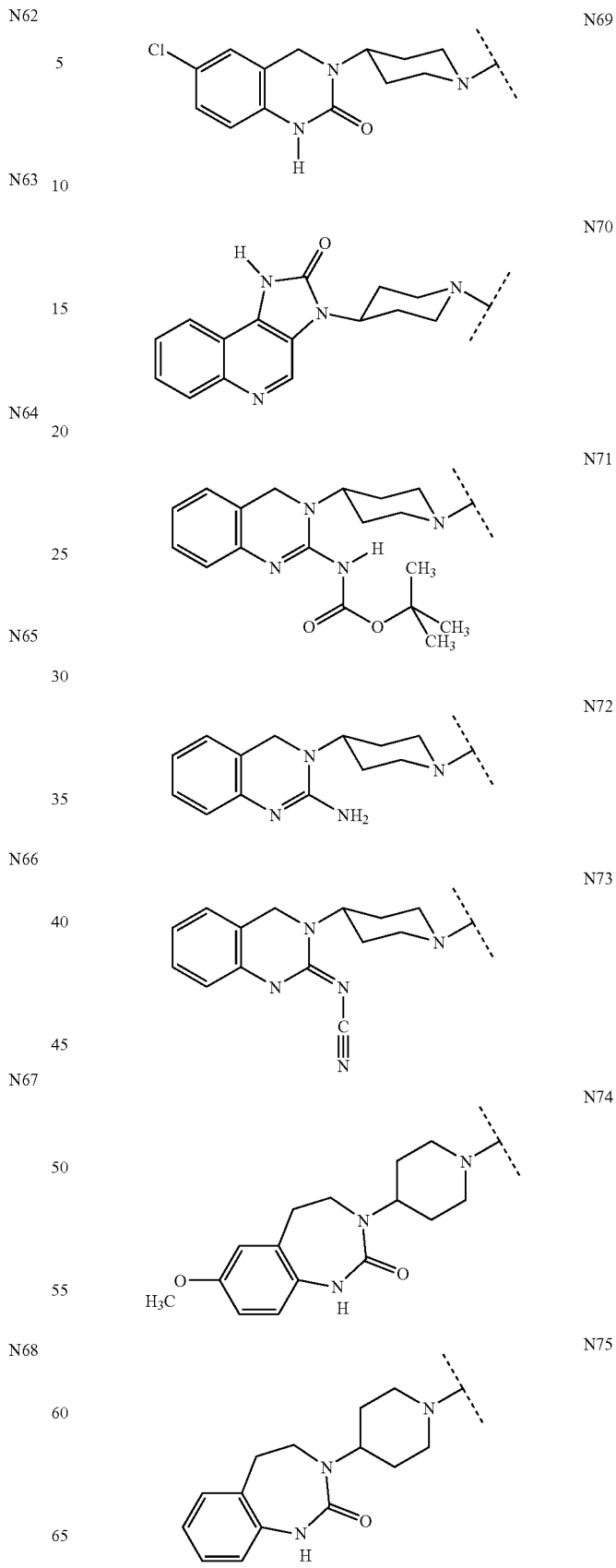

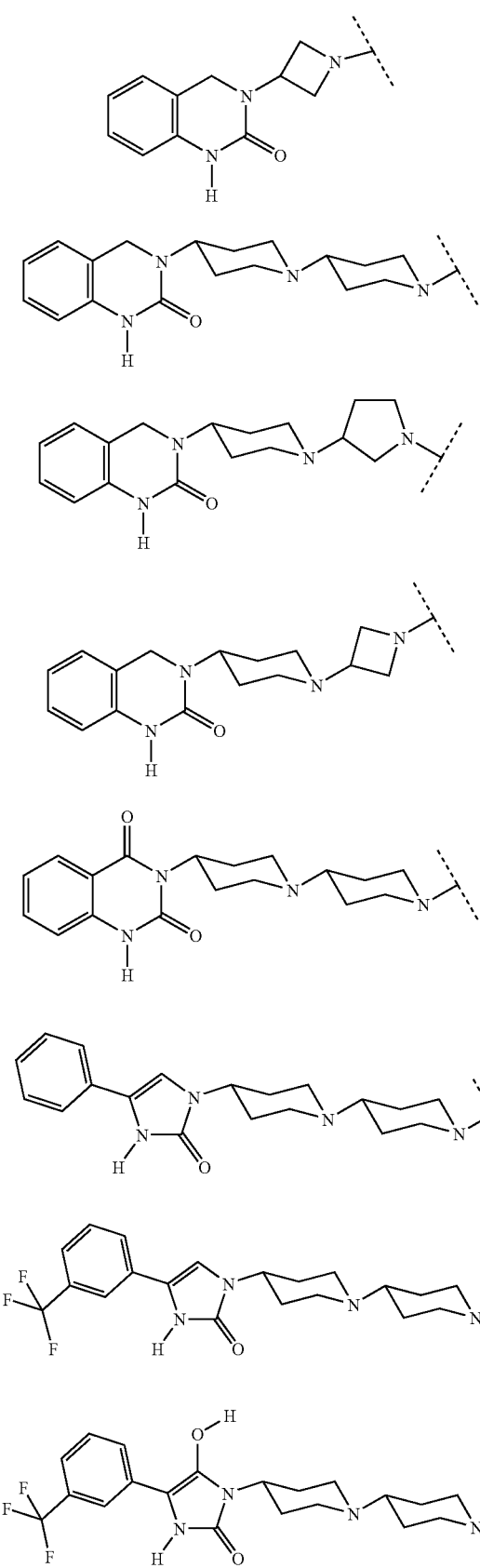
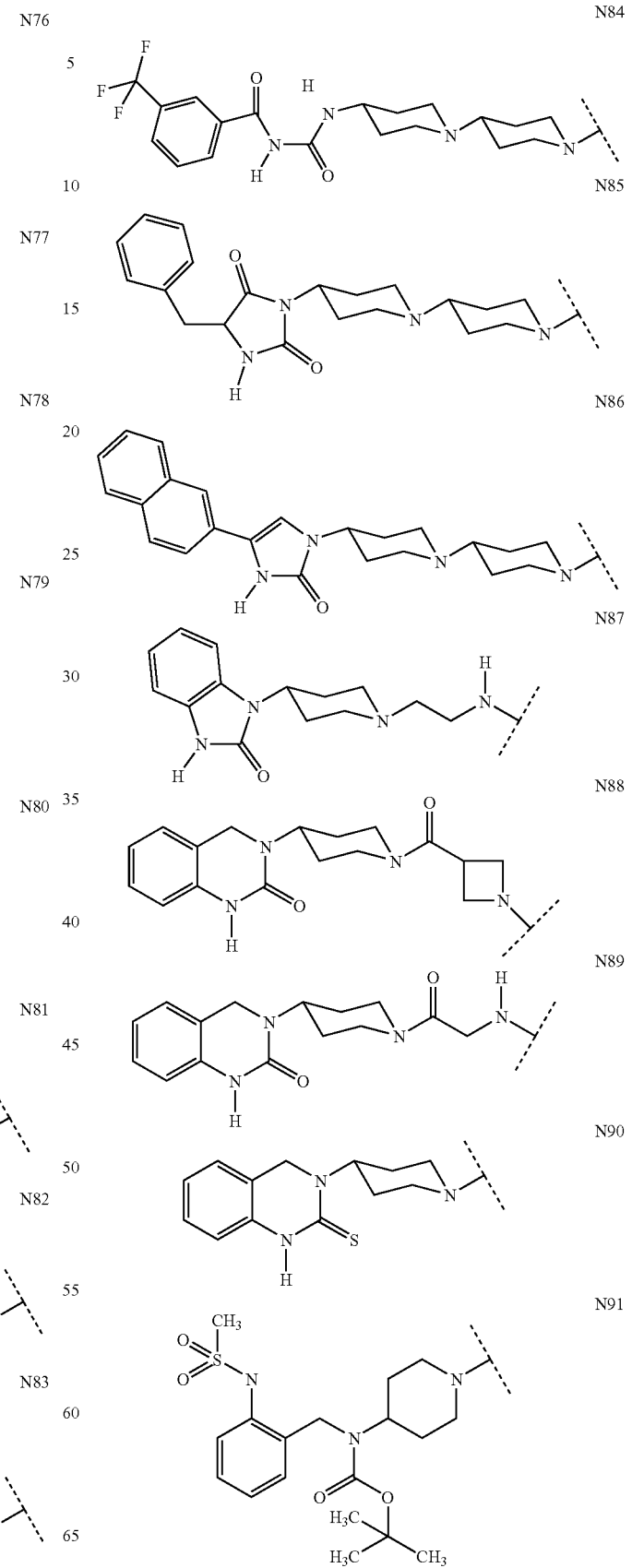

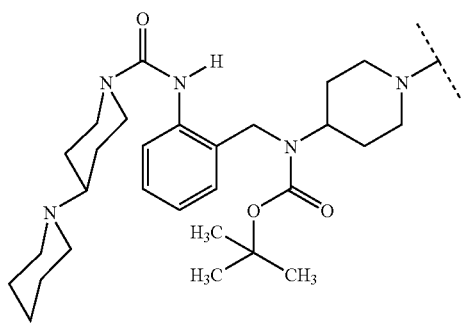
N92
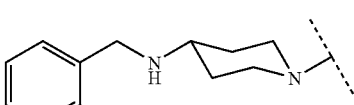
N93
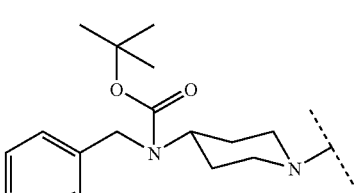
N94
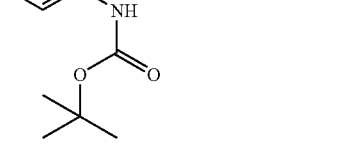
N95
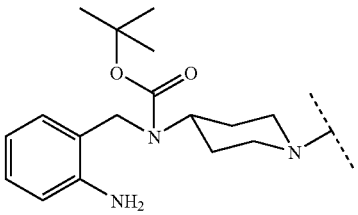
N96
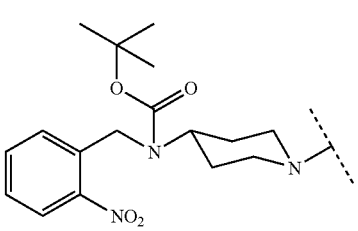
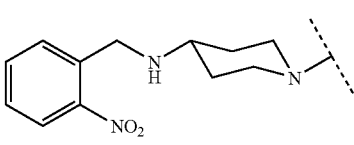
N97
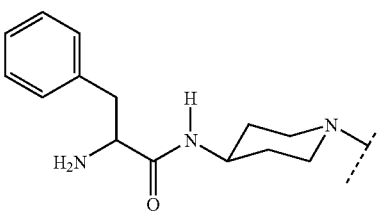
N98
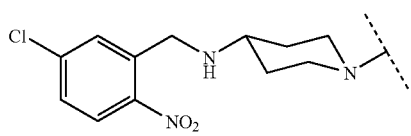
N99
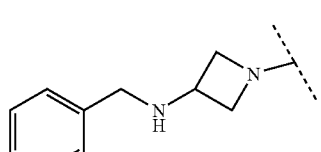
N100
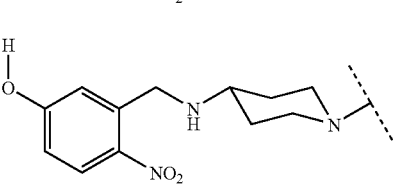
N101
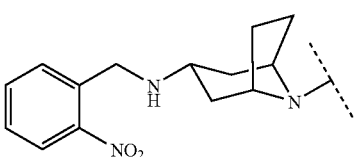
N102
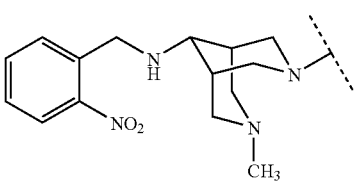
N103
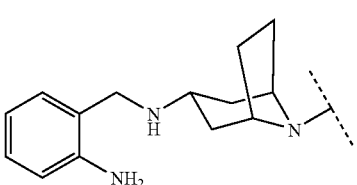
N104
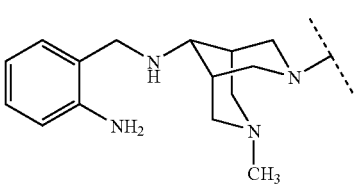
N105
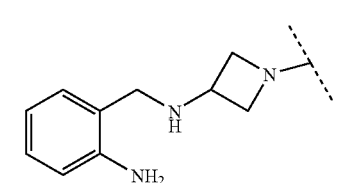
N106
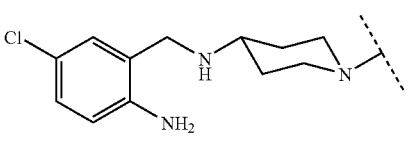
N107

-continued
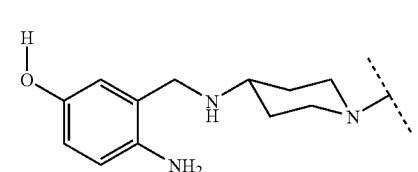 N108
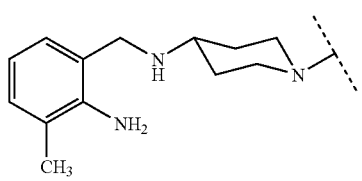 N109
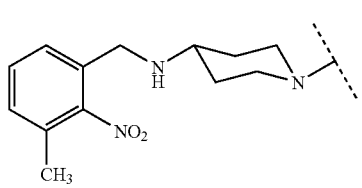 N110
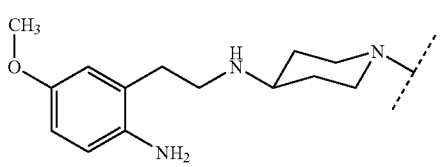 N111
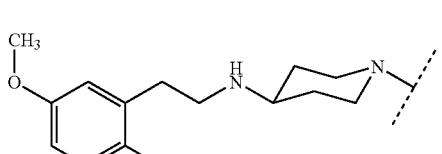 N112
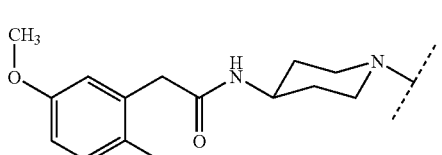 N113
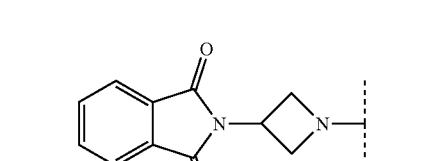 N114
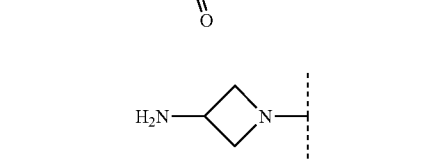 N115
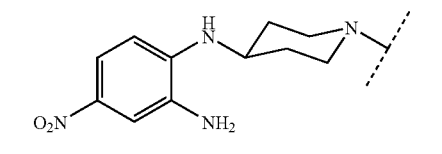 N116
-continued
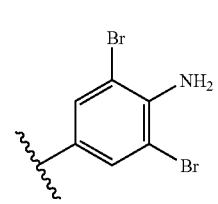 C1
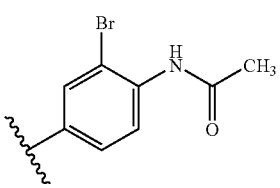 C2
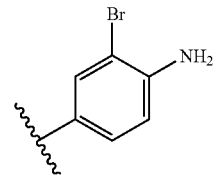 C3
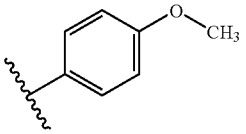 C4
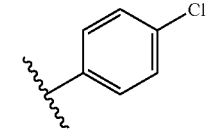 C5
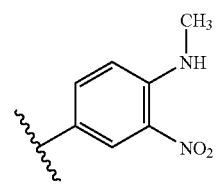 C6
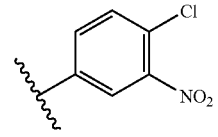 C7
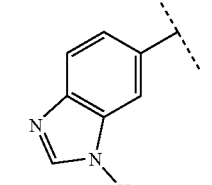 C8
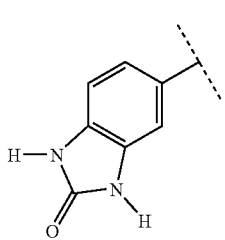 C9

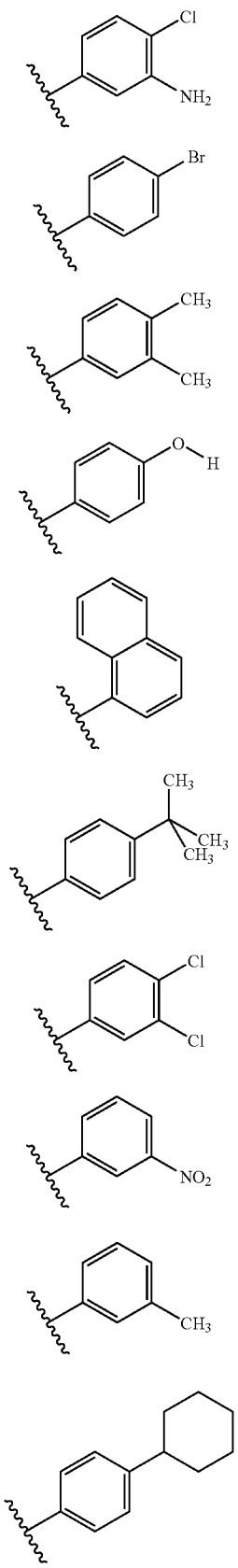
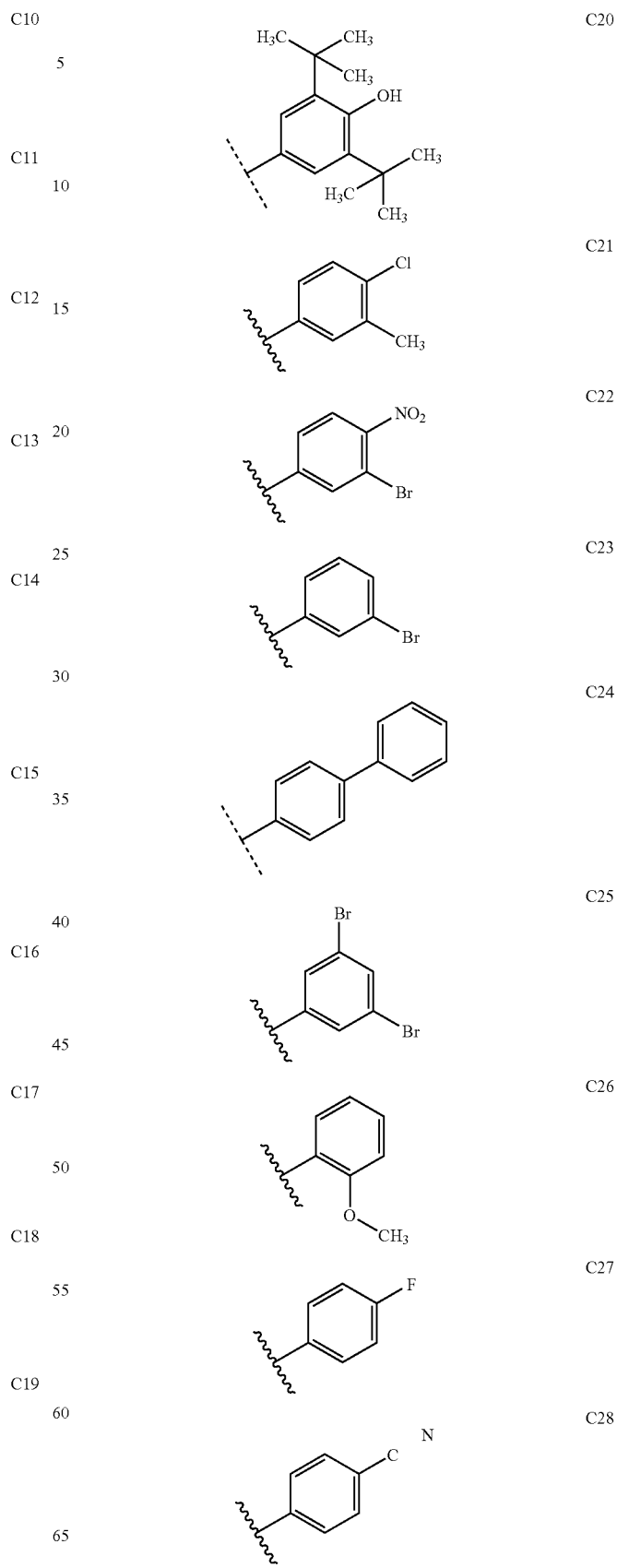

-continued
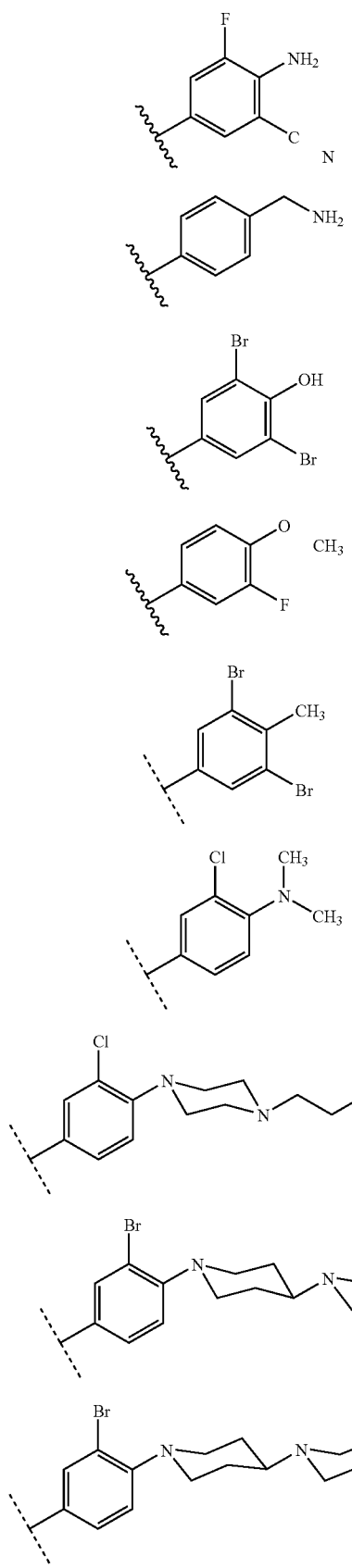
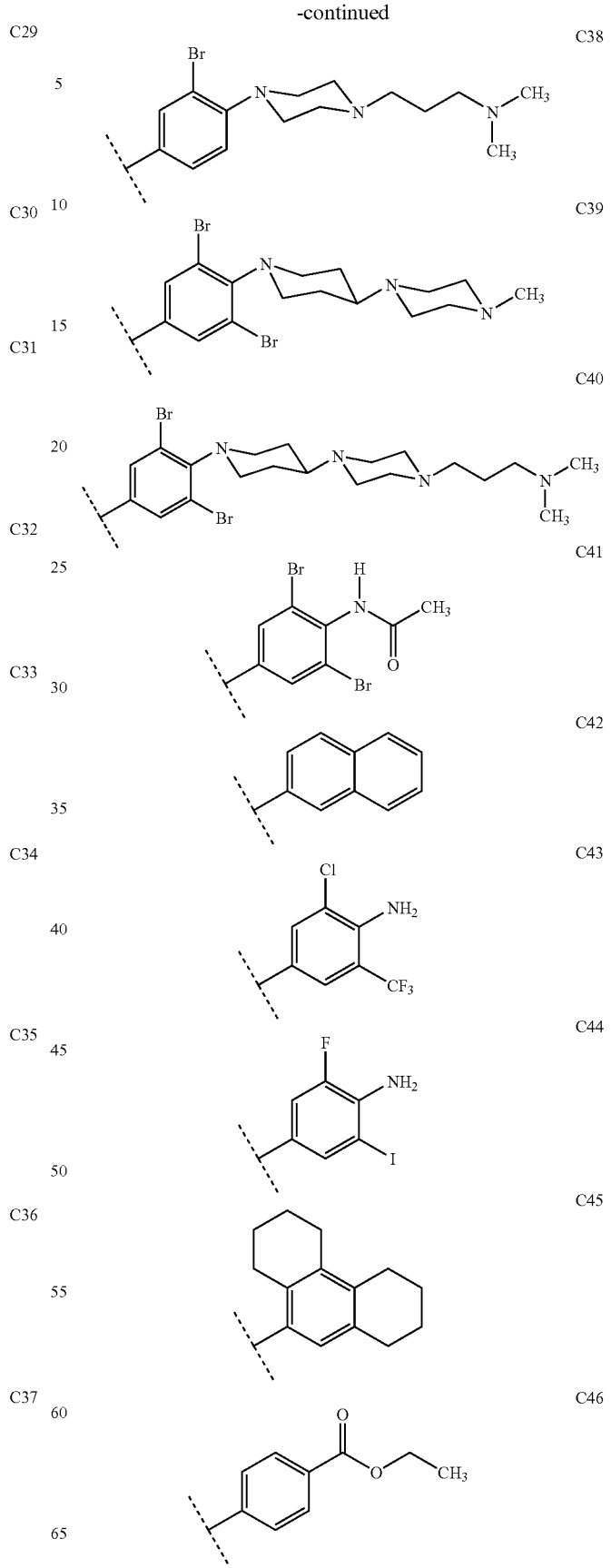

-continued
C47 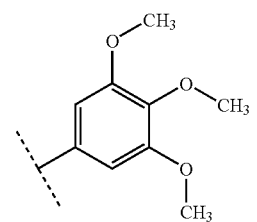
C48 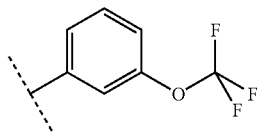
C49 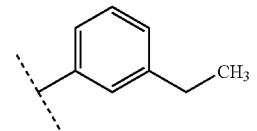
C50 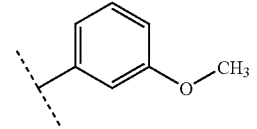
C51 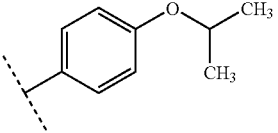
C52 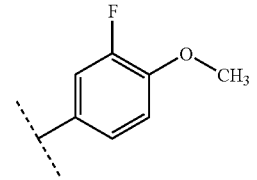
C53 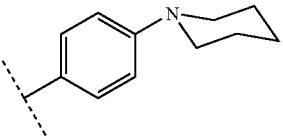
C54 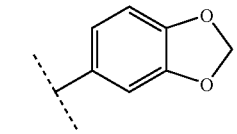
C55 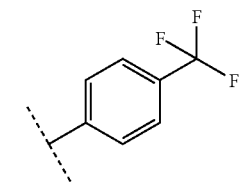
-continued
C56 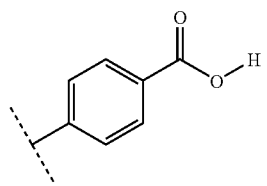
C57 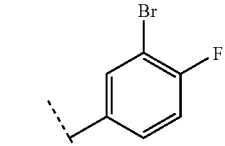
C58 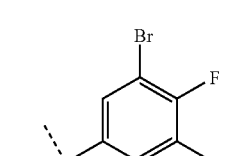
C59 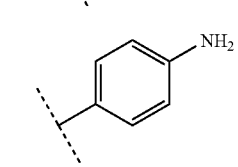
C60 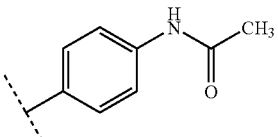
C61 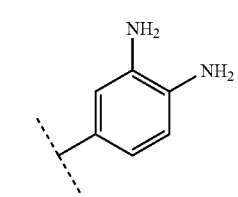
C62 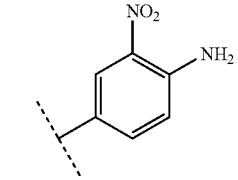
C63 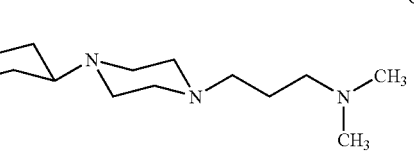
B1 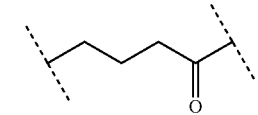

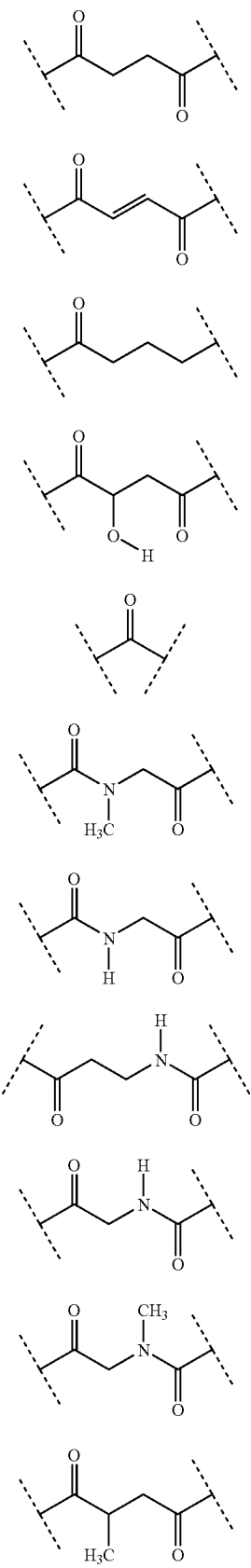

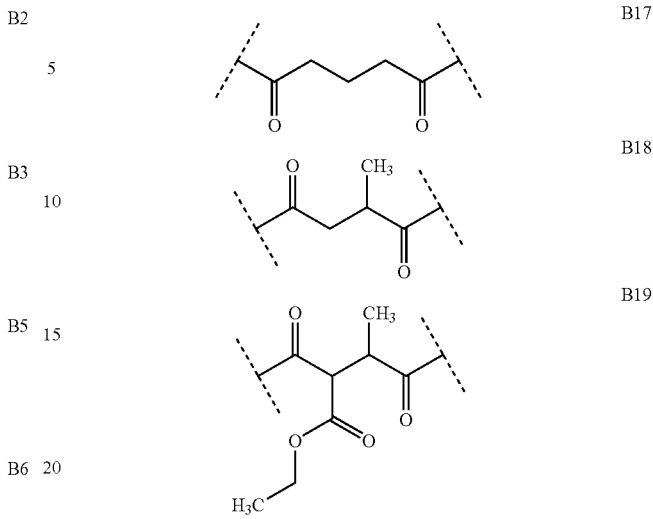

A. Preparation of Intermediate Compounds

EXAMPLE A1

1-(4-amino-3,5-dibromophenyl)-4-chloro-1-butanone 115 ml (2.107 mol) of bromine were added dropwise to a solution of 262 g (1.119 mol) of 1-(4-aminophenyl)-4-chloro-1-butanone-hydrochloride (base: m.p. 88–89° C. (decomp.), hydrochloride: m.p. 164–167° C. (decomp.), prepared by reacting 1-(4-acetylaminophenyl)-4-chloro-1-butanone with semi-concentrated hydrochloric acid) in a mixture of 1700 ml of glacial acetic acid and 850 ml of water, with stirring and external cooling with ice water. The precipitate formed was suction filtered, washed thoroughly twice with an ice-cold mixture of 170 ml of glacial acetic acid and 85 ml of water, then with pure water, and dried in vacuo at a temperature of 40° C. Yield: 293 g (74% of theoretical). M.p.: 83–84 C.

EXAMPLE A2

Preparation of compounds of the general structure:

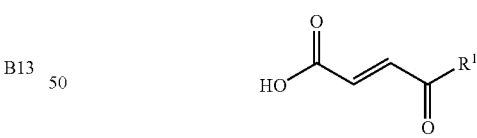

(E)-4-(3,5-dibromo-4-fluorophenyl)-4-oxo-2-butenoic acid

A mixture of 14.8 g (50.12 mmol) of 3,5-dibromo-4-fluoro-acetophenone, 6.9 g (74.92 mmol) of glyoxylic acid hydrate and 150 ml glacial acetic acid was refluxed for 20 hours. The glacial acetic acid was half distilled off, then water was added to the cooled mixture until a yellow precipitate was formed. The product precipitated was suction filtered, washed thoroughly with water and dried in a circulating air dryer until a constant weight was achieved. After recrystallisation from ethanol, 4.9 g (28% of theoretical) of slightly yellowish crystals were obtained, $R_f$ 0.82 (El F).

IR (KBr): 1705, 1672 (C=O)
MS: ESI: (M—H)⁻ = 348/350/352 (Br₂)

The following were obtained accordingly:

| N | B | C | Remarks | % yield | EI | Rf | MS | IR [cm-1] | m.p. [° C.] |
|---|---|---|---------|---------|----|----|----|-----------|-------------|
| OH | B3 | C11 | condensation with the addition of TsOH | 67 | | | | 1691, 1666 (C=O) | slightly yellowish crystals |
| OH | B3 | C12 | condensation with the addition of TsOH | 72 | | | | 1695, 1660 (C=O) | slightly yellowish crystals |
| OH | B3 | C13 | condensation with the addition of TsOH | 55 | | | M+ = 192 | 1695, 1653 (C=O) | slightly yellowish crystals |
| OH | B3 | C14 | condensation with the addition of TsOH | 51 | | | | 1701, 1668 (C=O) | slightly yellowish crystals |
| OH | B3 | C15 | condensation with the addition of TsOH | 79 | | | | 1697, 1662 (C=O) | slightly yellowish crystals |
| OH | B3 | C16 | | 52 | | | M+ = 243/245/247 (Cl2) | 1709, 1689, 1666 (C=O) | 139–141 (EtOH); yellow |
| OH | B3 | C17 | condensation with the addition of TsOH | 59 | | | | 1697, 1678 (C=O) | orange crystals |
| OH | B3 | C18 | condensation with the addition of TsOH | 66 | | | | 1705, 1687, 1666 (C=O) | slightly yellowish crystals |
| OH | B3 | C19 | condensation with the addition of TsOH | 86 | | | | 1699, 1664 (C=O) | slightly yellowish crystals |
| OH | B3 | C20 | condensation with the addition of TsOH | 82 | | | | 1703, 1660 (C=O) | slightly yellowish crystals |
| OH | B3 | C21 | condensation with the addition of TsOH | 73 | | | | 1712, 1691, 1664 (C=O) | slightly yellowish crystals |
| OH | B3 | C22 | condensation with the addition of TsOH | 65 | | | M+ = 299/301 (Br) | 1707, 1678 (C=O); 1520, 1358 (NO2) | orange-yellow crystals |
| OH | B3 | C23 | condensation with the addition of TsOH | 74 | | | | 1714, 1697, 1669 (C=O) | slightly yellowish crystals |
| OH | B3 | C26 | | 59 | | | | 1703.0, 1664.5 (C=O) | slightly yellowish crystals |
| OH | B3 | C27 | | 43 | | | | 1708.8, 1666.4 (C=O) | slightly yellowish crystals |
| OH | B3 | C28 | | 15 | | | | 2233.4 (CN); 1712.7, 1666.4 (C=O) | slightly yellowish crystals |
| OH | B3 | C29 | | 4 | | | M+ = 234 | 3429.2, 3350.2 (NH2); 2229.6 (CN); 1697.3, 1647.1 (C=O) | slightly yellowish crystals |
| OH | B3 | C1 | | 21 | | | | | slightly yellowish crystals |
| OH | B3 | C33 | condensation with the addition of TsOH | 78 | | | | 1701, 1674 (C=O) | 210–215; yellow crystals |
| OH | B3 | C34 | condensation with the addition of TsOH | 33 | | | (M + H)+ = 252.1, 254.1 (Cl) | 1711, 1662 (C=O) | slightly yellowish crystals |
| OH | B3 | C46 | condensation with the addition of TsOH | 31 | | | | | yellow crystals |
| OH | B3 | C47 | condensation with the addition of TsOH | 36 | | | | | yellow crystals |

| N | B | C | Remarks | % yield | EI | Rf | MS | IR [cm−1] | m.p. [° C.] |
|---|---|---|---|---|---|---|---|---|---|
| OH | B3 | C48 | condensation with the addition of TsOH | 64 | | | | | slightly yellowish crystals |
| OH | B3 | C49 | condensation with the addition of TsOH | 72 | | | | | slightly yellowish crystals |
| OH | B3 | C50 | condensation with the addition of TsOH | 33 | | | | 1700, 1670 (C=O) | slightly yellowish crystals |
| OH | B3 | C51 | condensation with the addition of TsOH | 54 | | | | 1701, 1664 (C=O) | yellow crystals |
| OH | B3 | C52 | condensation with the addition of TsOH | 32 | | | | 1707, 1662 (C=O) | yellow crystals |
| OH | B3 | C53 | condensation with the addition of TsOH | 50 | | | M+ = 259 | 1718 (C=O) | orange-yellow crystals |
| OH | B3 | C54 | condensation with the addition of TsOH | 34 | | | | | yellow crystals |
| OH | B3 | C55 | condensation with the addition of TsOH | 42 | E | 0.75 | | 1709, 1693, 1668 (C=O) | slightly yellowish crystals |
| OH | B3 | C57 | | 23 | F | 0.69 | M+ = 271/274 (Br) | 1709, 1689, 1664 (C=O) | 138–140; slightly yellowish |

EXAMPLE A3

Preparation of compounds of the general structure:

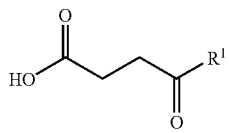

4-(3-bromo-4-fluorophenyl)-4-oxobutanoic acid

A solution of 6.2 g (0.023 mol) of (E)-4-(3-bromo-4-fluorophenyl)-4-oxo-2-butenoic acid in a mixture of 200 ml ethanol and 25 ml tetrahydrofuran was hydrogenated in the presence of 1.0 g of 10% platinum/charcoal at ambient temperature under a pressure of 50 psi until the uptake of hydrogen was complete. The residue remaining after the catalyst and solvent had been eliminated crystallised spontaneously and after being washed thoroughly with diisopropylether yielded 1.7 g (27% of theoretical) of colourless crystals, m.p. 108–110° C. and $R_f$ 0.73 (El F).

| | |
|---|---|
| IR (KBr): | 1711, 1687 (C=O) cm$^{-1}$ |
| MS: | ESI: (M—H)$^-$ = 273/275 (Br) |

The following were obtained accordingly:

| N | B | C | Remarks | % yield | EI | Rf | MS | IR [cm$^{-1}$] | m.p. [° C.] |
|---|---|---|---|---|---|---|---|---|---|
| OH | B2 | C26 | H$_2$/R–Ni/EE | 51 | | | | 1708.8, 1664.5 (C=O) | colourless crystals |
| OH | B2 | C27 | H$_2$/R—Ni/EE | 61 | | | | 1695.3, 1678.0 (C=O) | 88–90 (EtOH/H2O 1/2 v/v) |
| OH | B2 | C29 | H$_2$/R—Ni, EE/MeOH (2/3 v/v) | 90 | | | | 3494.8, 3375.2 (NH$_2$); 2223.8 (CN); 1714.6, 1674.1 (C=O) | colourless crystals |
| OH | B2 | C16 | H$_2$/Pd—C, EtOH/THF (10/1 v/v) | 37 | F | 0.78 | ESI: (M − H)$^-$ = 245/247/249 (Cl$_2$) | 1707, 1689 (C=O) | 157–159 |
| OH | B2 | C58 | H$_2$/Pt—C, EtOH/THF (5/1 v/v) | 55 | F | 0.88 | M$^+$ = 351/353/355 (Br$_2$) | 1705, 1689 (C=O) | colourless crystals |
| OH | B2 | C33 | H$_2$/Pt—C, EtOH/THF (10/1 v/v) | 99 | | | | 1701, 1684 (C=O) | colourless crystals |

EXAMPLE A4

4-(4-amino-3,5-dibromophenyl)-4-oxobutanoic acid

A solution of 73.7 g (0.461 mol) of bromine in 150 ml glacial acetic acid was added dropwise at ambient temperature to a solution of 50.0 g (0.213 mol) of 4-(4-adetylaminophenyl)-4-oxobutanoic acid in 500 ml of 80% acetic acid. The mixture was finally heated to 50° C. for a further 30 minutes. The precipitate formed after cooling was suction filtered, washed with diethylether and dried in a circulating air dryer at 40° C. The desired compound of m.p. 200–202° C. was obtained in a yield of 33.1 g (44% of theoretical).

| | |
|---|---|
| MS: | $M^+$ = 349/351/353 ($Br_2$) |
| IR (KBr): | 3487.1, 3382.9 ($NH_2$); 1701.1, 1672.2 (C=O) cm$^{-1}$ |

The following were obtained accordingly:

| N | B | C | remarks | % yield | EI | $R_f$ | MS | IR [cm$^{-1}$] | m.p. [° C.] |
|---|---|---|---|---|---|---|---|---|---|
| OH | B2 | C1 | 2 mol $Br_2$/80% AcOH | 44 | | | $M^+$ = 349/351/353 ($Br_2$) | 3487.1, 3382.9 ($NH_2$); 1701.1, 1672.2 (C=O) | 200–202 |
| $H_3CO$ | B2 | C1 | 2 mol $Br_2$/80% AcOH/NaOAc | 98 | | | | | colourless crystals (from MeOH) |
| OH | B2 | C2 | 1 mol $Br_2$/80% AcOH/NaOAc | 26 | | | $M^+$ = 313/315 (Br) | 3315.4 (NH), 1708.8, 1670.3 (C=O) | 186–187 (diisopropyl-ether) |
| OH | B5 | C1 | 2 mol $Br_2$/80% AcOH/NaOAc | 95 | | | | 1699.2 (C=O) | colourless crystals |
| OH | B5 | C2 | 1 mol $Br_2$/80% AcOH | 79 | | | | 3265.1 (NH), 1693.4, 1662.5 (C=O) | colourless crystals (from isopropanol/water 1/2 v/v) |
| OH | B17 | C1 | 2 mol $Br_2$/80% AcOH | 89 | | | | 3487, 3388 ($NH_2$); 1691, 1662 (C=O) | colourless crystals |
| OH | B18 | C1 | 2 mol $Br_2$/80% AcOH | 49 | F | 0.60 | | 3458.2, 3361.7 ($NH_2$); 1739.7 (C=O) | colourless crystals |
| OH | B15 | C1 | 2 mol $Br_2$/80% AcOH/NaOAc | 75 | | | ESI: $(M + H)^+$ = 363/365/367 ($Br_2$) | 1743 (C=O) | colourless crystals |

EXAMPLE A5

(3,5-dibromo-4-fluorophenyl)-ethanone and (3-bromo-4-fluorophenyl)-ethanone 69 g (0.5 mol) of p-fluoroacetophenone were added dropwise to 200.0 g (1.5 mol) of finely powdered aluminium chloride with stirring, during which time the mixture heated up to 70° C. It was kept at 75–80° C. for another 20 minutes and then 184 g (1.15 mol) of bromine were added at this temperature within 2.5 hours. Finally, the resulting mixture was heated to 90° C. for another 3 hours. After being cooled and decolorised the mixture was divided between water and tert.butylmethyl ether. Working up the organic phase yielded 130 g of a brownish-black oil which was separated into 2 fractions on silica gel using toluene as eluant:

a) 41.2 g (28% of theoretical) of colourless crystals, m.p. 59–62° C. and $R_f$=0.53 (toluene), which were identified as 1-(3,5-dibromo-4-fluorophenyl)-1-ethanone by spectroscopy.

| | |
|---|---|
| IR (KBr): | 1685 (C=O) cm$^{-1}$ |
| MS: | $M^+$ = 294/296/298 ($Br_2$) | b) 46.0 g (42% of theoretical) of colourless crystals, m.p. 52–55° C. and $R_f$=0.41 (toluene), which were identified as 1-(3-bromo-4-fluorophenyl)-1-ethanone by spectroscopy.

| | |
|---|---|
| IR (KBr): | 1682 (C=O) cm$^{-1}$ |
| MS: | $M^+$ = 216/218 (Br) |

The following was obtained accordingly:

| N | B | C | remarks | % yield | MS | IR [cm$^{-1}$] | m.p. [° C.] |
|---|---|---|---|---|---|---|---|
| — | $H_3CCO$ | C33 | $Br_2$/$AlCl_3$ | 76 | | 1685 (C=O) | 94–98 isopropanol |

EXAMPLE A6

γ-oxo-1H-benzimidazol-5-butanoic acid

Prepared analogously to Example 5 from methyl γ-oxo-1H-benzimidazol-5-butanoate, lithium hydroxide and water in the presence of tetrahydrofuran in a yield of 78% of theoretical. Colourless crystals, m.p. 251–255° C. (decomp.).

| | |
|---|---|
| IR (KBr): | 1672.2 (C=O) cm$^{-1}$ |

The following were obtained accordingly:

| N | B | C | remarks | % yield | IR [cm$^{-1}$] | m.p. [° C.] |
|---|---|---|---|---|---|---|
| OH | B2 | C1 | NaOH/dioxane/H$_2$O | 90 | 3485.2, 3382.9 (NH$_2$); 1701.1, 1672.2 (C=O) | colourless crystals |
| OH | B2 | C41 | NaOH/dioxane/H$_2$O | 89 | 3247.9 (NH); 1710.8, 1689.5 (C=O) | |
| H$_3$CO | B14 | C1 | NaOH/dioxane/H$_2$O | 55 | | |
| OH | B2 | C45 | NaOH/MeOH/H$_2$O | 96 | 1697, 1674 (C=O) | colourless crystals |
| OH | B2 | C9 | LiOH/THF/H$_2$O | 99 | 3356.6, 3223.2 (NH); 1718.5, 1689.5, 1660.6 (C=O) | colourless crystals |

EXAMPLE A7

4-(3,5-dibromophenyl)-4-oxobutanoic acid

A solution of 3.5 g (0.01 mol) of 4-(4-amino-3,5-dibromophenyl)-4-oxobutanoic acid in 50 ml of 1N aqueous sulphuric acid was treated dropwise with a solution of 0.76 g (0.011 mol) of sodium nitrite in 10 ml of water while maintaining a reaction temperature of −5 to 0° C. The mixture was stirred for a further 30 minutes at a temperature of 0° C., then 50 ml of hypo-phosphorous acid were added dropwise while maintaining the same temperature and stirred for another 1 hour at a temperature of 0° C. The mixture was decolorised and a colourless crystalline substance was precipitated. The mixture was diluted with 100 ml of water, the precipitate formed was suction filtered, washed thoroughly with water and then dried in a circulating air dryer. 3.1 g (92% of theoretical) of colourless crystals were obtained, m.p. 137–138° C.

| | |
|---|---|
| IR (KBr): | 1705.0 (C=O) cm$^{-1}$ |
| MS: | M$^+$ = 334/336/338 (Br$_2$) |

EXAMPLE A8

1-[[1.4']bipiperidinyl-4-yl]-1,3-dihydro-4-(3-trifluoromethyl-phenyl)-2(2H)-imidazolone-bis-(trifluoroacetate)

Prepared analogously to Example 7 from 1-[1'-(dimethylethoxy-carbonyl)-[1.4']bipiperidinyl-4-yl]-1,3-dihydro-4-(3-trifluoromethylphenyl)-2(2H)-imidazolone and trifluoroacetic acid in the presence of dichloromethane as solvent in a yield of 71% of theoretical. Colourless crystals.

| | |
|---|---|
| IR (KBr): | 1679.7 (C=O) cm$^{-1}$ |
| MS: | M$^+$ = 394 |

The following were obtained accordingly:

| N | B | C | remarks | % yield | EI | R$_f$ | MS | IR [cm$^{-1}$] | m.p. [° C.] |
|---|---|---|---|---|---|---|---|---|---|
| N87 | H | — | CF$_3$CO$_2$H/CH$_2$Cl$_2$ | 97 | | | | 1701.1, 1674.1 (C=O) | amorphous bis-(trifluoroacetate) |
| N81 | H | — | CF$_3$CO$_2$H/CH$_2$Cl$_2$ | 47 | | | M$^+$ = 326 | 1678 (C=O) | amorphous bis-(trifluoroacetate) |
| N93 | B2 | C1 | from N94-B2-C1 with CF$_3$CO$_2$H/CH$_2$Cl$_2$ | 59 | | | M$^+$ = 536/538/540 (Br$_2$) | | Colourless crystalline trifluoroacetate |
| N89 | H | — | CF$_3$CO$_2$H | 77 | | | M$^+$ = 288 | 1662.5 (C=O); 1207.4, 1176.5, 1132.1 (trifluoroacetate) | Colourless crystalline trifluoroacetate |
| N4 | H | — | CF$_3$CO$_2$H/CH$_2$Cl$_2$ | 37 | | | | 3292.3 (NH); 1714.6 (C=O); 1516.0, 1494.7, 1334.7 (NO$_2$) | |
| N85 | H | — | CF$_3$CO$_2$H/CH$_2$Cl$_2$ | 99 | | | | 1712, 1676 (C=O) | Colourless crystalline trifluoroacetate |

-continued

| N | B | C | remarks | % yield | EI | $R_f$ | MS | IR [cm$^{-1}$] | m.p. [° C.] |
|---|---|---|---|---|---|---|---|---|---|
| N86 | H | — | CF$_3$CO$_2$H/ CH$_2$Cl$_2$ | 96 | | | | | Colourless crystalline bis-(trifluoroacetate) |
| N98 | CH$_2$Ph | — | from Boc-N98-CH$_2$Ph and CF$_3$CO$_2$H/ CH$_2$Cl$_2$ | 92 | D | 0.68 | | 3485, 3379 (NH, NH$_2$); 1670.3 (C=O) | Colourless crystalline bis-(trifluoroacetate), from diisopropylether/ ethanol 9/1 v/v |
| N93 | CH$_2$Ph | — | from N95-CH$_2$Ph and CF$_3$CO$_2$H/ CH$_2$Cl$_2$ | 99 | D | 0.74 | | | |

EXAMPLE A9

4-amino-3-bromobenzenebutanoic acid

A mixture of 0.13 g (0.008662 mol) of 4-acetylamino-3-bromobenzenebutanoic acid and 10 ml of conc. hydrochloric acid was refluxed for 24 hours. The colourless, needle-shaped crystals of $R_f$ 0.53 (eluant: dichloromethane/methanol 9/1 v/v) precipitated after cooling were identified by spectroscopy as the hydrochloride of the desired 4-amino-3-bromobenzenebutanoic acid. The crystals were dissolved in a little water, and the solution formed was adjusted to pH 6 using concentrated potassium carbonate solution. The precipitate was suction filtered, washed with water and dried in a circulating air dryer at 60° C. Yield: 1.35 g (60% of theoretical).

IR (KBr): 3440.8, 3357.9 (NH); 1693.4 (C=O) cm$^{-1}$

The following was obtained accordingly:

| N | B | C | remarks | % yield | EI | $R_f$ | MS | IR [cm$^{-1}$] | m.p. [° C.] |
|---|---|---|---|---|---|---|---|---|---|
| OH | B17 | C59 | conc. HCl | 92 | | | | 3464, 3352 (NH); 1705, 1653 (C=O) | colourless crystals |
| OH | B18 | C59 | conc. HCl | 92 | I | 0.66 | | 3483.2, 3398.4, 3375.2 (NH$_2$); 1705.0, 1656.8 (C=O) | 170–172 (water) |
| OH | B15 | C59 | from ethyl 4-(4-aminophenyl)-2-ethoxycarbonyl-3-methyl-4-oxobutanoate; ethanolic HCl/semiconc. HCl 5/2 v/v | 60 | F | 0.8 | ESI: (M + H)$^+$ = 208 | 1712, 1689 (C=O) | |

EXAMPLE A10

3-{1-[4-(3,4-dichlorophenyl)-1,4-dioxobutyl]-4-piperidinyl}-3,4-dihydro-2(1H)-quinazolinone Prepared analogously to Example 2 from 3,4-dichloro-γ-oxobenzenebutanoic acid and 3-(4-piperidinyl)-3,4-dihydro-2(1H)-quinazolinone in the presence of TBTU in a yield of 73% of theoretical. Colourless crystals, m.p. 224–226° C. and $R_f$ 0.15 (El EE).

IR (KBr): 1666 (C=O) cm$^{-1}$
MS: ESI: (M + H)$^+$ = 482/484/486 (Cl$_2$)

The following were prepared accordingly:

| N | B | C | remarks | % yield | EI | $R_f$ | MS | IR [cm$^{-1}$] | m.p. [° C.] |
|---|---|---|---------|---------|-----|-------|-----|---------------|-------------|
| N10 | B2 | C57 | THF as solvent; DIEA as base | 73 | G | 0.75 | M$^+$ = 487/489 (Br); ESI: (M + Na)$^+$ = 510/512 (Br); (2M + Na)$^+$ = 997/999/1001 (Br) | 3205 (NH); 1666, 1645 (C=O) | colourless crystals |
| N10 | B2 | C58 | THF as solvent; DIEA as base | 78 | F | 0.82 | ESI: (M + Na)$^+$ = 588/590/592 (Br$_2$) | 1660 (C=O) | 212–215 |
| N94 | B2 | C1 | THF/DMF 5/1 as solvent; NEt$_3$ as base | 66 | H | 0.65 | M$^+$ = 736/738/740 (Br$_2$) | 3469, 3357 (NH, NH$_2$); 1751, 1691, 1649 (C=O) | |
| N89 | Boc | — | from N10-H and N-Boc-glycine, THF/DMF 1/1 as solvent; DIEA as base | 76 | | | M$^+$ = 388 | 3427.3, 3321.2 (NH, NH$_2$); 1722.3, 1666.4, 1645.2 (C=O) | 272–275 |
| N88 | Ph$_2$CH | — | from N10-H and 1-benzhydryl-azetidine-3-carboxylic acid; THF as solvent; DIEA as base | 64 | | | M$^+$ = 480 | 1664.5 (C=O) | hydrochloride: 164–165 |

EXAMPLE A11

4-acetylaminobenzenebutanoic acid

Prepared analogously to Example 10, but using ethanol as solvent, from 4-aminobenzenebutanoic acid and acetic anhydride in a yield of 62% of theoretical. Colourless crystals.

IR (KBr): 3342.4 (NH); 1714.6, 1643.4 (C=O) cm$^{-1}$

The following was obtained accordingly, but in the absence of a solvent and using p-toluenesulphonic acid as catalyst:

| N | B | C | remarks | % yield | MS | IR [cm$^{-1}$] | m.p. [° C.] |
|---|---|---|---------|---------|-----|---------------|-------------|
| H$_3$CO | B2 | C41 | Ac$_2$O/TsOH/130° C. | 38 | M$^+$ = 405/407/409 (Br$_2$) | | colourless crystals |

EXAMPLE A12

3-[1'-(1,1-dimethylethoxycarbonyl)-[1.4']bipiperidinyl-4-yl]-5-(phenylmethyl)-imidazolidin-2,4-dione A mixture of 5.5 g (20.2 mmol) of 3-(4-piperidinyl)-5-(phenylmethyl)-imidazolidin-2,4-dione, 4.0 g (20.1 mmol) of 1-(1,1-dimethylethoxycarbonyl)-4-piperidinone, 8 ml (20 mmol) of titanium(IV)-isopropoxide and 100 ml of anhydrous ethanol was stirred for 1 hour at ambient temperature. Then 0.89 g (13.45 mmol) of 95% sodium cyanoborohydride was added, the mixture was adjusted to pH 5 by the dropwise addition of glacial acetic acid and stirred overnight at ambient temperature. The mixture was stirred into 200 ml of water and freed from the precipitate formed. The filtrate was evaporated down in vacuo until no more ethanol passed over, the aqueous phase remaining was made alkaline with sodium hydroxide and extracted exhaustively with dichloromethane. Conventional working up of the extracts yielded 5.0 g (54% of theoretical) of colourless crystals.

| IR (KBr): | 1772, 1712 (C=O) cm$^{-1}$ |
|---|---|

The following were obtained accordingly:

| N | B | C | remarks | % yield | MS | IR [cm$^{-1}$] | m.p. [° C.] |
|---|---|---|---|---|---|---|---|
| N86 | Boc | — | from N65-H and N-Boc-4-piperidinone | 6 | | 1682, 1632 (C=O) | colourless crystals |
| N78 | CH$_2$Ph | — | from N10-H and N-benzyl-3-pyrrolidinone | 33 | M$^+$ = 390 | 3305 (NH); 1666 (C=O) | colourless crystals |
| N77 | Boc | — | from N12-H and N-Boc-4-piperidinone | 38 | M$^+$ = 426 | 3435 (NH); 1684 (C=O) | colourless crystals |
| N82 | Boc | — | from N22-H and N-Boc-4-piperidinone | 86 | M$^+$ = 494 | 1676, 1645 (C=O) | colourless crystals |
| N103 | CH$_2$Ph | — | from o-nitrobenzylamine and 7-methyl-3-(phenylmethyl)-3, 7-diazabicyclo[3.3.1]-nonan-9-one | 35 | M$^+$ = 380 | 3417.7 (NH); 1668.3 (C=O); 1355.9 (NO$_2$) | pale yellow oil |

EXAMPLE A13

N-(2-aminophenylmethyl)-N-(1,1-dimethylethoxy-carbonyl)-1-(phenylmethyl)-4-piperidineamine A solution of 60.6 g (278 mmol) of di-tert.butyldicarbonate in 400 ml of dioxane was added dropwise, within two hours, to a mixture of 80.0 g (270.8 mmol) of N-(2-aminophenylmethyl)-1-(phenylmethyl)-4-piperidineamine, 39.2 ml (280 mmol) of triethylamine, 500 ml of dioxane and 450 ml of water, while maintaining a reaction temperature of 5–10° C. The mixture was stirred for a further 3 hours while cooling externally with ice water, then for 60 hours at ambient temperature. The dioxane was distilled off in vacuo, and the aqueous residue was extracted exhaustively with a total of 1 l of ethyl acetate. The combined ethyl acetate extracts were washed once with 200 ml of water, twice with 250 ml of a saturated sodium hydrogen carbonate solution and once with 200 ml of water, dried over sodium sulphate and concentrated by evaporation in vacuo. The brownish oil remaining was taken up in 150 ml of diisopropylether and when left to stand colourless crystals were precipitated after about 15 hours, which were then suction filtered and dried. Yield: 31.5 g (29% of theoretical).

IR (KBr): 3438.8, 3363.7 (NH, NH$_2$); 1666.4, 1639.4 (C=O) cm$^{-1}$

The following were obtained accordingly:

| N | B | C | remarks | % yield | EI | R$_f$ |
|---|---|---|---|---|---|---|
| N96 | CH$_2$Ph | — | from N97-CH$_2$Ph and Boc$_2$O | 98 | K | 0.81 |
| N94 | CH$_2$Ph | — | from N95-CH$_2$Ph and Boc$_2$O | 98 | | |
| N71 | CH$_2$Ph | — | from N72-CH$_2$Ph and Boc$_2$O | 11 | | |

EXAMPLE A14

4-dimethylamino-3-chloroacetophenone

A mixture of 9.45 g (0.05 mol) of 3,4-dichloroacetophenone, 6.2 ml (0.1 mol) of dimethylamine and 2 ml of DIEA was stirred for 20 hours in an autoclave and at a reaction temperature of 120° C. After cooling the reaction mixture was divided between dichloromethane and water, the organic phase was washed with saturated sodium chloride solution, dried over sodium sulphate and concentrated by evaporation. The residue remaining was purified by column chromatography on silica gel, eluting first with toluene, then with tert.butyl-methyl ether. The appropriate eluates were combined and after working up in the usual way yielded 5.6 g (57% of theoretical) of the desired substance as a colourless oil.

IR (KBr): 1678 (C=O) cm$^{-1}$
MS: (M + H)$^+$ = 198/200 (Cl); (M + Na)$^+$ = 220/222 (Cl); (2M + Na)$^+$ = 417/419 (Cl)

The following was obtained accordingly:

| N | B | C | remarks | % yield | MS | IR [cm$^{-1}$] | m.p. [° C.] |
|---|---|---|---|---|---|---|---|
| N116 | Boc | — | from 1-(dimethylethoxy-carbonyl)-4-piperidineamine, 2-fluoro-5-nitroaniline and K$_2$CO$_3$ in DMSO/H$_2$O 4/1 v/v | 100 | | | reddish-brown oil |
| N4 | CH$_2$Ph | — | from 1-(phenylmethyl)-4-piperidineamine, N-(dimethylethoxy-carbonyl)-2-fluoro-5-nitroaniline in DMSO/100° C. | 82 | M$^+$ = 352 | | yellow crystals |

EXAMPLE A15

1-(Diphenylmethyl)-3-[(2-nitrophenylmethyl)amino]-azetidine

A mixture of 45.0 g (0.189 mol) of 3-amino-1-(diphenylmethyl)-azetidine, 28.7 g (0.190 mol) of 2-nitrobenzaldehyde and 280 ml of methanol was stirred for 3 hours at ambient temperature. Then 7.4 g (0.196 mol) of sodium borohydride were added followed, after a further 2 hours, by another 6.0 g of sodium borohydride and 300 ml of methanol and after a further 16 hours by 4.0 g of sodium borohydride, and the mixture was stirred for a further 4 hours at ambient temperature. The mixture was concentrated by evaporation in vacuo and the residue was treated with 200 ml dichloromethane and 200 ml of water. It was filtered, the methylene chloride phase was dried over sodium sulphate and freed from solvent. The residue was purified by chromatography on silica gel (30–60 μm) using dichloromethane/EE/MeOH/cyclohexane/conc. ammonia (59/25/7.5/7.5/1 v/v/v/v/v) as eluant, then on silica gel using dichloromethane/EE (1/1 v/v) as eluant. After the appropriate fractions had been worked up, 20.0 g (28% of theoretical) of the desired compound were obtained in the form of a pale yellow oil.

IR (KBr): 1342 ($NO_2$) $cm^{-1}$. MS: ESI: $(M+H)^+=374$; $(M+Na)^+=396$

The following were obtained accordingly:

| N | B | C | remarks | % yield | MS | m.p. [° C.] |
|---|---|---|---------|---------|----|----|
| N97 | $CH_2Ph$ | — | from 2-nitrobenzaldehyde, 4-amino-1-benzylpiperidine and $NaBH_4$/MeOH | 91 | | pale yellow oil |
| N99 | $CH_2Ph$ | — | from 5-chloro-2-nitrobenzaldehyde, 4-amino-1-benzylpiperidine and $NaBH_4$/MeOH | 92 | | pale yellow oil |
| N101 | $CH_2Ph$ | — | from 5-hydroxy-2-nitrobenzaldehyde, 4-amino-1-benzylpiperidine and $NaBH_4$/MeOH | 81 | M+ = 341 | 182; pale yellow crystals |
| N102 | $CH_2Ph$ | — | from 2-nitrobenzaldehyde, 8-(phenylmethyl)-8-azabicyclo[3.2.1]oct-3-ylamine and $NaBH_4$/MeOH | 76 | M+ = 351; ESI: $(M + H)^+$ = 352 | pale yellow oil |
| N110 | $CH_2Ph$ | — | from 3-methyl-2-nitrobenzaldehyde, 4-amino-1-benzylpiperidine and $NaBH_4$/MeOH | 100 | | |

EXAMPLE A16

3-[(2-aminophenylmethyl)amino]-1-(diphenylmethyl)-azetidine

A solution of 20.0 g (0.5355 mol) of 1-(diphenylmethyl)-3-[(2-nitrophenylmethyl)amino]-azetidine in 200 ml of methanol was hydrogenated in the presence of 4 g of 5% rhodium/charcoal for 5 hours at ambient temperature. The catalyst was filtered off, the filtrate was concentrated by evaporation in vacuo. 17.7 g (96% of theoretical) of a colourless, highly viscous oil were obtained, which was further processed without any additional purification.

| | |
|---|---|
| $R_f =$ | 0.75 (dichloromethane/EE/MeOH/cyclohexane/conc. ammonia 59/25/7.5/7.5/1 v/v/v/v/v) |
| MS: | $M^+$ = 343; ESI: $(M + H)^+$ = 344; $(M + Na)^+$ = 366 |

The following were obtained accordingly:

| N | B | C | remarks | % yield | EI | $R_f$ | IR [$cm^{-1}$] | m.p. [° C.] |
|---|---|---|---------|---------|-----|-------|-----|------|
| N93 | $CH_2Ph$ | — | from N97-$CH_2Ph$, $H_2$, 5% Rh—C, MeOH | 97 | D | 0.64 | | colourless oil |

-continued

| N | B | C | remarks | % yield | EI | $R_f$ | IR [cm$^{-1}$] | m.p. [° C.] |
|---|---|---|---------|---------|-----|-------|-----------------|-------------|
| N104 | CH$_2$Ph | — | rom N102-CH$_2$Ph, H$_2$, 5% Rh—C, MeOH | 68 | | | | colourless oil |
| N105 | CH$_2$Ph | — | from N103-CH$_2$Ph, H$_2$, 5% Rh—C, MeOH | 94 | | | | colourless oil |
| N107 | CH$_2$Ph | — | from N99-CH$_2$Ph, H$_2$, 5% Rh—C, MeOH | 95 | D | 0.74 | | colourless oil |
| N95 | CH$_2$Ph | — | from N96-CH$_2$Ph, H$_2$, 5% Rh—C, MeOH | 38 | D | 0.87 | | colourless crystals |
| N108 | CH$_2$Ph | — | from N101-CH$_2$Ph, H$_2$, 5% Rh—C, MeOH | 99 | D | 0.47 | 3338 (NH) | colourless crystals |
| H$_3$CO | B2 | C61 | from H$_3$CO-B2-C62, H$_2$, R—Ni, EE | 95 | | | 3458.2, 3408.0, 3357.9 (NH$_2$); 1732.0, 1706.9, 1658.7 (C=O) | 117 |
| N109 | CH$_2$Ph | — | from N110-CH$_2$Ph, H$_2$, 5% Rh—C, MeOH | 98 | D | 0.42 | | colourless oil |
| HO | B2 | C10 | from HO-B2-C7, H$_2$, Pt—C, MeOH | 20 | | | 3475.5, 3377.2 (NH$_2$); 1716.5, 1679.9 (C=O) | colourless crystals |
| N111 | CH$_2$Ph | — | from N112-CH$_2$Ph, H$_2$, 5% Rh—C, MeOH | 99 | D | 0.31 | | |

EXAMPLE A17

3-{[4-(3,4-dihydro-2(1H)-oxoquinazolin-3-yl)-1-piperidinyl]-carbonyl}-azetidine-hydrochloride A solution of 2.07 g (4.0033 mmol) of 1-(diphenylmethyl)-3-{[4-(3,4-dihydro-2(1H)-oxoquinazolin-3-yl)-1-piperidinyl]carbonyl}-azetidine-hydrochloride in a mixture of 100 ml of methanol and 2 ml of water was hydrogenated at a temperature of 50° C. and in the presence of 0.5 g of 10% palladium/charcoal until the uptake of hydrogen had ended. After removal of the catalyst and solvent 1.36 g (97% of theoretical) of the desired compound were obtained in the form of a colourless, porous substance.

| IR (KBr): | 1652.9 (C=O) cm$^{-1}$ |
|-----------|------------------------|
| MS:       | M$^+$ = 314            |

The following were obtained accordingly:

| N | B | C | remarks | % yield | EI | $R_f$ | MS | IR [cm$^{-1}$] | m.p. [° C.] |
|---|---|---|---------|---------|-----|-------|-----|-----------------|-------------|
| N53 | H | — | from N53-CH$_2$Ph, H$_2$, 10% Pd—C, MeOH | 83 | D | 0.07 | | 3433.1, 3323.2 (NH, NH$_2$); 1681.8 (C=O) | colourless crystals |
| N58 | H | — | from N58-CH$_2$Ph, H$_2$, 10% Pd—C, MeOH | 88 | D | 0.32 | | | colourless, amorphous |
| N59 | H | — | from N59-CH$_2$Ph, H$_2$, 10% Pd—C, MeOH | 83 | D | 0.18 | | | colourless oil |
| N60 | H | — | from N60-CH$_2$Ph, H$_2$, 10% Pd—C, MeOH, presumably a mixture of geometric isomers | 91 | | | | | colourless oil |
| N61 | H | — | from N61-CH$_2$Ph, H$_2$, 10% Pd—C, MeOH | 66 | D | 0.24 | | | crystals |
| N71 | H | — | from N71-CH$_2$Ph, H$_2$, 10% Pd—C, MeOH | 91 | D | 0.15 | | | colourless crystals |
| N92 | H | — | from N92-CH$_2$Ph, H$_2$, 10% Pd—C, MeOH | 52 | D | 0.42 | M$^+$ = 499 | 1687.6, 1660.6 (C=O) | colourless oil |
| N94 | H | — | from N94-CH$_2$Ph, H$_2$, 10% Pd—C, MeOH | 84 | | | | | colourless, amorphous |
| N79 | H | — | from N79-CHPh$_2$, H$_2$, 10% Pd—C, MeOH/ 1N aq. HCl (10/1 v/v) | 65 | D | 0.17 | ESI: (M + H)$^+$ = 287 | 1662 (C=O) | |
| N76 | H | — | from N76-CHPh$_2$, H$_2$, 10% Pd—C, MeOH/ 1N aq. HCl (2/1 v/v) | 20 | D | 0.22 | ESI: (M + H)$^+$ = 204 | | |
| N5 | H | — | from N4-CH$_2$Ph, H$_2$, 10% Pd—C, AcOH | 92 | | | | 3375.2, 3236.4 (NH, NH$_2$); 1678.0 (C=O) | colourless crystals |
| N16 | H | — | from N16-CH$_2$Ph, H$_2$, 20% Pd—C, MeOH | 99 | | | | | |
| N29 | H | — | from N29-CH$_2$Ph, H$_2$, 10% Pd—C, MeOH | 54 | | | | 3246 (NH); 1658 (C=O) | >260 (MeOH) |

| N | B | C | remarks | % yield | EI | $R_f$ | MS | IR [cm$^{-1}$] | m.p. [° C.] |
|---|---|---|---------|---------|----|----|----|----|----|
| N78 | H | — | from N78-CH$_2$Ph, H$_2$, 10% Pd—C, MeOH | 71 | M | 0.35 | | 3205 (NH); 1666 (C=O) | colourless crystals |
| N74 | H | — | from N74-CH$_2$Ph, H$_2$, 10% Pd—C, MeOH | 70 | M | 0.44 | ESI: (M + H)$^+$ = 276; (M − H)$^-$ = 276; (2M + H)$^+$ = 551; (2M − H)$^-$ = 549 | 3323, 3222 (NH); 2852, 2833 (OCH$_3$); 1658 (C=O) | colourless crystals |
| N91 | H | — | from N91-CH$_2$Ph, H$_2$, 10% Pd—C, MeOH | 96 | D | 0.18 | | 1689.5 (C=O); 1367.4, 1155.3 (SO$_2$—N) | colourless, amorphous |
| — | H | C63 | from PhCH$_2$-C63, H$_2$, 10% Pd—C, MeOH | 93 | | | ESI: (M + H)$^+$ = 255 | | colourless oil |

EXAMPLE A18

6-chloro-3,4-dihydro-3-(4-piperidinyl)-2(1H)-quinazolinone 2.17 g (15.178 mmol) of 1-chloroethyl chlorocarbonate were added to a solution of 4.5 g (12.645 mmol) of 6-chloro-3,4-dihydro-3-[(1-(phenylmethyl)-4-piperidinyl]-2(1H)-quinazolinone in 100 ml of anhydrous ethylene chloride and the mixture was refluxed for 1 hour. After the addition of 20 ml of methanol the mixture was refluxed for a further 3 hours. It was left to cool, 1.05 ml of 12M hydrochloric acid were added and the resulting mixture was evaporated down in vacuo. The residue was carefully triturated with petroleum ether and with diethylether one after the other. The crystals were taken up in a little water, the solution obtained was made clearly alkaline with sodium hydroxide solution and extracted exhaustively with EE. The combined ethyl acetate extracts were dried over potassium carbonate and brought to dryness in vacuo. The crystals remaining were triturated with diisopropylether and suction filtered. After drying in a circulating air dryer, 3.21 g (96% of theoretical) of colourless crystals were obtained.

EXAMPLE A19

Methyl 4-(1,3-dihydro-2(2H)-oxobenzimidazol-5-yl)-4-oxobutanoate

A mixture of 20.0 g (0.09 mol) of methyl 4-(3,4-diaminophenyl)-4-oxobutanoate, 16.2 g (0.1 mol) of N,N'-carbonyldiimidazole and 250 ml of tetrahydrofuran was heated to 60° C. with stirring for 90 minutes. After cooling the mixture was stirred into 500 ml of ice water, the precipitate formed was suction filtered and washed with diethylether. After drying in vacuo 14.85 g (67% of theoretical) of colourless crystals were obtained.

| IR (KBr): | 1728.1, 1699.2, 1674.1 (C=O) cm$^{-1}$ |
|---|---|

The following were obtained accordingly:

| N | B | C | remarks | % yield | EI | $R_f$ | MS | IR [cm$^{-1}$] | m.p. [° C.] |
|---|---|---|---------|---------|----|----|----|----|----|
| N58 | CH$_2$Ph | — | from N104-CH$_2$Ph and CDI in DMF | 18 | | | M$^+$ = 347 | 1664.5 (C=O) | |
| N59 | CH$_2$Ph | — | mixture of diastereomers, partly separable; from N105-CH$_2$Ph and CDI in DMF | 22 | | | ESI: (M + H)$^+$ = 377 | | colourless, amorphous |
| N69 | CH$_2$Ph | — | from N69-CH$_2$Ph and CDI in DMF | 46 | D | 0.84 | | | colourless crystals (acetone) |
| N61 | CH$_2$Ph | — | from N-[1-(phenylmethyl)-4-piperidinyl]-D,L-phenylglycinamide and CDI in DMF | 93 | D | 0.6 | M$^+$ = 363 | 3249.9 (NH); 1764.8, 1708.8 (C=O) | colourless crystals (diisopropylether) |
| N16 | CH$_2$Ph | — | from N109-CH$_2$Ph and CDI in DMF | 45 | | | | 1662.5 (C=O) | |
| N29 | CH$_2$Ph | — | from N108-CH$_2$Ph and CDI in DMF | 50 | | | | 1664 (C=O) | colourless crystals |
| N76 | CHPh$_2$ | — | from N106-CH$_2$Ph and CDI in DMF | 6 | | | | 1669 (C=O) | colourless crystals (diisopropylether) |
| N76 | CHPh$_2$ | — | from N106-CH$_2$Ph and CDI in DMF | 32 | | | | 3207 (NH); 1660 (C=O) | colourless crystals (diisopropylether) |
| N74 | CH$_2$Ph | — | from N111-CH$_2$Ph and CDI in DMF | 84 | D | 0.71 | | | colourless crystals |

| N | B | C | remarks | % yield | EI | $R_f$ | MS | IR [cm$^{-1}$] | m.p. [° C.] |
|---|---|---|---|---|---|---|---|---|---|
| N4 | Boc | — | from N116-Boc and CDI in THF | 6 | D | 0.57 | M$^+$ = 362 | | pale yellow crystals |

EXAMPLE A20

N-[(2-aminocarbonylaminophenyl)methyl]-N-(1,1-dimethylethoxy-carbonyl)-1-(phenylmethyl)-4-piperidineamine 2.0 g (0.03 mol) of sodium cyanate were added to a solution of 7.91 g (0.02 mol) of N-[(2-aminophenyl)methyl]-N-(1,1-dimethylethoxycarbonyl)-1-(phenylmethyl)-4-piperidineamine in a mixture of 5.5 ml glacial acetic acid and 80 ml of water and the mixture was stirred overnight at ambient temperature. The mixture was made slightly alkaline by the addition of saturated sodium hydrogen carbonate solution, then extracted exhaustively with EE. The combined ethyl acetate extracts were washed with water, dried over sodium sulphate and concentrated by evaporation in vacuo. 8.7 g (99% of theoretical) of colourless crystals were obtained, $R_f$ 0.71 (El D), which were further processed without any additional purification.

EXAMPLE A21

N-{2-{[1.4']bipiperidinyl-1'-ylcarbonylamino}phenylmethyl}-N-(1,1-dimethylethoxycarbonyl)-1-(phenylmethyl)-4-piperidineamine A mixture of 2.56 g (15.6 mmol) of CDT, 5.14 g (13 mmol) of N-[(2-aminophenyl)methyl]-N-(1,1-dimethylethoxycarbonyl)-1-(phenylmethyl)-4-piperidineamine and 200 ml of tetrahydrofuran was stirred for 0.5 hours while cooling with ice and then for 30 minutes at ambient temperature. 2.4 g (14.3 mmol) of [1,4']piperidinyl were added with stirring and the mixture was refluxed for 4 hours. The reaction mixture was diluted with 200 ml of ethyl acetate and the organic phase was washed twice with 150 ml of aqueous saturated sodium hydrogen carbonate solution and once with 100 ml of saturated aqueous sodium chloride solution. After the organic phase had been dried and the solvent eliminated in vacuo the residue was purified by column chromatography (MN-silica gel 60, Macherey-Nagel, 70–230 mesh ASTM, eluant: dichloromethane/isopropanol=9/1 (v/v)). 5.0 g (65% of theoretical) of a colourless amorphous product were obtained, $R_f$ 0.5 (El D).

IR (KBr): 1687.6, 1660.6 cm$^{-1}$ (C=O)

EXAMPLE A22

2-amino-3-[1-(phenylmethyl)-4-piperidinyl]-3,4-dihydro-quinazoline

A solution of 10.0 g (33.85 mmol) of N-[(2-aminophenyl)methyl]-1-(phenylmethyl)-4-piperidineamine in 150 ml of anhydrous ethanol was combined with 4.0 g (37.76 mmol) of bromocyanogen added batchwise. The mixture was left to stand overnight at ambient temperature, the ethanol was eliminated in vacuo and the residue was distributed between dichloromethane and 1N sodium hydroxide solution. After working up in the conventional way, 9.3 g (86% of theoretical) of colourless crystals were obtained, $R_f$ 0.4 (El D), which were further processed without any additional purification.

EXAMPLE A23

N-[2-(5-methoxy-2-nitrophenyl)ethyl]-1-(phenylmethyl)-4-piperidineamine 34.0 ml (268.2 mmol) of trimethylsilyl chloride were slowly added dropwise to a solution of 27.0 g (70.4 mmol) of 5-methoxy-2-nitro-N-[1-(phenylmethyl)-4-piperidinyl]-benzeneacetamide in 400 ml of anhydrous tetrahydrofuran and then stirred for another 1 hour at ambient temperature. 4.9 g (213.7 mmol) of lithium borohydride were added batchwise, stirring was continued for another 30 minutes at ambient temperature and then for 4 hours at reflux temperature. After cooling, 25 ml of water and 25 ml of semiconcentrated hydrochloric acid were added dropwise one after the other and the mixture was refluxed for 90 minutes. It was left to stand overnight at ambient temperature, then cooled in an ice bath and the precipitate formed was suction filtered. The aqueous phase of the filtrate was made ammoniacal and extracted exhaustively with EE. The combined ethyl acetate extracts were dried with sodium sulphate, then combined with ethereal hydrogen chloride solution until the precipitation ended. The product precipitated was combined with the earlier precipitate, presumed to be the dihydrochloride of the desired compound, suspended in ethanol and suction filtered. The filter cake was dissolved in 100 ml of water, the solution was made ammoniacal and extracted exhaustively with EE. Conventional, working up of the ethyl acetate extracts yielded a pale yellow oil, $R_f$ 0.69 (El D). Yield: 11.3 g (43% of theoretical).

| IR (KBr): | 1514, 1338 (NO$_2$) cm$^{-1}$ |
|---|---|
| MS: | ESI: (M + H)$^+$ = 370 |

EXAMPLE A24

5-methoxy-2-nitro-N-[1-(phenylmethyl)-4-piperidinyl]-benzene-acetamide 9.24 g (56.98 mmol) of N,N'-carbonyldiimidazole were added to a solution of 12.0 g (56.8 mmol) of 5-methoxy-2-nitrobenzene-acetic acid in 100 ml of tetrahydrofuran and the mixture was stirred for 40 minutes at a reaction temperature of 40° C. After the addition of 11.6 g (56.88 mmol) of 1-(phenylmethyl)-4-piperidineamine the mixture was heated to 40° C. for another hour. The reaction mixture was concentrated by evaporation in vacuo, the solid residue was digested with 50 ml of water and tert.butylmethylether, suction filtered and dried in a circulating air dryer at 50° C. 19.9 g (91% of theoretical) of pale yellow crystals were obtained, $R_f$ 0.6 (eluant: dichloromethane/EE/cyclohexane/methanol/conc. ammonia 300/80/25/25/3 v/v/v/v/v).

| IR (KBr): | 1638 (C=O) cm$^{-1}$ |
|---|---|
| MS: | ESI: (M + H)$^+$ = 384; (M + Na)$^+$ = 406; (M − H) = 382; (M − H + HCl) = 418/420 (Cl) |

EXAMPLE A25

4-(1,3-dihydro-2(2H)-oxo-1-benzimidazolyl)-1-{[2-[(1,1-di-methylethoxycarbonyl)amino]ethyl}piperidine A solution of 12.4 g (55.3 mmol) of 2-bromo-N-(1,1-dimethylethoxycarbonyl)-ethylamine in 50 ml tetrahydrofuran was added dropwise to a solution of 12.0 g (55.2 mmol) of 4-(1,3-dihydro-2(2H)-oxo-1-benzimidazolyl)piperidine and 15.3 ml (110.4 mmol) of triethylamine in 300 ml tetrahydrofuran. The mixture was refluxed for 20 hours and, after cooling, the triethylamine hydrobromide precipitated was eliminated. The remaining solution was concentrated by evaporation in vacuo, the residue was dissolved in 1 l of EE, the solution was washed twice with 200 ml of water, dried over sodium sulphate and evaporated down again. 11.7 g (59% of theoretical) of a colourless, waxy substance were obtained, which was used without any further purification.

| IR (KBr): | 3382.9 (NH); 1689.5 (C=O) cm$^{-1}$ |
|---|---|

EXAMPLE A26

3-[4-(3,4-dihydro-2(1H)-oxoquinazolin-3-yl)-1-piperidinyl]-1-(diphenylmethyl)-azetidine A mixture of 19.7 g (0.0621 mol) of 1-(diphenylmethyl)-3-mesyloxyazetidine, 14.4 g (0.0623 mol) of 3,4-dihydro-3-(4-piperidinyl)-2(1H)-quinazolinone, 100 ml of dimethylformamide and 12 ml of triethylamine was heated to a reaction temperature of 90° C. for 4 hours. The initially clear solution increasingly became a crystal slurry. After cooling the precipitate was suction filtered, crystallised once from 20 ml of hot dimethylformamide and the product was washed thoroughly with water and ethanol. After drying in a circulating air dryer 13.8 g (49% of theoretical) of colourless crystals were obtained, $R_f$ 0.76 (El D). IR (KBr): 1662 (C=O) cm$^{-1}$

EXAMPLE A27

N-(1,1-dimethylethoxycarbonyl)-N-[(2-methanesulphonylamino-phenyl)-methyl]-1-(phenylmethyl)-4-piperidineamine 1.64 ml. (21 mmol) of methanesulphonyl chloride was added dropwise to a solution of 7.91 g (20 mmol) of N-(1,1-dimethylethoxycarbonyl)-N-[(2-aminophenyl)methyl]-1-(phenylmethyl)-4-piperidineamine and 3.0 ml (21 mmol) of triethylamine in 100 ml of tetrahydrofuran and the mixture was then kept for 12 hours at ambient temperature. It was then diluted with 100 ml of EE and extracted twice with 70 ml of saturated sodium hydrogen carbonate solution. The ethyl acetate phase was dried over sodium sulphate and concentrated by evaporation in vacuo. 8.7 g (92% of theoretical) of a colourless substance were obtained, $R_f$ 0.85 (El D), which were used in the next step without any further purification.

EXAMPLE A28

4-(4-acetylaminophenyl)-2-methyl-4-oxobutanoic acid 22 ml (0.28 mol) of dimethylformamide were added dropwise to 133.34 g (1.0 mol) of finely powdered aluminium chloride within 20 minutes, while cooling externally with ice. After the strongly exothermic reaction died down, 13.517 g (0.1 mol) of acetanilide and 11.413 g (0.1 mol) of methylsuccinic acid anhydride were added all at once and at an initial temperature of 60° C., during which time the mixture heated up to about 80° C. It was kept for another 3 hours at a temperature of 60–70° C., the still hot mixture was stirred into 1 kg of crushed ice, 60 ml, of conc. hydrochloric acid were added and the mixture was left to stand overnight at ambient temperature. The precipitate formed was suction filtered and thoroughly washed with water. It was taken up in 150 ml of methanol, stirred for 30 minutes at 50° C., then for another 30 minutes while cooling externally with ice and the precipitate was suction filtered. After drying in a circulating air dryer at 60° C., 10.4 g (42% of theoretical) of colourless crystals were obtained, m.p. 229–231° C. and $R_f$ 0.48 (El I).

IR (KBr): 1714.6, 1662.5 cm$^{-1}$ (C=O)

The following were obtained accordingly:

| N | B | C | remarks | % yield | EI | $R_f$ | MS | IR [cm$^{-1}$] | m.p. [° C.] |
|---|---|---|---|---|---|---|---|---|---|
| H$_3$CO | B2 | C45 | from octahydrophenanthrene, 3-methoxycarbonyl-propionylchloride and AlCl$_3$/ethylene chloride | 50 | | | | 1730, 1675 (C=O) | 75–77 (petrol) |
| HO | B17 | C60 | from acetanilide, glutaric acid anhydride and AlCl$_3$/DMF | 12 | | | | 3336.7 (NH); 1708.8, 1674.1 (C=O) | colourless crystals (MeOH) |
| H$_3$CCHCl | B7 | C60 | from acetanilide, 2-chloropropionylchloride and AlCl$_3$/CH$_2$Cl$_2$ | 66 | H | 0.3 | ESI: (M − H)$^-$ = 224/226 (Cl) | 1670 (C=O) | |

EXAMPLE A29

Ethyl 4-(4-acetylaminophenyl)-2-(ethoxycarbonyl)-3-methyl-4-oxobutanoate 24.407 ml. (0.16 mol) of diethyl malonate were added dropwise to a suspension of 7.631 g (0.159 mol) of sodium hydride in 90 ml of anhydrous dimethylformamide under a nitrogen atmosphere, the mixture was heated for 90 minutes to 50° C., then 37.462 g (0.166 mol) of 1-(4-acetylaminophenyl)-2-chloro-1-propanone were added and heating was continued for a further 3 hours to 80° C. After cooling the mixture was stirred into 1 l of ice water, saturated with sodium chloride and extracted exhaustively with ethyl acetate. The combined ethyl acetate extracts were dried over sodium sulphate, filtered over activated charcoal and concentrated by evaporation in vacuo, and the residue was purified by column chromatography on silica gel. After working up in the usual way 45.0 g (80% of theoretical) of a colourless oil were obtained, $R_f$ 0.7 (El: EE). IR (KBr): 1747, 1732, 1676 cm$^{-1}$ (C=O) MS: M$^+$349

EXAMPLE A30

1-(4-amino-3,5-dibromophenyl)-2-methylamino-1-ethanone-hydrochloride

A solution of 10.2 g (0.027 mol) of 4-amino-3,5-dibromophenacyl bromide in 100 ml of dichloromethane was heated to 50° C. for 4 hours in a vibrating autoclave and in the presence of 3.64 ml (0.062 mol) of methylamine. After cooling the mixture was extracted three times with 50 ml of water, the dichloromethane phase was dried over sodium sulphate, then diluted with 300 ml of diethylether, and ethereal hydrochloric acid was added dropwise until the precipitation reaction had ended. The mixture was cooled overnight to −15° C., the precipitate was suction filtered and dried in a vacuum drying chamber at 40° C. Yield: 6.0 g (61% of theoretical).

MS: M$^+$=320/322/324 (Br$_2$); ESI: (M+H)$^+$=321/323/325 (Br$_2$). The product was used without purification, as the by-product detectable by mass spectroscopy (ESI: (M$_2$+H)$^+$=609/611/613/615/617/619 (Br$_4$)), presumably N,N'-bis-(4-amino-3,5-dibromophenacyl)-methylamine, was not expected to cause any complications in the subsequent reaction.

EXAMPLE A31

2-amino-1-(4-amino-3,5-dibromophenyl)-1-ethanone-hydrochloride 7.5 g (53.8 mmol) of urotropine were added to a solution of 20.0 g (53.8 mmol) of 4-amino-α,3,5-tribromoacetophenone in 600 ml of dichloromethane and stirred overnight at ambient temperature. The precipitate formed was suction filtered, washed with dichloromethane and dried in vacuo, then suspended in 600 ml ethanol. The mixture obtained was combined with 100 ml of conc. hydrochloric acid and refluxed for 2% hours. After cooling the precipitate formed was suction filtered, carefully washed with cold ethanol and dried in vacuo. Yield of colourless crystals: 18.5 g (100% of theoretical).

IR (KBr): 3477.5, 3431.2, 3323.2 (NH$_2$); 1679.9 (C=O) cm$^{-1}$

EXAMPLE A32

1-(Diphenylmethyl)-3-(phthalimido)-azetidine

A mixture of 75 g (0.235 mol) of 1-(diphenylmethyl)-3-(methanesulphonyloxy)-azetidine, 47.1 g (0.254 mol) of potassium phthalimide and 800 ml of dimethylformamide was refluxed for 1½ hours, during which time a fine precipitate gradually settled out. After cooling the precipitate was filtered off and the solvent was evaporated off in vacuo, finally under a high vacuum. The colourless residue crystallised when left to stand. Yield: 78.0 g (90% of theoretical). $R_f$=0.95 (El N).

EXAMPLE A33

3-amino-1-(diphenylmethyl)-azetidine 572 ml of 40% aqueous methylamine solution and 300 ml of water were added successively to a suspension of 78.0 g (0.212 mol) of 1-(diphenylmethyl)-3-(phthalimido)-azetidine in 480 ml of ethanol. After 7 days' stirring at ambient temperature a clear solution had formed, which was freed from excess methylamine and ethanol in vacuo. The aqueous solution remaining was extracted exhaustively with ethyl acetate. The ethyl acetate extracts were dried over sodium sulphate and dried in vacuo. 45.0 g (89% of theoretical) of a colourless oil were obtained, which was further processed without any additional purification.

EXAMPLE A34

4-[4-(methylamino)-3-nitrophenyl]-4-oxobutanoic acid

A solution of 20.0 g (0.0776 mol) of 4-(4-chloro-3-nitrophenyl)-4-oxobutanoic acid in 200 ml of 40% aqueous methylamine solution was stirred for 3 hours in a sealed vessel. Then the mixture was diluted with the same volume of water and acidified with acetic acid. The product precipitated was suction filtered, thoroughly washed with water and dried at 50° C. in a circulating air dryer. 18.5 g (95% of theoretical) of the desired compound were obtained in the form of yellow crystals.

EXAMPLE A35

4-(4-chloro-3-nitrophenyl)-4-oxobutanoic acid

While cooling externally with a mixture of ice and common salt, 21.3 g (0.1 mol) of 4-(4-chlorophenyl)-4-oxobutanoic acid were added batchwise to 100 ml of fuming nitric acid in such a way that the temperature of the mixture did not exceed 0° C. The mixture was stirred for another 1 hour at an internal temperature of between −5 and 0° C., then stirred into 1 l of ice water, after ½ hour the precipitate was collected on a filter, thoroughly washed with water until free from acid, and the crystalline product was dried in a circulating air dryer. 23.4 g (91% of theoretical) of pale yellow crystals were obtained.

EXAMPLE A36

Methyl 4-(1H-benzimidazol-5-yl)-4-oxobutanoate 75 ml of phosphorus(III)oxychloride were slowly added dropwise, while cooling externally with water, to a solution of 20.0 g (0.09 mol) of methyl 4-(3,4-diaminophenyl)-4-oxobutanoate in 50 ml of formic acid and the mixture was then stirred for another 40 minutes at a reaction temperature of 60° C. It was left to cool, then the mixture was stirred into 500 g of crushed ice while cooling externally with ice and made weakly ammoniacal. It was then extracted exhaustively with ethyl acetate, the combined extracts were dried over magnesium sulphate and concentrated by evaporation in vacuo. 8.29 g (40% of theoretical) of a colourless, crystalline substance were obtained. IR (KBr): 1732.0, 1679.9 cm$^{-1}$ (C=O)

EXAMPLE A37

1-(3-dimethylaminopropyl)-4-[1-(phenylmethyl)-4-piperidinyl]-piperazine

To a solution of 27.8 g (0.15 mol) of 1-(phenylmethyl)-4-piperidinone and 26.5 g (0.15 mol) of 1-(3-dimethylaminopropyl)-piperazine in 500 ml of tetrahydrofuran were added 200 mg of p-toluenesulphonic acid and 13.5 g (0.225 mol) of glacial acetic acid, followed by 47.7 g (0.225 mol) of sodium triacetoxyborohydride, in small batches, and the mixture was stirred overnight at ambient temperature. 100 ml of water were added dropwise while stirring was continued and after 30 minutes sufficient potassium carbonate was added to produce a precipitate that could be filtered off. It was filtered and the filter cake was washed thoroughly with THF and diethylether in succession. The combined filtrates were concentrated by evaporation in vacuo, the residue was purified by column chromatography on 400 g of aluminium oxide (Al$_2$O$_3$—ICN, activity stage 3) using EE/MeOH (95/5 v/v) as eluant. A colourless oil, R$_f$ 0.33 (El O), was obtained in a yield of 35.0 g (68% of theoretical). MS: ESI: (M+H)$^+$=345

B. Preparation of the Final Compounds

EXAMPLE 1

Preparation of compounds of general formula:

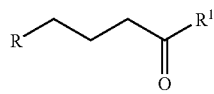

1-{1-[4-(4-amino-3,5-dibromophenyl)-4-oxobutyl]-4-piperidinyl}-1,3-dihydro-2(2H)-benzimidazolone-hydrochloride (Item no. 1)

A mixture of 30.6 g (0.0861 mol) of 1-(4-amino-3,5-dibromophenyl)-4-chloro-1-butanone, 18.6 g (0.0856 mol) of 1-(4-piperidinyl)-1,3-dihydro-2(2H)-benzimidazolone, 18.2 g (0.172 mol) of anhydrous sodium carbonate, 2.0 g of potassium iodide and 800 ml of methylisobutylketone was refluxed for 130 hours. After cooling the mixture was extracted once with 500 ml of water, the organic phase was dried over sodium sulphate and concentrated by evaporation in vacuo. The residue was dissolved in 50 ml of anhydrous ethanol and the equivalent amount of ethanolic hydrogen chloride solution was added dropwise. After standing for 24 hours at ambient temperature the colourless crystals precipitated were suction filtered and dried in vacuo. Yield: 27.0 g (55% of theoretical). M.p.: 297–299 C (decomp.) (ethanol/water 95/5 v/v). R$_f$ 0.21 (El A). C$_{22}$H$_{24}$Br$_2$N$_4$O$_2$*HCl (572.73) Calc.: C, 46.14; H, 4.40; Br, 27.90; Cl, 6.19; N, 9.78; Found: 45,10, 4.92, 27.65, 6.09, 9.95

The following were prepared analogously:

| Item no. | N | B | C | Ex. no. | remarks | % yield | EI | R$_f$ | MS | IR [cm$^{-1}$] |
|---|---|---|---|---|---|---|---|---|---|---|
| 2 | N2 | B1 | C1 | 1 | DMF/DMSO 2/1 as solvent; NEt$_3$ as base | 29 | A | 0.21 | m/e = 244; 257; 276 | 1687.6 (C=O) |
| 3 | N3 | B1 | C1 | 1 | DMSO as solvent; NEt$_3$ as base | 21 | A | 0.28 | ESI: (M + H)$^+$ = 549/551/553 (Br$_2$) | 1695.3 (C=O) |
| 4 | N4 | B1 | C1 | 1 | DMSO as solvent; NEt$_3$ as base | 48 | A | 0.53 | m/e = 288/289 | 1685.7, 1712.7 (C=O); 1492.8, 1332.7 (NO2) |
| 5 | N5 | B1 | C1 | 1 | DMF as solvent; Na$_2$CO$_3$ as base | 22 | B | 0.23 | | 3442.7, 3364.5 (NH, NH$_2$); 1683.8 (C=O) |
| 10 | N10 | B1 | C1 | 1 | DMF as solvent; NEt$_3$ as base | 3 | B | 0.5 | ESI: (M + H)$^+$ = 549/551/553 (Br$_2$) | 1666.4 (C=O) |
| 11 | N11 | B1 | C1 | 1 | acetone/MeCO$^t$Bu as solvent; Na$_2$CO$_3$ as base | 30 | B | 0.24 | | 1668.3 (C=O) |
| 113 | N42 | B1 | C1 | 1 | DMF as solvent; NEt$_3$ as base | 18 | A | 0.25 | ESI: (M + H)$^+$ = 607/609/611 (Br$_2$) | 1703.0 (C=O) |

EXAMPLE 2

Preparation of compounds of general formula:

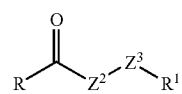

1-{1-[4-(4-amino-3,5-dibromophenyl)-1,4-dioxobutyl]-4-piperidinyl}-1,3-dihydro-4-phenyl-2(2H)-imidazolone (Item no. 12)

A mixture of 1.0 g (2.849 mmol) of 4-amino-3,5-dibromo-γ-oxo-benzenebutanoic acid, 1.04 g (2.91 mmol) of 1,3-dihydro-1-(4-piperidinyl)-4-phenyl-2(2H)-imidazolone, 0.935 g (2.912 mmol) of TBTU, 1.02 ml (5.77 mmol) of DIEA and 50 ml of tetrahydrofuran was stirred for 1 hour at ambient temperature. The reaction mixture was diluted with 300 ml of water and acidified slightly with citric acid. The precipitate formed was suction filtered and washed carefully with water, then with 3 ml of tetrahydrofuran, and finally dried in a circulating air dryer at a temperature of 60° C. 1.3 g (79% of theoretical) of a colourless, crystalline product were obtained, $R_f$ 0.47 (El A). IR (KBr): 1679.9 cm$^{-1}$ (C=O) MS: M$^+$=574/576/578 (Br$_2$)

The following were prepared analogously:

| Item no. | N | B | C | Remarks | % yield | EI | $R_f$ | MS | IR [cm$^{-1}$] | m.p. [° C.] |
|---|---|---|---|---|---|---|---|---|---|---|
| 13 | N13 | B2 | C1 | THF/DMF 1/1 as solvent | 25 | A | 0.47 | ESI: (M + H)$^+$ = 564/566/568 (Br$_2$); (M + Na)$^+$ = 586/588/590 (Br$_2$) | 1670.3 (C=O) | >225 |
| 14 | N14 | B2 | C1 | DMF as solvent; NEt$_3$ as base | 73 | A | 0.48 | M$^+$ = 576/578/580 (Br$_2$) | 1697.3 (C=O) | |
| 15 | N15 | B2 | C1 | DMF as solvent; DIEA as base | 67 | A | 0.48 | M$^+$ = 588/590/592 (Br$_2$) | 1678.0, 1647.1 (C=O) | |
| 16 | N16 | B2 | C1 | DMF as solvent; DIEA as base | 47 | A | 0.58 | | 1656.8 (C=O) | |
| 17 | N16 | B2 | C2 | DMF as solvent; DIEA as base | 19 | A | 0.63 | M$^+$ = 540/542 (Br) | 1670.3 (C=O) | |
| 18 | N10 | B2 | C2 | DMF as solvent; DIEA as base | 69 | A | 0.43 | M$^+$ = 526/528 (Br) | 1701.1, 1687.6, 1664.5 (C=O) | 243 (MeOH) |
| 19 | N1 | B2 | C2 | DMF as solvent; DIEA as base | 61 | A | 0.39 | M$^+$ = 512/514 (Br) | 1685.7 (C=O) | 128 |
| 21 | N12 | B2 | C2 | DMF as solvent; DIEA as base | 78 | B | 0.70 | | | 243 (MeOH) |
| 25 | N10 | B2 | C4 | DMF as solvent; NEt$_3$ as base | 47 | B | 0.79 | M$^+$ = 421 | 1674, 1657 (C=O) | 171–172 (MeOH) |
| 26 | N10 | B2 | C5 | DMF as solvent; NEt$_3$ as base | 68 | A | 0.40 | M$^+$ = 425/427 (Cl) | 1689.5, 1662.5, 1654.8 (C=O) | 237–238 (MeOH) |
| 27 | N10 | B2 | C6 | DMF as solvent; NEt$_3$ as base | 85 | A | 0.25 | M$^+$ = 465 | 1666.4 (C=O) | 258–259 (decomp.) |
| 28 | N10 | B2 | C7 | DMF as solvent; NEt$_3$ as base | 54 | A | 0.33 | M$^+$ = 470/472 (Cl) | 1689.5, 1668.3, 1631.7 (C=O) | 207–209 |
| 29 | N17 | B2 | C1 | THF as solvent; NEt$_3$ as base | 81 | A | 0.30 | M$^+$ = 622/624/626 (Br$_2$) | 1654.8 (C=O) | 256–258 (acetonitrile) |
| 30 | N10 | B2 | C8 | THF as solvent; NEt$_3$ as base | 59 | B | 0.53 | | 1652.9, 1633.6 (C=O) | colourless crystals |
| 31 | N10 | B2 | C9 | THF as solvent; NEt$_3$ as base | 88 | B | 0.71 | M$^+$ = 447 | 1703.0, 1670.3 (C=O) | colourless crystals |
| 32 | N18 | B2 | C1 | THF as solvent; NEt$_3$ as base | 61 | A | 0.38 | M$^+$ = 548/550/552 (Br$_2$) | 1656.8 (C=O) | colourless crystals |
| 33 | N19 | B2 | C1 | THF as solvent; NEt$_3$ as base | 85 | A | 0.48 | M$^+$ = 592/594/596 (Br$_2$) | 1664.5 (C=O) | colourless crystals |
| 34 | N20 | B2 | C1 | THF as solvent; NEt$_3$ as base | 83 | A | 0.50 | ESI: (M + H)$^+$ = 597/599/601 (Br$_2$Cl); (M + Na)$^+$ = 619/621/623/625 (Br$_2$Cl) | 1664.5 (C=O) | colourless crystals |
| 35 | Nb | B2 | C10 | THF as solvent; NEt$_3$ as base | 10 | A | 0.34 | M$^+$ = 440/442 (Cl) | 1668.3, 1647.1 (C=O) | |
| 36 | N21 | B2 | C1 | THF as solvent; NEt$_3$ as base | 85 | A | 0.45 | M$^+$ = 568/570/572 (Br$_2$) | 1652.9 (C=O) | colourless crystals |
| 37 | N22 | B2 | C1 | THF/DMF 5/1 as solvent; DIEA as base | 37 | A | 0.25 | M$^+$ = 642/644/646 (Br$_2$) | 1685.7 (C=O) | colourless crystals |
| 38 | N23 | B2 | C1 | DMF as solvent; DIEA as base | 6 | A | 0.18 | M$^+$ = 580/582/584 (Br$_2$) | 1683.8 (C=O) | |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 39 | N24 | B2 | C1 | DMF as solvent; DIEA as base | 43 | A | 0.48 | M$^+$ = 575/577/579 (Br$_2$) | 1685.7 (C=O) | |
| 40 | N25 | B2 | C1 | DMF as solvent; DIEA as base | 26 | A | 0.52 | | 1658.7 (C=O) | |
| 41 | N26 | B2 | C1 | THF as solvent; NEt$_3$ as base | 15 | A | 0.47 | M$^+$ = 642/644/646 (Br$_2$) | | |
| 42 | N27 | B2 | C1 | DMF as solvent; DIEA as base | 72 | A | 0.57 | M$^+$ = 563/565/567 (Br$_2$) | 1668 (C=O) | >250 |
| 43 | N28 | B2 | C1 | DMF as solvent, DIEA as base | 53 | A | 0.48 | M$^+$ = 563/565/567 (Br$_2$) | 1662 (C=O) | >250 |
| 44 | N29 | B2 | C1 | DMF as solvent; DIEA as base | 72 | A | 0.46 | M$^+$ = 578/580/582 (Br$_2$) | 1651 (C=O) | colourless crystals |
| 45 | N10 | B3 | C11 | THF as solvent; NEt$_3$ as base | 57 | A | 0.70 | M$^+$ = 467/469 (Br) | 1664 (C=O) | colourless crystals |
| 46 | N10 | B3 | C12 | THF as solvent; NEt$_3$ as base | 77 | A | 0.68 | M$^+$ = 417 | 1662 (C=O) | colourless crystals |
| 47 | N10 | B3 | C13 | THF as solvent; NEt$_3$ as base | 80 | A | 0.60 | M$^+$ = 405 | 1655 (C=O) | colourless crystals |
| 48 | N10 | B3 | C14 | THF as solvent; NEt$_3$ as base | 52 | A | 0.63 | M$^+$ = 439 | | colourless crystals |
| 49 | N10 | B3 | C15 | THF as solvent; NEt$_3$ as base | 50 | A | 0.72 | M$^+$ = 445 | | colourless crystals |
| 50 | N10 | B3 | C16 | THF as solvent; NEt$_3$ as base | 53 | A | 0.65 | M$^+$ = 457/459/461 (Cl$_2$) | 1666 (C=O) | colourless crystals |
| 51 | N10 | B3 | C17 | THF as solvent; NEt$_3$ as base | 65 | A | 0.57 | M$^+$ = 434 | 1668 (C=O) | colourless crystals |
| 52 | N10 | B3 | C18 | THF as solvent; NEt$_3$ as base | 34 | A | 0.66 | M$^+$ = 403 | 1660 (C=O) | colourless crystals |
| 53 | N10 | B3 | C19 | THF as solvent; NEt$_3$ as base | 59 | A | 0.73 | M$^+$ = 471 | 1668, 1630 (C=O) | colourless crystals |
| 54 | N10 | B3 | C20 | THF as solvent; NEt$_3$ as base | 46 | A | 0.77 | M$^+$ = 517 | 1657 (C=O) | colourless crystals |
| 55 | N10 | B3 | C21 | THF as solvent; NEt$_3$ as base | 59 | A | 0.70 | ESI: (M + Na)$^+$ = 460/462 (Cl); (2M + Na)$^+$ = 897/899/901 (2 Cl) | 1664, 1639 (C=O) | colourless crystals |
| 56 | N10 | B3 | C22 | THF as solvent; NEt$_3$ as base | 8 | A | 0.72 | M$^+$ = 512/514 (Br) | 1664 (C=O) | |
| 57 | N10 | B3 | C23 | THF as solvent; NEt$_3$ as base | 4 | A | 0.68 | | | |
| 59 | N30 | B2 | C1 | THF/DMF 3/1 as solvent; NEt$_3$ as base | 93 | A | 0.59 | ESI: (M + H)$^+$ = 561/563/565 (Br$_2$); (M + Na)$^+$ = 583/585/587 (Br$_2$) | | 272–274 (decomp.) |
| 60 | N10 | B5 | C1 | THF as solvent; DIEA as base | 46 | A | 0.53 | ESI: (M + H)$^+$ = 549/551/553 (Br$_2$); (M + Na)$^+$ = 571/573/575 (Br$_2$) | 1668.3 (C=O) | |
| 61 | N31 | B2 | C1 | THF as solvent; NEt$_3$ as base | 94 | A | 0.88 | M$^+$ = 561/563/565 (Br$_2$) | 1668.3, 1652.9 (C=O) | 246–252 |
| 62 | N10 | B2 | C24 | THF/DMF 1/1 as solvent; NEt$_3$ as base | 58 | A | 0.46 | M$^+$ = 467 | 1678.0, 1658.7 (C=O) | decomp. from about 200 |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 63 | N32 | B2 | C1 | THF as solvent; DIEA as base | 42 | A | 0.20 | | 1670.3, 1645.2 (C=O) | 207 (decomp.) |
| 64 | N12 | B5 | C1 | THF as solvent; DIEA as base | 31 | A | 0.24 | M$^+$ = 560/562/564 (Br$_2$) | 1679.9 (C=O) | 162.5–163.5 (diisopropyl-ether) |
| 65 | N10 | B2 | C25 | THF/DMF 1/1 as solvent; DIEA as base | 65 | A | 0.54 | M$^+$ = 547/549/551 (Br$_2$) | 1666.4 (C=O) | 212–214 (EtOH/ active charcoal) |
| 66 | N10 | B2 | C26 | THF as solvent; DIEA as base | 52 | A | 0.39 | M$^+$ = 421 | 1668.3 (C=O) | 174–175 (AcOEt) |
| 67 | N10 | B2 | C27 | THF as solvent; DIEA as base | 18 | A | 0.38 | M$^+$ = 409 | 1668.3 (C=O) | 164–166 (diisopropyl-ether) |
| 68 | N1 | B5 | C1 | THF as solvent; DIEA as base | 46 | A | 0.60 | M$^+$ = 534/536/538 (Br$_2$) | 1703.0 (C=O) | 172–173 (diisopropyl-ether) |
| 69 | N33 | B2 | C1 | THF as solvent; DIEA as base | 65 | A | 0.76 | M$^+$ = 562/564/566 (Br$_2$) | 1691.5 (C=O) | 225–226 (94% EtOH) |
| 70 | N10 | B5 | C2 | THF as solvent; DIEA as base | 39 | A | 0.23 | M$^+$ = 512/514 (Br) | 1666.4 (C=O) | 94–98 (diisopropyl-ether) |
| 71 | N10 | B5 | C3 | THF as solvent; DIEA as base | 76 | A | 0.48 | M$^+$ = 470/472 (Br) | 1668.3 (C=O) | 181–183 (diisopropyl-ether) |
| 72 | N10 | B3 | C28 | THF as solvent; DIEA as base | 26 | A | 0.55 | | 2229.6 (CN); 1668.3 (C=O) | 191–193 (EtOH) |
| 74 | N10 | B6 | C29 | THF as solvent; DIEA as base | 40 | A | 0.48 | ESI: (M + H)$^+$ = 466; (M + Na)$^+$ = 488 | 2221.9 (CN); 1635.5 (CON) | 148–151 |
| 75 | N10 | B3 | C29 | by-product of synthesis of Item no. (74) | 4 | A | 0.60 | ESI: (M + H)$^+$ = 448; (M + Na)$^+$ = 470 | 1666.4 (C=O) | colourless crystals |
| 76 | N10 | B2 | C29 | THF as solvent; DIEA as base | 49 | A | 0.44 | M$^+$ = 449 | 2221.9 (CN), 1664.5 (C=O); 1637.5 (CON) | |
| 78 | N1 | B2 | C29 | THF as solvent; DIEA as base | 47 | A | 0.14 | M$^+$ = 461 | 1658.7 (C=O) | |
| 79 | N34 | B2 | C1 | THF as solvent; NEt$_3$ as base | 87 | A | 0.87 | ESI: (M + H)$^+$ = 613/615/617 (Br$_2$); (M + Na)$^+$ = 635/637/639 (Br$_2$) | 1706.9 (C=O) | colourless crystals |
| 81 | N35 | B2 | C1 | by-product of synthesis of Item no. (80) | 15 | A | 0.37 | ESI: (M + H)$^+$ = 433/435/437 (Br$_2$); (M + Na)$^+$ = 455/457/459 (Br$_2$); (M − H)$^-$ = 431/433/435 (Br$_2$) | 1651 (amide-C=O) | |
| 83 | N10 | B3 | C1 | THF as solvent; DIEA as base | 9 | A | 0.50 | ESI: (M + H)$^+$ = 561/563/565 (Br$_2$); (M + Na)$^+$ = 583/585/587 (Br$_2$); (2M + Na)$^+$ = 1144/1146/ 1148/1150 (Br$_4$); (M + NH$_4$)$^+$ = 578/580/582 (Br$_2$) | 1662.5 (C=O) | |
| 84 | N12 | B3 | C1 | THF as solvent; DIEA as base | 9 | A | 0.22 | M$^+$ = 572/574/576 (Br$_2$) | 1683.8 (C=O) | |
| 85 | N36 | B3 | C1 | THF as solvent; DIEA as base | 17 | A | 0.72 | M$^+$ = 346/348/350 (Br$_2$) | 1674.1 (C=O) | |
| 86 | N30 | B2 | C1 | THF as solvent; NEt$_3$ as base | 12 | A | 0.42 | (M + Na)$^+$ = 582/584/586 (Br$_2$) | 1651.0 (C=O) | colourless crystals |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 87 | N37 | B2 | C1 | THF as solvent; NEt$_3$ as base | 18 | A | 0.64 | M$^+$ = 561/563/565 (Br$_2$) | 1676.0 (C=O) | colourless crystals |
| 100 | N76 | B2 | C1 | THF/DMF 5/1 as solvent; NEt$_3$ as base | 40 | A | 0.33 | M$^+$ = 534/536/538 (Br$_2$) | 1669 (C=O) | colourless crystals |
| 101 | N41 | B2 | C1 | THF as solvent; NEt$_3$ as base | 38 | A | 0.22 | M$^+$ = 745/747/749/ 751/753 (Br$_4$) | 1680 (C=O) | colourless crystals |
| 102 | N10 | B2 | C32 | THF/DMF 5/1 as solvent; NEt$_3$ as base | 77 | A | 0.25 | M$^+$ = 439 | 1666 (C=O) | 169–170 (MeOH) |
| 103 | N10 | B2 | C33 | THF/DMF 4/1 as solvent; NEt$_3$ as base | 42 | A | 0.50 | M$^+$ = 561/563/565 (Br$_2$) | 1662 (C=O) | colourless crystals |
| 104 | N10 | B3 | C34 | THF/DMF 5/1 as solvent; DIEA as base | 38 | A | 0.48 | M$^+$ = 466/468 (Cl) | 1666, 1657 (C=O) | |
| 115 | N1 | B2 | C1 | THF/DMF 5/1 as solvent; NEt$_3$ as base | 87 | A | 0.48 | ESI: (M + H)$^+$ = 549/551/553 (Br$_2$); (M + Na)$^+$ = 571/573/575 (Br$_2$) | 3450.4, 3325.1 (NH, NH$_2$); 1662.5 (C=O) | |
| 116 | N10 | B2 | C1 | THF/DMF 5/1 as solvent; NEt$_3$ as base | 77 | A | 0.52 | ESI: (M + H)$^+$ = 563/565/567 (Br$_2$); (M + Na)$^+$ = 585/587/589 (Br$_2$) | 3448.5, 3325.1, 3207.4 (NH, NH$_2$); 1662.5 (C=O) | |
| 117 | N44 | B2 | C1 | THF/DMF 1/1 as solvent; NEt$_3$ as base | 27 | A | 0.10 | ESI: (M + H)$^+$ = 567/569/571 (Br$_2$); (M + Na)$^+$ = 589/591/593 (Br$_2$); (M − H)$^-$ = 567/569/571 (Br$_2$) | 1679.9 (C=O) | |
| 118 | N45 | B2 | C1 | THF/DMF 5/1 as solvent; NEt$_3$ as base | 73 | A | 0.58 | M$^+$ = 620/622/624 (Br$_2$) | 1722.3, 1670.3 (C=O) | |
| 120 | N47 | B2 | C1 | DMF as solvent; DIEA as base | 75 | A | 0.32 | ESI: (M + H)$^+$ = 566/568/570 (Br$_2$); (M + Na)$^+$ = 588/590/592 (Br$_2$) | 3471.7, 3367.5 (NH, NH$_2$); 1664.5, 1631.7 (C=O) | |
| 125 | N52 | B2 | C1 | THF as solvent; DIEA as base | 36 | A | 0.87 | M$^+$ = 600/602/604 (Br$_2$) | 1652.9 (C=O) | |
| 127 | N1 | B12 | C1 | THF as solvent; DIEA as base | 71 | A | 0.32 | M$^+$ = 563/565/567 (Br$_2$) | 1701, 1674, 1624 (C=O) | |
| 128 | N10 | B12 | C1 | THF as solvent; DIEA as base | 81 | A | 0.25 | M$^+$ = 577/579/581 (Br$_2$) | 1653, 1635 (C=O) | |
| 129 | N1 | B13 | C1 | THF as solvent; DIEA as base | 29 | A | 0.48 | M$^+$ = 549/551/553 (Br$_2$) | 1697, 1632 (C=O) | |
| 130 | N10 | B13 | C1 | THF as solvent; DIEA as base | 27 | A | 0.48 | | 1655 (C=O) | |
| 131 | N12 | B13 | C1 | THF as solvent; DIEA as base | 26 | A | 0.20 | M$^+$ = 575/577/579 (Br$_2$) | 1674 (C=O) | |
| 132 | N53 | B2 | C1 | THF as solvent; DIEA as base | 20 | A | 0.66 | ESI: (M + H)$^+$ = 680/682/684 (Br$_2$); (M + Na)$^+$ = 702/704/706 (Br$_2$) | 1689.5 (C=O) | |
| 133 | N10 | B2 | C41 | THF/DMF 5/1 as solvent; NEt$_3$ as base | 65 | A | 0.25 | M$^+$ = 604/606/608 (Br$_2$) | 1697.3, 1639.4 (C=O) | |
| 136 | N12 | B12 | C1 | THF as solvent; DIEA as base | 10 | A | 0.10 | M$^+$ = 589/591/593 (Br$_2$) | 1678 (C=O) | |
| 137 | N1 | B14 | C1 | THF as solvent; DIEA as base | 88 | A | 0.25 | M$^+$ = 563/565/567 (Br$_2$) | 1703 (C=O) | |
| 138 | N10 | B14 | C1 | THF as solvent; DIEA as base | 69 | A | 0.20 | M$^+$ = 577/579/581 (Br$_2$) | 1662 (C=O) | |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 139 | N56 | B2 | C1 | THF as solvent; DIEA as base | 33 | A | 0.08 | M$^+$ = 568/570/572 (Br$_2$) | 3456.2 (NH, NH$_2$); 1671.1, 1651.0 (C=O) | |
| 143 | N1 | B2 | C42 | THF as solvent; DIEA as base | 86 | A | 0.44 | M$^+$ = 427 | 1689.5 (C=O) | |
| 144 | N10 | B2 | C42 | THF as solvent; DIEA as base | 84 | A | 0.47 | M$^+$ = 441 | 1668.3 (C=O) | |
| 145 | N1 | B2 | C14 | THF as solvent; DIEA as base | 81 | A | 0.45 | M$^+$ = 427 | 1695.3, 1641.3 (C=O) | |
| 146 | N10 | B2 | C14 | THF as solvent; DIEA as base | 52 | A | 0.52 | M$^+$ = 441 | 1666.4 (C=O) | |
| 147 | N10 | B15 | C1 | THF as solvent; DIEA as base | 73 | A | 0.63 | M$^+$ = 576/578/580 (Br$_2$) | 3485.2 (NH, NH$_2$); 1670.3 (C=O) | |
| 149 | N58 | B2 | C1 | THF/DMF 5/1 as solvent; NEt$_3$ as base | 57 | A | 0.72 | M$^+$ = 588/590/592 (Br$_2$) | 1670.3 (C=O) | |
| 150 | N59 | B2 | C1 | THF/DMF 5/1 as solvent; NEt$_3$ as base | 53 | B | 0.20 | (M + H)$^+$ = 618/620/622 (Br$_2$) | 1674.1 (C=O) | |
| 151 | N60 | B2 | C1 | by-product of synthesis of Item no. (150) | 12 | A | 0.11 | M$^+$ = 617/619/621 (Br$_2$) | 1672.2 (C=O) | |
| 152 | N61 | B2 | C1 | THF as solvent; DIEA as base | 62 | A | 0.70 | M$^+$ = 604/606/606 (Br$_2$) | 1705 (C=O) | |
| 153 | N62 | B2 | C1 | THF/DMF 5/1 as solvent; NEt$_3$ as base | 63 | A | 0.76 | M$^+$ = 590/592/594 (Br$_2$) | 1712.7, 1674.1 (C=O) | |
| 154 | N63 | B2 | C1 | THF/DMF 5/1 as solvent; NEt$_3$ as base | 70 | A | 0.89 | M$^+$ = 598/600/602 (Br$_2$) | 1672.2 (C=O) | |
| 155 | N64 | B2 | C1 | THF as solvent; NEt$_3$ as base | 71 | A | 0.21 | M$^+$ = 592/594/592 (Br$_2$) | 1680, 1647 (C=O) | |
| 157 | N65 | B2 | C1 | THF as solvent; DIEA as base | 90 | A | 0.30 | M$^+$ = 624/626/628 (Br$_2$) | 1683.8 (C=O) | |
| 158 | N66 | B2 | C1 | THF/DMF 5/1 as solvent; NEt$_3$ as base | 64 | | | M$^+$ = 650/652/654 (Br$_2$) | 1674.1 (C=O) | |
| 159 | N67 | B2 | C1 | THF as solvent; DIEA as base | 77 | A | 0.20 | ESI: (M + H)$^+$ = 605/607/609 (Br$_2$); (M + Na)$^+$ = 627/629/631 (Br$_2$) | 1682 (C=O) | |
| 160 | N68 | B2 | C1 | THF/DMF 5/1 as solvent; NEt$_3$ as base | 80 | A | 0.30 | | 1684 (C=O) | |
| 161 | N69 | B2 | C1 | THF as solvent; DIEA as base | 98 | A | 0.55 | M$^+$ = 596/598/600 (Br$_2$Cl) | 1670 (C=O) | |
| 164 | N70 | B2 | C1 | THF/DMF 5/1 as solvent; NEt$_3$ as base | 20 | A | 0.35 | M$^+$ = 599/601/603 (Br$_2$) | 1695, 1678 (C=O) | |
| 165 | N10 | B2 | C45 | THF as solvent; DIEA as base | 71 | A | 0.64 | M$^+$ = 499 | 1658 (C=O) | |
| 168 | N10 | B3 | C24 | THF as solvent; NEt$_3$ as base | 37 | A | 0.68 | M$^+$ = 465 | 1658 (C=O) | |
| 169 | N10 | B3 | C46 | THF as solvent; DIEA as base | 61 | A | 0.65 | M$^+$ = 461 | 3473 (NH, NH$_2$); 1705, (C=O) | |
| 170 | N10 | B3 | C47 | THF as solvent; DIEA as base | 52 | A | 0.43 | M$^+$ = 479 | 1668 (C=O) | |
| 171 | N10 | B3 | C48 | THF as solvent; DIEA as base | 60 | A | 0.62 | M$^+$ = 473 | 1658 (C=O) | |
| 172 | N10 | B3 | C49 | THF/DMF 5/1 as solvent; DIEA as base | 32 | A | 0.65 | M$^+$ = 417 | 1660 (C=O) | |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 173 | N10 | B3 | C50 | THF as solvent; NEt$_3$ as base | 33 | A | 0.58 | M$^+$ = 419 | 1658 (C=O) | |
| 174 | N10 | B3 | C51 | THF as solvent; NEt$_3$ as base | 38 | A | 0.59 | M$^+$ = 447 | 1671, 1658 (C=O) | |
| 175 | N10 | B3 | C52 | THF/DMF 5/1 as solvent; NEt$_3$ as base | 64 | A | 0.43 | M$^+$ = 437 | 1664 (C=O) | |
| 176 | N10 | B3 | C53 | THF as solvent; DIEA as base | 23 | A | 0.54 | M$^+$ = 472 | 1666 (C=O) | |
| 177 | N10 | B3 | C54 | THF as solvent; NEt$_3$ as base | 14 | A | 0.61 | M$^+$ = 433 | 1658 (C=O) | |
| 178 | N10 | B3 | C55 | THF/DMF 5/1 as solvent; NEt$_3$ as base | 10 | A | 0.71 | M$^+$ = 457 | | |
| 180 | N10 | B17 | C1 | THF as solvent; DIEA as base | 55 | A | 0.50 | M$^+$ = 576/578/580 (Br$_2$) | 3471, 3352 (NH, NH$_2$); 1664 (C=O) | |
| 181 | N71 | B2 | C1 | THF/DMF 5/1 as solvent; NEt$_3$ as base | 60 | A | 0.94 | ESI: (M + H)$^+$ = 662/664/666 (Br$_2$) | 1674, 1637 (C=O) | |
| 185 | N10 | B18 | C1 | THF/DMF 5/1 as solvent; NEt$_3$ as base | 48 | A | 0.66 | M$^+$ = 576/578/580 (Br$_2$) | 1662 (C=O) | |
| 186 | N74 | B2 | C1 | THF as solvent; DIEA as base | 90 | A | 0.51 | ESI: (M − H)$^-$ = 606/608/610 (Br$_2$) | 1660 (C=O) | |
| 187 | N75 | B2 | C1 | THF as solvent; DIEA as base | 95 | A | 0.60 | ESI: (M − H)$^-$ = 575/577/579 (Br$_2$); (M + Na)$^+$ = 599/601/603 (Br$_2$); M$^+$ = 576/578/580 (Br$_2$) | 1658 (C=O) | |
| 188 | N91 | B2 | C1 | THF as solvent; DIEA as base | 19 | | | ESI: (M + Na)$^+$ = 737/739/741 (Br$_2$) | 1681.8, 1645.2 (C=O) | |
| 189 | N92 | B2 | C1 | THF as solvent; DIEA as base | 45 | | | ESI: (M + H)$^+$ = 831/833/835 (Br$_2$) | 3458.2, 3381.0, 3338.6 (NH, NH$_2$); 1652.9 (C=O) | |

EXAMPLE 3

4-amino-3,5-dibromo-N-{2-[4-(1,3-dihydro-2(2H)-oxo-1-benzimidazolyl)-1-piperidinyl]ethyl}-benzamide (Item no. 58)

A mixture of 0.279 g (1.0 mmol) of 4-amino-3,5-dibromobenzoic acid, 0.489 g (1.0 mmol) of 1-[1-(2-aminoethyl)-4-piperidinyl)]-1,3-dihydro-2(2H)-benzimidazolone, 0.321 g (1.0 mmol) of TBTU, 2 ml of triethylamine and 50 ml DMF was stirred overnight at ambient temperature. The reaction mixture was diluted with 300 ml of water. The precipitate formed was purified by column chromatography (MN-silica gel 60, Macherey-Nagel, 70–230 mesh ASTM, eluant: ethyl acetate/methanol 95/5/(v/v/)). After the appropriate eluates had been worked up, 200 mg. (37% of theoretical) of a colourless crystalline product were obtained, m.p. 228–229° C. and $R_f$ 0.12 (El A).

IR (KBr): 3468, 3364, 3318 (NH, NH$_2$); 1697 cm$^{-1}$ (C=O).

The following were prepared analogously:

| Item no. | N | B | C | Remarks | % yield | EI | $R_f$ | MS | IR [cm$^{-1}$] | m.p. [° C.] |
|---|---|---|---|---|---|---|---|---|---|---|
| 80 | N77 | B2 | C1 | THF as solvent; DIEA as base | 23 | B | 0.23 | ESI: (M + H)$^+$ = 646/648/650 (Br$_2$); (M + Na)$^+$ = 668/670/672 (Br$_2$) | 1668.3 (C=O) | |
| 82 | N77 | B7 | C1 | THF as solvent; DIEA as base | 25 | B | 0.37 | M$^+$ = 589/591/593 (Br$_2$) | 1670.3 (C=O) | |

-continued

| Item no. | N | B | C | Remarks | % yield | EI | $R_f$ | MS | IR [cm$^{-1}$] | m.p. [° C.] |
|---|---|---|---|---|---|---|---|---|---|---|
| 88 | N88 | B7 | C1 | THF/DMF 5/1 as solvent; DIEA as base | 47 | A | 0.17 | M$^+$ = 589/591/593 (Br$_2$) | 1664.5, 1645.2 (C=O) | |
| 89 | N88 | B7 | C31 | THF/DMF 5/1 as solvent; DIEA as base | 23 | A | 0.13 | ESI: (M − H)$^-$ = 589/591/593 (Br$_2$) | 1652.9 (C=O) | colourless crystals |
| 90 | N80 | B7 | C1 | by-product of synthesis of Item no. 82 | 10 | B | 0.46 | M$^+$ = 603/605/607 (Br$_2$) | 1710.6, 1660.4 (C=O) | |
| 91 | N81 | B7 | C1 | THF as solvent; DIEA as base | 8 | B | 0.37 | ESI: (M + H)$^+$ = 602/604/606 (Br$_2$); (M + Na)$^+$ = 624/626/628 (Br$_2$) | 1678 (C=O) | |
| 92 | N77 | B7 | C31 | by-product of synthesis of Item no. 93 | 5 | B | 0.28 | ESI: (M + H)$^+$ = 591/593/595 (Br$_2$); (M + Na)$^+$ = 613/615/617 (Br$_2$) | 1672 (C=O) | |
| 93 | N80 | B7 | C31 | THF/DMF 5/1 as solvent; DIEA as base | 2 | B | 0.37 | ESI: (M + H)$^+$ = 605/607/609 (Br$_2$); (M − H)$^-$ = 603/605/607 (Br$_2$) | | |
| 94 | N81 | B7 | C31 | THF as solvent; DIEA as base | 12 | B | 0.29 | M$^+$ = 602/604/606 (Br$_2$); ESI: (M + H)$^+$= 603/605/607 (Br$_2$); (M − H)$^-$ = 601/603/605 (Br$_2$) | 1682 (C=O) | |
| 95 | N82 | B7 | C1 | DMF as solvent; DIEA as base | 15 | B | 0.44 | M$^+$ = 669/671/673 (Br$_2$) | 3483, 3386 (NH, NH$_2$); 1689 (C=O) | |
| 96 | N83 | B7 | C1 | by-product of synthesis of Item no. 95 | 8 | A | 0.19 | M$^+$ = 685/687/689 (Br$_2$) | 1714 (C=O) | |
| 97 | N84 | B7 | C1 | by-product of synthesis of Item no. 95 | 3 | A | 0.14 | ESI: (M + H)$^+$ = 674/676/678 (Br$_2$); (M + Na)$^+$ = 696/698/700 (Br$_2$) | 3481, 3375 (NH, NH$_2$); 1693 (C=O) | |
| 98 | N82 | B7 | C31 | DMF as solvent; DIEA as base | 15 | B | 0.34 | ESI: (M + H)$^+$ = 671/673/675 (Br$_2$); (M − H)$^-$ = 669/671/673 (Br$_2$) | 1684 (C=O) | |
| 99 | N79 | B7 | C1 | THF as solvent; DIEA as base | 44 | A | 0.28 | M$^+$ = 561/563/565 (Br$_2$) | 1639 (C=O) | 149–151 (decomp.) (AcOEt) |
| 142 | N87 | B7 | C43 | THF as solvent; DIEA as base | 37 | A | 0.12 | M$^+$ = 482/484 (Cl) | 1689, 1634 (C=O) | |
| 156 | N89 | B7 | C44 | THF/DMF 1/1 as solvent; NEt$_3$ as base | 58 | A | 0.43 | ESI: (M + H)$^+$ = 552; (M + Na)$^+$ = 574 | 3332.8 (NH, NH$_2$); 1660.8 (C=O) | |
| 162 | N85 | B7 | C1 | THF as solvent; DIEA as base | 32 | A | 0.12 | M$^+$ = 631/633/635 (Br$_2$) | 3440 (NH, NH$_2$); 1707 (C=O) | colourless crystals |
| 163 | N86 | B7 | C1 | THF/DMF 3/1 as solvent; DIEA as base | 25 | B | 0.44 | M$^+$ = 651/653/655 (Br$_2$) | 3464, 3373 (NH, NH$_2$); 1685 (C=O) | |
| 166 | N78 | B7 | C1 | THF as solvent; DIEA as base | 32 | A | 0.19 | M$^+$ = 575/577/579 (Br$_2$) | 3411, 3319 (NH, NH$_2$); 1657 (C=O) | |
| 167 | N78 | B7 | C16 | THF as solvent; DIEA as base | 58 | A | 0.13 | M$^+$ = 472/474/476 (Cl$_2$) | 1664 (C=O) | |

EXAMPLE 4

Preparation of compounds of general formula:

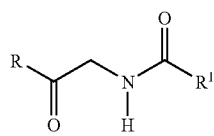

N-{2-[4-(3,4-dihydro-2(1H)-oxoquinazolin-3-yl)-1-piperidinyl]-2-oxoethyl}-2-naphthalenecarboxamide (Item no. 140)

A mixture of 0.5 g (1.243 mmol) of 3-[1-(2-amino-1-oxoethyl)-4-piperidinyl)]-3,4-dihydro-2(1H)-quinazolinone-trifluoroacetate, 0.33 g (1.731 mmol) of 2-naphthoyl chloride, 0.5 ml of triethylamine and 100 ml acetonitrile was stirred overnight at ambient temperature. The colourless crystals precipitated were suction filtered, thoroughly washed with water and dried in vacuo. Yield: 0.47 g (85% of theoretical). $R_f$ 0.34 (El A). IR (KBr): 3386.8 (NH, NH$_2$); 1670.3, 1633.6 (C=O) MS: M$^+$442

The following was prepared analogously:

| Item no. | N | B | C | remarks | % yield | EI | $R_f$ | MS | IR [cm$^{-1}$] |
|---|---|---|---|---|---|---|---|---|---|
| 141 | N89 | B7 | C14 | acetonitrile as solvent; NEt$_3$ as base | 46 | A | 0.34 | M$^+$ = 442 | 1654.8 (C=O) |

EXAMPLE 5

(E)-3,4-dihydro-3-{1-[1,4-dioxo-4-(4-carboxyphenyl)-2-buten-1-yl]-4-piperidinyl}-2(1H)-quinazolinone (Item no. 179)

A solution of 0.24 g (10.0 mmol) of lithium hydroxide in 20 ml of water was added to a solution of 1.2 g (2.6 mmol) of (E)-3,4-dihydro-3-{1-[1,4-dioxo-4-(4-ethoxycarbonylphenyl)-2-buten-1-yl]-4-piperidinyl}-2(1H)-quinazolinone (Item no. 169) in 20 ml of THF. After stirring for 4 hours at ambient temperature the mixture was diluted with 200 ml of water and extracted once with 100 ml of tert.butylmethylether. The aqueous phase was acidified with 1N hydrochloric acid and extracted five times with a mixture of dichloromethane and methanol (9/1 v/v). The combined organic extracts were dried over sodium sulphate and concentrated by evaporation in vacuo. The residue remaining was triturated with diethylether and suction filtered. After drying in a circulating air dryer 0.5 g (44% of theoretical) of colourless crystals were obtained. $R_f$ 0.72 (EE/MeOH/AcOH 80/20/5 v/v/v) or 0.43 (El D). IR (KBr): 1689 (C=O) MS: no M$^+$ The following were prepared analogously:

| Item no. | N | B | C | remarks | % yield | EI | $R_f$ | MS | IR [cm$^{-1}$] |
|---|---|---|---|---|---|---|---|---|---|
| 114 | N43 | B1 | C1 | saponification of the methyl ester Item no. 113 with LiOH/NaOH 1/20 in water/MeOH 1/1 (v/v) | 58 | D | 0.13 | ESI: (M + H)$^+$ = 593/595/597 (Br$_2$); (M + Na)$^+$ = 615/617/619 (Br$_2$) | 1693.4 (C=O) |
| 119 | N46 | B2 | C1 | saponification of the methyl ester Item no. 118 with NaOH in water/MeOH 3/1 (v/v) | 76 | A | 0.08 | M$^+$ = 606/608/610 (Br$_2$) | 3417.7, 3328.9 (NH, NH$_2$); 1664.5, 1649.0 (C=O) |

EXAMPLE 6

Preparation of compounds of general formula:

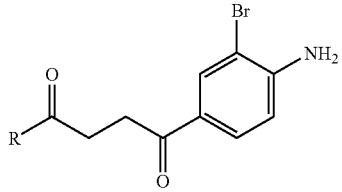

3-{1-[4-(4-amino-3-bromophenyl)-1,4-dioxobutyl]-4-piperidinyl}-3,4-dihydro-2(1H)-quinazolinone (Item no. 22)

A mixture of 1.5 g (2.84 mmol) of 3-{1-[4-(4-acetylamino-3-bromophenyl)-1,4-dioxobutyl]-4-piperidinyl}-3,4-dihydro-2(1H)-quinazolinone and 150 ml of conc. hydrochloric acid was refluxed for 1 hour. The residue was digested with water, the solid precipitated was suction filtered, recrystallised from acetonitrile and dried in vacuo. Yield: 0.88 g (64% of theoretical). $R_f$ 0.34 (El A). IR (KBr): 3471.7, 3342.4 (NH, $NH_2$); 1666.4 (C=O) MS: $M^+$484/486 (Br)

The following were prepared analogously:

| Item no. | N | B | C | Ex. no. | Remarks | % yield | EI | $R_f$ | MS | IR [cm$^{-1}$] | m.p. [° C.] |
|---|---|---|---|---|---|---|---|---|---|---|---|
| 20 | N1 | B2 | C3 | 6 | prepared from Item no. (19) | 62 | A | 0.34 | ESI: $(M + H)^+$ = 471/473 (Br); $(M + Na)^+$ = 493/495 (Br) | | |
| 23 | N16 | B2 | C3 | 6 | prepared from Item no. (17) | 81 | A | 0.35 | $M^+$ = 498/500 (Br) | 1663 (C=O) | |
| 24 | N12 | B2 | C3 | 6 | prepared from Item no. (21) | 60 | B | 0.77 | $M^+$ = 496/498 (Br) | 1679.9 (C=O) | 267 (MeOH) |

EXAMPLE 7

1-[4-(4-amino-3,5-dibromophenyl)-1,4-dioxobutyl]-N-[(2-amino-carbonylaminophenyl)methyl]-4-piperidineamine (Item no. 134)

2 ml of trifluoroacetic acid were added to a mixture of 0.20 g (0.2935 mmol) of 1-[4-(4-amino-3,5-dibromophenyl)-1,4-dioxobutyl]-N-dimethylethoxycarbonyl-N-[(2-aminocarbonylaminophenyl)methyl]-4-piperidineamine (Item no. 132) in 20 ml of methylene chloride. The reaction mixture was stirred for 2 hours at ambient temperature and then evaporated down in vacuo. The residue remaining was triturated with ether and the beige-coloured amorphous solid obtained (0.15 g; 74% of theoretical) was suction filtered. IR (KBr): 1678.0 (C=O) cm$^{-1}$ $R_f$ 0.20 (El B) ESI-MS: $(M+H)^+$=580/582/584 ($Br_2$)

The following were prepared analogously:

| Item no. | N | B | C | remarks | % yield | EI | $R_f$ | MS | IR [cm$^{-1}$] |
|---|---|---|---|---|---|---|---|---|---|
| 135 | N55 | B2 | C1 | prepared from Item no. (188) | 55 | A | 0.32 | ESI: $(M + H)^+$ = 615/617/619 ($Br_2$) | 1674.1 (C=O) |
| 148 | N57 | B2 | C1 | prepared from Item no. (189) | 66 | D | 0.76 | ESI: $(M + H)^+$ = 731/733/735 ($Br_2$); $(M + 2H)^{++}$ = 366/367/368 ($Br_2$) | 1676.0 (C=O) |
| 182 | N72 | B2 | C1 | prepared from Item no. (181) | 100 | D | 0.33 | $M^+$ = 561/563/565 ($Br_2$) | 3448 (NH, $NH_2$); 1674, 1646 (C=O) |

EXAMPLE 8

Preparation of compounds of general formula:

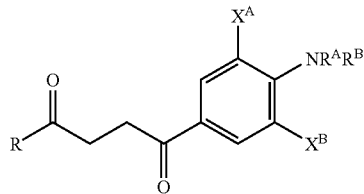

3-{1-[4-[3-chloro-4-[4-(3-dimethylaminopropyl)-1-piperazinyl]-phenyl]-1,4-dioxobutyl]-4-piperidinyl}-3,4-dihydro-2(1H)-quinazolinone (Item no. 106)

A mixture of 921 mg (2.00 mmol) of 3-{1-[4-(3,4-dichloro-phenyl)-1,4-dioxobutyl]-4-piperidinyl}-3,4-dihydro-2(1H)-quinazolinone, 377 mg (2.2 mmol) of 1-(3-dimethylaminopropyl)-piperazine, 10 ml of DMSO and 0.276 g (2.00 mmol) of potassium carbonate was stirred for 24 hours at a reaction temperature of 85° C. The mixture was diluted with 200 ml of water, then extracted exhaustively with EE. The combined extracts were dried over sodium sulphate and concentrated by evaporation in vacuo. The residue remaining was purified twice by column chromatography on silica gel (Amicon, 35–70 μm) (dichloromethane/methanol/conc. ammonia 70/30/1 v/v/v as eluant). The appropriate eluates were combined and after working up in the usual way yielded 30.0 mg (2.5% of theoretical) of the desired substance as a colourless, amorphous substance. $R_f$ 0.68 (El D) or 0.35 (eluant: dichloromethane/methanol/conc. ammonia 50/50/1 v/v/v). MS: $M^+$ 594/596 (Cl); ESI: $(M+H)^+$=595/597 (Cl)

The following were prepared analogously:

| Item no. | N | B | C | remarks | % yield | EI | $R_f$ | MS | IR [cm$^{-1}$] |
|---|---|---|---|---|---|---|---|---|---|
| 107 | N10 | B2 | C36 | exchange of F in the p position for acyl | 13 | C | 0.26 | ESI: $(M + H)^+$ = 636/638 (Br) | 1668 (C=O) |
| 108 | N10 | B2 | C37 | exchange of F in the p position for acyl | 15 | D | 0.72 | ESI: $(M + H)^+$ = 651/653 (Br) | 1668 (C=O) |
| 109 | N10 | B2 | C38 | exchange of F in the p position for acyl | 27 | D | 0.65 | ESI: $(M + H)^+$ = 639/641 (Br) | 1668 (C=O) |
| 111 | N10 | B2 | C39 | exchange of F in the p position for acyl | 1.4 | C | 0.18 | $M^+$ = 728/730/732 (Br$_2$); ESI: $(M + H)^+$ = 729/731/733 (Br$_2$) | |
| 112 | N10 | B2 | C40 | exchange of F in the p position for acyl | 3.0 | D | 0.78 | ESI: $(M + H)^+$ = 800/802/804 (Br$_2$) | |

EXAMPLE 9

Preparation of compounds of general formula:

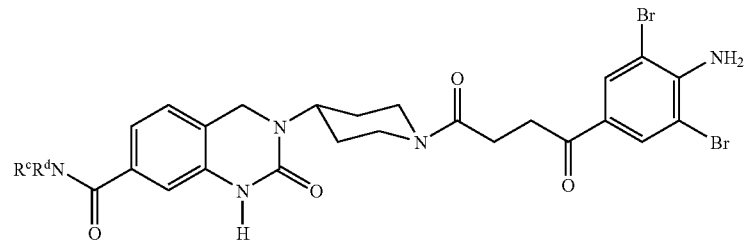

3-{1-[4-(4-amino-3,5-dibromophenyl)-1,4-dioxobutyl]-4-piperidinyl}-3,4-dihydro-2(1H)-oxoquinazolin-7-carboxamide (Item no. 121)

Prepared analogously to Example 2 from 3-{1-[4-(4-amino-3,5-dibromophenyl)-1,4-dioxobutyl]-4-piperidinyl}-3,4-dihydro-2(1H)-oxoquinazoline-7-carboxylic acid (Item no. 119), ammonium carbonate and TBTU in the presence of THF/DMF (5/1 v/v) and triethylamine in a quantitative yield. IR (KBr): 3415.7 (NH, NH$_2$); 1652.9 (C=O) MS: M$^+$605/607/609 (Br$_2$)

The following were prepared analogously:

| Item no. | N | B | C | remarks | % yield | EI | R$_f$ | MS | IR [cm$^{-1}$] |
|---|---|---|---|---|---|---|---|---|---|
| 122 | N49 | B2 | C1 | THF/DMF 5/1 as solvent; NEt$_3$ as base | 88 | D | 53 | M$^+$ = 688/690/692 (Br$_2$) | 1633.6 (C=O) |
| 123 | N50 | B2 | C1 | THF/DMF 5/1 as solvent; NEt$_3$ as base | 85 | A | 0.15 | M$^+$ = 675/677/679 (Br$_2$) | 1672.2, 1635.5 (C=O) |
| 124 | N51 | B2 | C1 | THF/DMF 5/1 as solvent; NEt$_3$ as base | 82 | B | 0.50 | M$^+$ = 649/651/653 (Br$_2$) | 1662.5 (C=O) |

EXAMPLE 10

5-acetylamino-1-{1-[4-(4-amino-3,5-dibromophenyl)-4-oxobutyl]-4-piperidinyl}-1,3-dihydro-2(2H)-benzimidazolone (Item no. 6) and 3-acetyl-5-acetylamino-1-{1-[4-(4-amino-3,5-dibromophenyl)-4-oxobutyl]-4-piperidinyl}-1,3-dihydro-2(2H)-benzimidazolone (Item no. 7)

73.5 mg (0.72 mmol) of acetic anhydride were added to a solution of 200 mg (0.363 mmol) of 5-amino-1-{1-[4-(4-amino-3,5-dibromophenyl)-4-oxobutyl]-4-piperidinyl}-1,3-dihydro-2(2H)-benzimidazolone in 20 ml of THF at a reaction temperature of 0° C. and then stirred for 2 hours at ambient temperature, followed by 1 hour at an internal temperature of 50° C. The mixture was evaporated down in vacuo, the residue was resolved by column chromatography on silica gel (30–60 μm) using dichloromethane/methanol/cyclohexane/conc. ammonia 400/40/40/2.5 v/v/v/v as eluant. By working up the appropriate fractions, 39 mg (17% of theoretical) of 3-acetyl-5-acetylamino-1-{1-[4-(4-amino-3,5-dibromophenyl)-4-oxobutyl]-4-piperidinyl}-1,3-dihydro-2(2H)-benzimidazolone (Item no. 7), colourless crystals (diisopropylether), R$_f$ 0.26 (El A); IR (KBr): 1732.0, 1675.0 (C=O); MS: M$^+$=633/635/637 (Br$_2$), and 22 mg (10% of theoretical) of 5-acetylamino-1-{1-[4-(4-amino-3,5-dibromophenyl)-4-oxobutyl]-4-piperidinyl}-1,3-dihydro-2(2H)-benzimidazolone (Item no. 6), colourless crystals (diisopropylether), R$_f$ 0.29 (El B); IR (KBr) 1695.3 (C=O); MS: M$^+$=591/593/595 (Br$_2$), were obtained.

EXAMPLE 11

1-{1-[4-(4-amino-3,5-dibromophenyl)-4-oxobutyl]-4-piperidinyl}-5-cyclohexanecarbonylamino-1,3-dihydro-2(2H)-benzimidazolone (Item no. 8)

58.64 mg (0.40 mmol) of cyclohexanecarboxylic acid chloride were added to a solution of 200 mg (0.363 mmol) of 5-amino-1-{1-[4-(4-amino-3,5-dibromophenyl)-4-oxobutyl]-4-piperidinyl}-1,3-dihydro-2(2H)-benzimidazolone and 0.056 ml (0.40 mmol) of triethylamine in 10 ml of THF at a reaction temperature of 0° C. and the suspension formed was then stirred for 2 hours at ambient temperature. The mixture was evaporated down in vacuo, the residue was purified by column chromatography on silica gel (30–60 μm) using dichloromethane/methanol/cyclohexane/conc. ammonia 400/40/40/2.5 v/v/v/v as eluant. By working up the appropriate fractions. 106 mg (44% of theoretical) of the desired compound were obtained in the form of colourless crystals (diisopropyl-ether), R$_f$ 0.67 (El B). IR (KBr): 1695.3 (C=O) MS: (M-H$_2$O)$^+$=641/643/645 (Br$_2$)

EXAMPLE 12

5-aminocarbonylamino-1-{1-[4-(4-amino-3,5-dibromophenyl)-4-oxobutyl]-4-piperidinyl}-1,3-dihydro-2(2H)-benzimidazolone (Item no. 9)

1.5 ml of 1N hydrochloric acid, followed by 47 mg (0.723 mmol) of sodium cyanate were added to a solution of 200 mg (0.363 mmol) of 5-amino-1-{1-[4-(4-amino-3,5-dibromophenyl)-4-oxobutyl]-4-piperidinyl}-1,3-dihydro-2(2H)-benzimidazolone in 5 ml of THF at a reaction temperature of 0° C. The ice bath was removed and the mixture was stirred overnight at ambient temperature. The orange-coloured solution was carefully combined with 100 ml of conc. aqueous sodium hydrogen carbonate solution and overlaid with 50 ml of tert.butylmethyl ether. The precipitate formed was suction filtered and purified by column chromatography on silica gel (30–60 μm) using dichloromethane/methanol/cyclohexane/conc. ammonia 400/40/40/2.5 v/v/v/v as eluant. By working up the appropriate fractions 106 mg (44% of theoretical) of the desired compound were obtained in the form of colourless crystals (THF/diethylether 1/1 v/v)), R$_f$ 0.12 (El B). IR (KBr): 3435.0, 3354.0 (NH, NH$_2$); 1701.1, 1662.5 (C=O) MS: ESI: (M+H)$^+$=593/595/597 (Br$_2$); (M+Na)$^+$615/617/619 (Br$_2$)

EXAMPLE 13

Preparation of compounds of general formula:

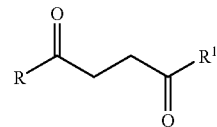

3-{1-[4-(3-chloro-4-dimethylaminophenyl)-1,4-dioxobutyl]-4-piperidinyl}-3,4-dihydro-2(1H)-quinazolinone (Item no. 105)

A solution of 1.05 g (2.248 mmol) of (E)-3-{1-[4-(3-chloro-4-dimethylaminophenyl)-1,4-dioxo-2-buten-1-yl]-4-piperidinyl}-3,4-dihydro-2(1H)-quinazolinone (Item no. 104) in 110 ml of an ethanol-THF mixture (10/1 v/v) was hydrogenated at ambient temperature in the presence of 0.5 g of platinum on active charcoal until the uptake of hydrogen had ended. The mixture was freed from catalyst and solvent and purified by chromatography on silica gel using dichloromethane/methanol/conc. ammonia (95/5/0.3 v/v/v) as eluant. 0.36 g (34% of theoretical) of a colourless substance were obtained, $R_f$ 0.31 (El A). IR (KBr): 1672, 1660 (C=O) MS: $M^+$=468/470 (Cl)

The following was prepared analogously:

| Item no. | N | B | C | remarks | % yield | EI | $R_f$ | MS | IR [cm$^{-1}$] |
|---|---|---|---|---|---|---|---|---|---|
| 73 | N10 | B2 | C28 | Raney Ni as catalyst; MeOH as solvent | 45 | A | 0.30 | $M^+$ = 416 | 2229.6 (CN); 1664.5 (C=O) |

EXAMPLE 14

3-{1-[4-(4-aminomethylphenyl)-1-oxobutyl]-4-piperidinyl}-3,4-dihydro-2(1H)-quinazolinone
(Item no. 77)

A solution of 0.48 g (1.153 mmol) of 3-{1-[4-(4-cyanophenyl)-1,4-dioxobutyl]-4-piperidinyl}-3,4-dihydro-2(1H)-quinazolinone (Item no. 73) and 1.15 ml of 1N hydrochloric acid in 100 ml of methanol was hydrogenated at ambient temperature under 3 bar of pressure in the presence of 0.25 g of 10% palladium on active charcoal until the uptake of hydrogen had ended. The mixture was freed from catalyst and solvent and yielded 0.27 g (58% of theoretical) of a colourless substance, $R_f$ 0.30 (El A). IR (KBr): 1662.5 (C=O) MS: $M^+$406; ESI: $(M+H)^+$=407

EXAMPLE 15

Preparation of compounds of general formula:

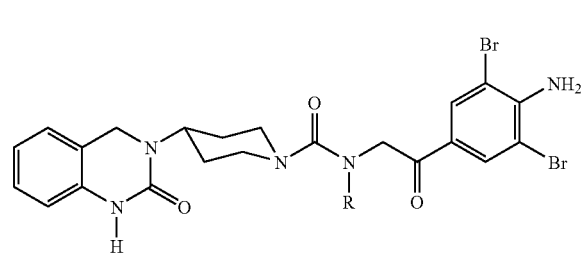

N-[2-(4-amino-3,5-dibromophenyl)-2-oxoethyl]-N-methyl-4-(3,4-dihydro-2(1H)-oxoquinazolin-3-yl)-piperidine-1-carboxamide (Item no. 110)

A mixture of 693.9 mg (3.0 mmol) of 3-(4-piperidinyl)-3,4-dihydro-2(1H)-quinazolinone, 1.2 ml of DIEA and 50 ml of dichloromethane was added dropwise to a solution of 326.4 mg (1.1 mmol) of triphosgene in 50 ml of dichloromethane within 30 minutes. Then a mixture of 1075.4 mg (3.0 mmol) of 1-(4-amino-3,5-dibromophenyl)-2-methylaminoethanone-hydrochloride, 2.4 ml DIEA and 50 ml dichloromethane was added all at once and stirred for 2 hours at ambient temperature. The mixture was washed with 50 ml of dilute aqueous citric acid solution, dried over sodium sulphate, then freed from solvent. The residue remaining was purified by column chromatography on silica gel (Amicon, 35–70 µm) using EE/MeOH/conc. ammonia 95/5/0.5 v/v/v as eluant. The crystalline product was stirred with EtOH, suction filtered and, after washing with diethylether, dried in a circulating air dryer. Yield: 0.1 g (6% of theoretical). M.p. 268–270° C. $R_f$ 0.48 (El A).

IR (KBr): 3442 (NH, NH$_2$), 1664 (C=O). MS: $M^+$577/579/581 (Br$_2$); ESI: $(M-H)^-$=576/578/580 (Br$_2$); $(M+Na)^+$=600/602/604 (Br$_2$)

The following was prepared analogously:

| Item no. | N | B | C | remarks | % yield | EI | $R_f$ | MS | IR [cm$^{-1}$] |
|---|---|---|---|---|---|---|---|---|---|
| 126 | N10 | B11 | C1 | CDT (instead of triphosgene)/ DIEA/THF | 43 | A | 0.50 | ESI: $(M - H)^-$ = 562/564/566 (Br$_2$) | 3450.4, 3323.2 (NH, NH$_2$); 1662.5 (C=O) |

EXAMPLE 16

Preparation of compounds of general formula:

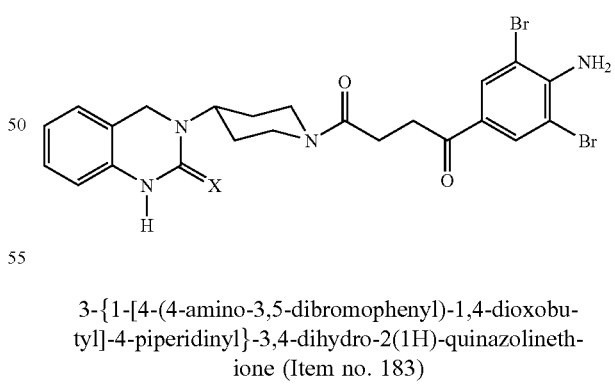

3-{1-[4-(4-amino-3,5-dibromophenyl)-1,4-dioxobutyl]-4-piperidinyl}-3,4-dihydro-2(1H)-quinazolinethione (Item no. 183)

A mixture of 0.5 g (0.929 mmol) of 1-[4-(4-amino-3,5-dibromophenyl)-1,4-dioxobutyl]-N-[(2-aminophenyl)methyl]-4-piperidineamine, 0.2 g (1.122 mmol) of N,N'-thiocarbonyldi-imidazole and 50 ml of DMF was stirred for 1.5 hours at a temperature of 100° C. After cooling the mixture was stirred into 300 ml of water, the precipitate formed was suction filtered, washed thoroughly with 5 ml of methanol and diethyl ether and dried in vacuo. 480 mg (89% of theoretical) of the desired substance were obtained in the form of colourless crystals, $R_f$ 0.97 (El A). IR (KBr): 1669 (C=O) MS: $M^+$=578/580/582 ($Br_2$)

The following was prepared analogously:

| Item no. | N | B | C | remarks | % yield | EI | $R_f$ | MS | IR [cm$^{-1}$] | m.p. [° C.] |
|---|---|---|---|---|---|---|---|---|---|---|
| 184 | N73 | B2 | C1 | cyanoimino-diphenylcarbonate instead of N,N'-thiocarbonyl-diimidazole/DMF/100° C. | 91 | A | 0.91 | $M^+$ = 586/588/590 ($Br_2$) | 2187 (CN) | colourless crystals |

The Examples which follow illustrate the preparation of some pharmaceutical formulations which contain any desired compound of general formula I as active ingredient:

EXAMPLE I

Capsules for Powder Inhalation Containing 1 mg of Active Ingredient

Composition:
1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

Composition:
1 puff contains:

| | |
|---|---|
| active ingredient | 1.0 mg |
| benzalkonium chloride | 0.002 mg |
| disodium edetate | 0.0075 mg |
| purified water ad | 15.0 µl |

Method of preparation:

The active ingredient and benzalkonium chloride are dissolved in water and transferred into Respimat® cartridges.

EXAMPLE III

Inhalable Solution for Nebulisers Containing 1 mg of Active Ingredient

Composition:
1 vial contains:

| | |
|---|---|
| active ingredient | 0.1 g |
| sodium chloride | 0.18 g |
| benzalkonium chloride | 0.002 g |
| purified water ad | 20.0 ml |

Method of preparation:

The active ingredient, sodium chloride and benzalkonium chloride are dissolved in water.

EXAMPLE IV

Propellent Gas-Operated Metering Aerosol Containing 1 mg of Active Ingredient Composition:
1 puff contains:

| | |
|---|---|
| active ingredient | 1.0 mg |
| lecithin | 0.1% |
| propellent gas ad | 50.0 µl |

Method of preparation:

The micronised active ingredient is homogeneously suspended in the mixture of lecithin and propellent gas. The suspension is transferred into a pressurised contained with a metering valve.

EXAMPLE V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of preparation:

The active ingredient and the excipients are dissolved in water and transferred into a suitable container.

EXAMPLE VI

Injectable Solution Containing 5 mg of Active Substance per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

Injectable Solution Containing 100 mg of Active Substance per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4.2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

EXAMPLE VIII

Lyophilisate Containing 10 mg of Active Substance

Composition:

| | |
|---|---|
| Active substance | 10 mg |
| Mannitol | 300 mg |
| human serum albumin | 20 mg |

Preparation:

Mannitol is dissolved in water for injections (WfI); human serum albumin is added; active ingredient is dissolved with heating; made up to specified volume with WfI; transferred into vials; freeze-dried.

Solvent for lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (WfI); transferred into ampoules.

EXAMPLE IX

Tablets Containing 20 mg of Active Substance

Composition:

| | |
|---|---|
| active substance | 20 mg |
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| | |
|---|---|
| active substance | 20 mg |
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size 3 hard gelatine capsules in a capsule filling machine.

EXAMPLE XI

Suppositories Containing 50 mg of Active Substance

Composition:

| active substance | 50 mg |
|---|---|
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:

1. A compound of the formula $$R-Z^1-Z^2-Z^3-R^1 \quad (I),$$

wherein

R denotes a group of the formula $$\begin{array}{c} R^2 \\ \diagdown \\ Y \\ \diagup \\ R^N \end{array} \begin{array}{c} (CHR^5)_o - CHR^3 \\ \diagdown \\ N \\ \diagup \\ (CHR^6)_p - CHR^4 \end{array} \quad (II)$$

wherein o denotes the number 1, p denotes the number 1,

Y denotes a carbon atom, $R^2$ denotes a hydrogen atom, $R^3$ and $R^4$ denote hydrogen atoms, $R^5$ and $R^6$ denote hydrogen atoms, $R^N$ denotes a saturated, mono- or diunsaturated 5- to 7-membered aza, diaza, triaza, oxaza, thiaza, thiadiaza or S,S-dioxido-thiadiaza heterocycle, wherein the abovementioned heterocycles may be linked via a carbon or nitrogen atom and may contain, adjacent to a nitrogen atom, a carbonyl, thioxo or iminocarbonyl group or two carbonyl groups or a carbonyl group and a thioxo or imi-nocarbonyl group, wherein the abovementioned iminocarbonyl groups may be substituted by a cyano group or by an alkoxycarbonyl group with 1 to 4 carbon atoms in the alkyl moiety, may be substituted at one of the nitrogen atoms by an alkanoyl, hydroxycarbonylalkyl or alkoxycarbo-nylalkyl group, may be substituted at one or two carbon atoms by a branched or unbranched alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, wherein the substituents may be identical or different, wherein additionally an unbranched alkylene group with 3 to 6 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or an olefinic double bond of one of the abovementioned unsaturated heterocycles may be fused to a benzene, pyridine, diazine, 1,3-oxazole, thiophene, furan, thiazole, pyrrole, N-methyl-pyrrole, quinoline, imidazole or N-methyl-imidazole ring, or, $R^N$ denotes the hydroxy group, a benzoylaminocar-bonylamino group, a phenylamino group optionally substituted at the aniline nitrogen by an aminocarbonyl group or a phenylmethylamino group optionally substituted at the benzylamine nitrogen by an alkoxycarbonyl group, wherein the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in the groups mentioned under $R^N$ as well as benzo-, thieno-, pyrido-, diazino- and quinolino-fused heterocycles in the carbon skeleton may additionally be mono-, di- or trisubstituted by fluorine, chlorine or bromine atoms, by alkyl groups, by cycloalkyl groups with 3 to 8 carbon atoms, nitro, alkoxy, alkylthio, alkylsulphinyl, alkylsulphonyl, alkylsulphonylamino, phenyl, phenylalkoxy, trifluoromethyl, alkoxycarbonyl, alkoxycarbonyla-lkyl, carboxy, carboxyalkyl, dialkylaminoalkyl, hydroxy, amino, acetylamino, propionylamino, cycloalkanecarbonylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, [4-(1-piperidi-nyl)piperidinyl]carbonyl, [4-(1-piperidinyl)pip-eridinyl]carbonylamino, methylenedioxy, ami-nocarbonylamino, aminocarbonylaminoalkyl, alkylaminocarbonylamino, dialkylaminocarbony-lamino, aminomethyl, alkanoyl, cyano, trifluoromethoxy, trifluoromethylthio, trifluoromethyl-sulphinyl or trifluoromethylsulphonyl groups, wherein the substituents may be identical or different and the abovementioned benzoyl, benzoylamino, benzoylaminocarbonylamino and benzoylmethylamino groups may in turn additionally be substituted in the phenyl moiety by a fluorine, chlorine or bromine atom, an alkyl, trifluoromethyl, amino or acetylamino group, and the alkyl groups contained in the abovementioned groups, unless otherwise stated, may contain 1 to 5 carbon atoms, $Z^1$ denotes a carbonyl group, $Z^2$ denotes the group —CH=CH- $Z^3$ denotes a carbonyl group, and $R^1$ denotes a phenyl group, wherein the abovementioned phenyl group in the carbon skeleton may additionally be mono-, di- or trisubstituted by fluorine, chlorine, bromine or iodine atoms, by alkyl groups, by cycloalkyl groups with 3 to 8 carbon atoms, phenylalkyl groups, hydroxy, alkoxy, phenyl, phenylalkoxy, trifluoromethyl, alkoxycarbonylalkyl, carboxyalkyl, alkoxycarbonyl, carboxy, dialkylaminoalkyl, amino, aminoalkyl, alkylamino, dialkylamino, acetylamino, propionylamino, benzoyl, benzoylamino, benzoylmethylamino, 4-(dialkylaminoalkyl)-1-piperazinyl, piperidinyl, 4-(1-piperidinyl)-1-piperidinyl, 4-(4-methyl-1-piperazinyl)-1-piperidinyl, 4-(4-dialkylaminoalkyl-1-piperazinyl)-1-piperidinyl, nitro, methanesulphonyloxy, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups and the substituents may be identical or different and the abovementioned benzoyl, benzoylamino and benzoylmethylamino groups may in turn additionally be substituted in the phenyl moiety by a fluorine, chlorine or bromine atom or by an alkyl, trifluoromethyl, amino or acetylamino group, wherein the hydroxy, amino and imidazolyl groups contained in the abovementioned groups may be substituted with acetyl, benzyloxycarbonyl or tert.butyloxycarbonyl group, all the abovementioned alkyl and alkoxy groups and the alkyl or alkylene moieties present inside the other groups specified may contain 1 to 7 carbon atoms, unless otherwise stated, and all the abovementioned cycloalkyl groups and the cycloalkyl groups present inside the other groups specified may contain 5 to 10 carbon atoms, unless otherwise stated, or a tautomer, diastereomer, enantiomer or salt thereof.

2. A compound according to claim 1, wherein

R denotes a group of the formula

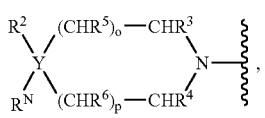

(II)

wherein o, p, $R^5$, $R^6$ and Y are as defined in claim 1, $R^N$ denotes a monocyclic saturated, mono- or diunsaturated 5- to 7-membered aza, diaza, triaza, oxaza, thiaza, thiadiaza- or S,S-dioxido-thiadiaza heterocycle containing one to two imino groups, wherein the abovementioned heterocycles are linked via a carbon or nitrogen atom and adjacent to a nitrogen atom contain a carbonyl, thioxo or iminocarbonyl group or two carbonyl groups or a carbonyl group and a thioxo or iminocarbonyl group, wherein the abovementioned iminocarbonyl groups may be substituted by a cyano group or by an alkoxycarbonyl group with 1 to 4 carbon atoms in the alkyl moiety, the abovementioned heterocycles containing two imino groups may be substituted at one of the imino-nitrogen atoms by an alkanoyl, hydroxycarbonylalkyl or alkoxycarbonylalkyl group with 1 to 3 carbon atoms in the alkyl moieties, may be substituted at one or two carbon atoms by an unbranched alkyl group, by a phenyl, phenylmethyl, naphthyl, biphenylyl or thienyl group, wherein the substituents may be identical or different, and wherein additionally an unbranched alkylene group with 3 to 4 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or an olefinic double bond of one of the abovementioned unsaturated heterocycles may be fused to a benzene, pyridine, diazine, thiophene or quinoline ring, with the provisos that (i) $R^N$ does not take on the meaning of the 2,6-dioxo-3-phenyl-3,4,5,6-tetrahydro-1H-pyrimidin-3-yl group, the 2-oxo-1,3,4,5-tetrahydro-1-imidazolyl group optionally monosubstituted by an acyl group in the 3 position and the 2(1H)-oxo-3,4,5,6-tetrahydro-1-pyrimidinyl group and (ii) $R^1$ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group if $R^N$ takes on the meaning of the 1,3-dihydro-2(2H)-oxobenzimidazol-1-yl, 1,3-dihydro-2(2H)-thioxobenzimidazol-1-yl, 2(1H)-oxoquinoxalin-1-yl, 3-oxo-2,3-dihydrobenzoxazin-4-yl, 3-oxo-2,3,4,5-tetrahydrobenz[f][1,4]oxazepin-4-yl or 2(1H)-oxoquinolin-3-yl group, or, with the proviso that (i) $R^1$ does not denote a 2-alkoxy-4-amino-5-bromophenyl, 2-alkoxy-4-amino-5-chlorophenyl or naphthyl group, $R^N$ may also represent the hydroxy group or a benzoylaminocarbonylamino group, a phenylamino group optionally at least monosubstituted at the aniline nitrogen by an aminocarbonyl group and in the phenyl moiety, or, a phenylmethylamino group optionally at least monosubstituted at the benzylamine nitrogen by a $C_{1-4}$-alkoxy-carbonyl group and in the phenyl moiety, wherein the phenyl and thienyl groups contained in the groups mentioned under $R^N$ as well as benzo-, thieno-, pyrido-, diazino- and quinolino-fused heterocycles may additionally be mono-, di- or trisubstituted in the carbon skeleton by fluorine, chlorine or bromine atoms, by methyl groups, by cycloalkyl groups with 5 to 6 carbon atoms, nitro, methoxy, methylthio, methylsulphinyl, methylsulphonyl, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, [4-(1-piperidinyl)-piperidinyl]carbonyl, [4-(1-piperidinyl)piperidinyl]-carbonylamino, aminocarbonylamino, alkylaminocarbonylamino, dialkylaminocarbonylamino, aminomethyl, acetyl, cyano or trifluoromethoxy groups, wherein the substituents may be identical or different, and $R^1$ denotes a mono-, di- or trisubstituted phenyl group,
 wherein the abovementioned phenyl group may be mono-, di- or trisubstituted in the carbon skeleton by fluorine, chlorine, bromine or iodine atoms, by alkyl groups with 1 to 4 carbon atoms, by cycloalkyl groups with 5 to 6 carbon atoms, hydroxy, alkoxy, phenyl, trifluoromethyl, methoxycarbonyl, ethoxycarbonyl, carboxy, amino, aminomethyl, methylamino, dimethylamino, acetylamino, 4-[3-(dimethylaminopropyl)]-1-piperazinyl, piperidinyl, 4-(1-piperidinyl)-1-piperidinyl, 4-(4-methyl-1-piperazinyl)-1-piperidinyl, 4-[4-(3-dimethylaminopropyl)-1-piperazinyl]-1-piperidinyl, nitro, methanesulphonyloxy, aminocarbonyl, acetyl, cyano or trifluoromethoxy groups and the substituents may be identical or different, wherein all the abovementioned alkyl and alkoxy groups and the alkyl or alkylene moieties present inside the other groups specified may contain 1 to 5 carbon atoms unless otherwise stated, or a tautomer, diastereomer, enantiomer or salt thereof.

3. A compound according to claim 1, wherein R denotes a group of the formula

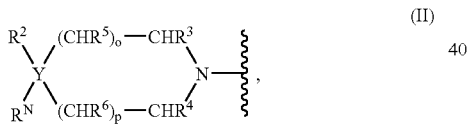

(II)

wherein o, p and Y are as defined in claim 1, $R^N$ denotes a monocyclic saturated, mono- or diunsaturated 5- to 7-membered aza, diaza, triaza, thiadiaza or S,S-dioxido-thiadiaza heterocycle containing one to two imino groups,
 wherein the abovementioned heterocycles are linked via a carbon or nitrogen atom and
 adjacent to a nitrogen atom contain a carbonyl, thioxo or iminocarbonyl group or two carbonyl groups or a carbonyl group and a thioxo or iminocarbonyl group, wherein the abovementioned iminocarbonyl groups may be substituted by a cyano group or by a tert.butoxycarbonyl group,
 the abovementioned heterocycles containing two imino groups may be substituted at one of the imino-nitrogen atoms by an acetyl, carboxymethyl or methoxycarbonylmethyl group,
 may be substituted at one or two carbon atoms by a methyl group, by a phenyl, phenylmethyl, naphthyl, biphenylyl or thienyl group, wherein the substituents may be identical or different,
 and wherein additionally an unbranched alkylene group with 4 carbon atoms may be attached to the abovementioned 5- to 7-membered heterocycles via two adjacent carbon atoms or the group =CH—S—CH= may be attached to the abovementioned 5- to 7-membered saturated heterocycles via two adjacent carbon atoms or
 an olefinic double bond of one of the abovementioned unsaturated heterocycles may be fused to a benzene, pyridine, diazine, thiophene or quinoline ring,
 with the provisos that
 (i) $R^N$ does not take on the meaning of the 2,6-dioxo-3-phenyl-3,4,5,6-tetrahydro-1H-pyrimidin-3-yl group, the 2-oxo-1,3,4,5-tetrahydro-1-imidazolyl group optionally monosubstituted in the 3 position by an acyl group and the 2(1H)-oxo-3,4,5,6-tetrahydro-1-pyrimidinyl group, and
 (ii) $R^1$ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group, if $R^N$ takes on the meaning of the 1,3-dihydro-2(2H)-oxobenzimidazol-1-yl, 1,3-dihydro-2(2H)-thioxobenzimidazol-1-yl, 2(1H)oxoquinoxalin-1-yl, 3-oxo-2,3-dihydrobenzoxazin-4-yl, 3-oxo-2,3,4,5-tetrahydrobenz[f][1,4]oxazepin-4-yl or 2(1H)-oxoquinolin-3-yl group,
 or, with the proviso that
 (i) $R^1$ does not denote a 2-alkoxy-4-amino-5-bromophenyl, 2-alkoxy-4-amino-5-chlorophenyl or naphthyl group, $R^N$ may also denote the hydroxy group, a benzoylaminocarbonylamino group, a phenylamino group optionally at least monosubstituted by an aminocarbonyl group at the aniline nitrogen and in the phenyl moiety, a phenylmethylamino group optionally at least monosubstituted by a tert.butoxycarbonyl group at the benzylamine nitrogen and in the phenyl moiety,
 wherein the phenyl and thienyl groups contained in the groups mentioned under R as well as benzo-, thieno-, pyrido-, diazino- and quinolino-fused heterocycles may additionally be mono-, di- or trisubstituted in the carbon skeleton by fluorine, chlorine or bromine atoms, by methyl, nitro, methoxy, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (4-methyl-1-piperazinyl)-carbonyl, [4-(1-piperidinyl)-1-piperidinyl]carbonyl, [4-(1-piperidinyl)piperidinyl]carbonylamino, aminomethyl or aminocarbonylamino groups, wherein the substituents may be identical or different, $R^1$ denotes a monosubstituted phenyl group,
 wherein the abovementioned phenyl group may be substituted by fluorine, chlorine, bromine or iodine atoms, by alkyl groups with 1 to 4 carbon atoms, by cyclohexyl, hydroxy, alkoxy groups with up to 3 carbon atoms in the alkyl moiety, phenyl, trifluoromethyl, methoxycarbonyl, ethoxycarbonyl, carboxy, amino, aminomethyl, methylamino, dimethylamino, acetylamino, 4-[3-(dimethylaminopropyl)-1-piperazinyl, piperidinyl, 4-(1-piperidinyl)-1-piperidinyl, 4-(4-methyl-1-piperazinyl)-1- piperidinyl, 4-[4-(3-dimethylaminopropyl)-1-piperazinyl)-1-piperidinyl, nitro, cyano or trifluoromethoxy groups and the substituents may be identical or different, or a tautomer, diastereomer, enantiomer or salt thereof.

4. A compound according to claim 1, wherein R denotes a group of the formula

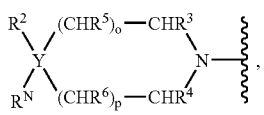

(II)

wherein $R^N$ denotes a 3,4-dihydro-2(1H)-oxoquinazolin-3-yl, 3,4-dihydro-2(1H)-oxoquinazolin-1-yl, 1,3-dihydro-4-phenyl-2H-2-oxoimidazol-1-yl, 3,4-dihydro-2 (1H)-oxopyrido[2,3-d]pyrimidin-3-yl, 4-phenyl-1,3,4,5-tetrahydro-2H-2-oxoimidazol-1-yl, 1,3-dihydro-5-methyl-4-phenyl-2H-2-oxoimidazol-1-yl, 3,4-dihydro-2(1H)-oxothieno[3,4-d]pyrimidin-3-yl, 1,3-dihydro-4-(3-thienyl)-2H-2-oxoimidazol-1-yl, 2,4-dihydro-5-phenyl-3(3H)-oxo-1,2,4-triazol-2-yl, 3,4-dihydro-2(1H)-oxothieno-[3,2-d]pyrimidin-3-yl, 3,4-dihydro-2(1H)-oxopyrido[3,4-d]pyrimidin-3-yl, 3,4-dihydro-2(1H)-oxopyrido[4,3-d]pyrimidin-3-yl, 3,4-dihydro-2(1H)-oxoquinolin-3-yl, 2(1H)-oxoquinoxalin-3-yl, 1,1-dioxido-3(4H)-oxo-1,2,4-benzothiadiazin-2-yl, 1,3-dihydro-2(2H)-oxoimidazo[4,5-d]pyrimidin-3-yl, 3,4,4a,5,6,7,8,8a-octahydro-2(1H)-oxoquinazolin-3-yl, 2,5-dioxo-4-(phenylmethyl)-imidazolidin-1-yl, 2,5-dioxo-4-phenyl-imidazolidin-1-yl, 3,4-dihydro-2,2-dioxido-2,1,3-benzothiadiazin-3-yl, 1,3-dihydro-4-(2-naphthyl)-2H-2-oxoimidazol-1-yl, 4-(4-biphenylyl)-1,3-dihydro-2H-2-oxoimidazol-1-yl, 1,3-dihydro-2(2H)-oxoimidazo[4,5-c]quinolin-3-yl, 2-(dimethylethoxycarbonylamino)-3,4-dihydroquinazolin-3-yl, 2-amino-3,4-dihydroquinazolin-3-yl, 3,4-dihydro-2(1H)-thioxoquinazolin-3-yl, 3,4-dihydro-2(1H)-cyanoiminoquinazolin-3-yl, 2,3,4,5-tetrahydro-2(1H)-oxo-1,3-benzodiazepin-3-yl or 2,4 (1H,3H)-dioxoquinazolin-3-yl group or, if $R^1$ does not denote a 2-alkoxy-4-amino-5-chlorophenyl, 2-alkoxy-4-amino-5-bromophenyl, 2-alkoxy-4-acetylamino-5-chlorophenyl or 2-alkoxy-4-acetylamino-5-bromophenyl group, may also denote a 1,3-dihydro-2(2H)-oxobenzimidazol-1-yl or 2(1H)-oxoquinolin-3-yl group, wherein the abovementioned mono- and bicyclic heterocycles containing two imino groups may be substituted at one of the imino-nitrogen atoms by an acetyl, carboxymethyl or methoxycarbonylmethyl group and/or may additionally be mono-, di- or trisubstituted in the carbon skeleton and/or at the phenyl groups contained in these groups by fluorine, chlorine or bromine atoms, by methyl groups, nitro, methoxy, methanesulphonylamino, phenyl, trifluoromethyl, methoxycarbonyl, carboxy, hydroxy, amino, acetylamino, cyclohexanecarbonylamino, aminocarbonyl, hydroxyethylaminocarbonyl, (4-morpholinyl)carbonyl, (4-methyl-1-piperazinyl)carbonyl, [4-(1-piperidinyl)-1-piperidinyl]carbonyl, [4-(1-piperidinyl)piperidinyl]carbonylamino or aminocarbonylamino groups, wherein the substituents may be identical or different and multiple substitution with the last six substituents is ruled out, or, with the proviso that
(i) $R^1$ does not denote a 2-alkoxy-4-amino-5-bromophenyl, 2-alkoxy-4-amino-5-chlorophenyl or naphthyl group $R^N$ may also denote the hydroxy group, or a benzoylaminocarbonylamino group, a phenylamino group optionally at least monosubstituted by an aminocarbonyl group at the aniline nitrogen and in the phenyl moiety or a phenylmethylamino group optionally at least monosubstituted by a tert.butoxycarbonyl group at the benzylamine nitrogen and in the phenyl moiety, $R^1$ is defined as in claim 3, or a tautomer, diastereomer, enantiomer or salt thereof.

5. A physiologically acceptable salt of a compound according to claim 1, 2, or 3, formed with an inorganic or organic acid or base.

6. A physiologically acceptable salt of a compound according to claim 4 formed with an inorganic or organic acid or base.

7. A compound selected from the group consisting of:
(45) (E)-3-{1-[4-(4-bromophenyl)-1,4-dioxo-2-buten-1-yl]-4-piperidinyl}-3,4-dihydro-2(1H)-quinazolinone;
(46) (E)-3,4-dihydro-3-{1-[4-(3,4-dimethylphenyl)-1,4-dioxo-2-buten-1-yl]-4-piperidinyl}-2(1H)-quinazolinone;
(47) (E)-3,4-dihydro-3-{1-[1,4-dioxo-4-(4-hydroxyphenyl)-2-buten-1-yl]-4-piperidinyl}-2(1H)-quinazolinone;
(49) (E)-3,4-dihydro-3-{1-[4-[4-(1,1-dimethylethyl)phenyl]-1,4-dioxo-2-buten-1-yl]-4-piperidinyl}-2(1H)-quinazolinone;
(50) (E)-3-{1-[4-(3,4-dichlorophenyl)-1,4-dioxo-2-buten-1-yl]-4-piperidinyl}-3,4-dihydro-2(1H)-quinazolinone;
(51) (E)-3,4-dihydro-3-{1-[1,4-dioxo-4-(3-nitrophenyl)-2-buten-1-yl]-4-piperidinyl}-2(1H)-quinazolinone;
(52) (E)-3,4-dihydro-3-{1-[1,4-dioxo-4-(3-methylphenyl)-2-buten-1-yl]-4-piperidinyl}-2(1H)-quinazolinone;
(53) (E)-3,4-dihydro-3-{1-[4-(4-cyclohexylphenyl)-1,4-dioxo-2-buten-1-yl]-4-piperidinyl}-2(1H)-quinazolinone;
(54) (E)-3-{1-[4-[3,5-bis-(1,1-dimethylethyl)-4-hydroxyphenyl]-1,4-dioxo-2-buten-1-yl]-4-piperidinyl}-3,4-dihydro-2(1H)-quinazolinone;
(55) (E)-3-{1-[4-(4-chloro-3-methylphenyl)-1,4-dioxo-2-buten-1-yl]-4-piperidinyl}-3,4-dihydro-2(1H)-quinazolinone;
(56) (E)-3-{1-[4-(3-bromo-4-nitrophenyl)-1,4-dioxo-2-buten-1-yl]-4-piperidinyl}-3,4-dihydro-2(1H)-quinazolinone;
(57) (E)-3-{1-[4-(3-bromophenyl)-1,4-dioxo-2-buten-1-yl]-4-piperidinyl}-3,4-dihydro-2(1H)-quinazolinone;
(71) (E)-3-{1-[4-(4-cyanophenyl)-1,4-dioxo-2-buten-1-yl]-4-piperidinyl}-3,4-dihydro-2(1H)-quinazolinone;
(74) (E)-3-{1-[4-(4-amino-3-cyano-5-fluorophenyl)-1,4-dioxo-2-buten-1-yl]-4-piperidinyl}-3,4-dihydro-2(1H)-quinazolinone;
(82) (E)-3-{1-[4-(4-amino-3,5-dibromophenyl)-1,4-dioxo-2-buten-1-yl]-4-piperidinyl}-3,4-dihydro-2(1H)-quinazolinone;
(83) (E)-1-{1-[4-(4-amino-3,5-dibromophenyl)-1,4-dioxo-2-buten-1-yl]-4-piperidinyl}-1,3-dihydro-4-phenyl-2 (2H)-imidazolone;

(103) (E)-3-{1-[4-[3-chloro-4-(dimethylamino)phenyl]-1,4-dioxo-2-buten-1-yl]-4-piperidinyl}-3,4-dihydro-2(1H)-quinazolinone;

(167) (E)-3-{1-[4-(4-biphenylyl)-1,4-dioxo-2-buten-1-yl]-4-piperidinyl}-3,4-dihydro-2(1H)-quinazolinone;

(168) (E)-3,4-dihydro-3-{1-[1,4-dioxo-4-(4-ethoxycarbonylphenyl)-2-buten-1-yl]-4-piperidinyl}-2(1H)-quinazolinone;

(169) (E)-3,4-dihydro-3-{1-[1,4-dioxo-4-(3,4,5-trimethoxyphenyl)-2-buten-1-yl]-4-piperidinyl}-2(1H)-quinazolinone;

(170) (E)-3,4-dihydro-3-{1-[1,4-dioxo-4-(3-trifluoromethoxyphenyl)-2-buten-1-yl]-4-piperidinyl}-2(1H)-quinazolinone;

(171) (E)-3,4-dihydro-3-{1-[1,4-dioxo-4-(3-ethylphenyl)-2-buten-1-yl]-4-piperidinyl}-2(1H)-quinazolinone;

(172) (E)-3,4-dihydro-3-{1-[1,4-dioxo-4-(3-methoxyphenyl)-2-buten-1-yl]-4-piperidinyl}-2(1H)-quinazolinone;

(173) (E)-3,4-dihydro-3-{1-[1,4-dioxo-4-(4-methylethoxyphenyl)-2-buten-1-yl]-4-piperidinyl}-2(1H)-quinazolinone;

(174) (E)-3,4-dihydro-3-{1-[1,4-dioxo-4-(3-fluoro-4-methoxyphenyl)-2-buten-1-yl]-4-piperidinyl}-2(1H)-quinazolinone;

(175) (E)-3,4-dihydro-3-{1-[1,4-dioxo-4-[4-(1-piperidinyl)-phenyl]-2-buten-1-yl]-4-piperidinyl}-2(1H)-quinazolinone;

(177) (E)-3,4-dihydro-3-{1-[1,4-dioxo-4-(4-trifluoromethyl-phenyl)-2-buten-1-yl]-4-piperidinyl}-2(1H)-quinazolinone; and (178) (E)-3,4-dihydro-3-{1-[1,4-dioxo-4-(4-carboxyphenyl)-2-buten-1-yl]-4-piperidinyl}-2(1H)-quinazolinone;
or a salt thereof.

8. A pharmaceutical composition comprising a compound according to claim 1 and one or more inert carriers and/or diluents.

9. A method of treating migraine or cluster headaches which method comprises administering to a patient in need thereof a pharmaceutically effective amount of a compound according to claim 1.

\* \* \* \* \*